(12) United States Patent
Haseba et al.

(10) Patent No.: US 6,685,995 B1
(45) Date of Patent: Feb. 3, 2004

(54) ESTER COMPOUNDS, LIQUID CRYSTAL COMPOSITIONS AND LIQUID CRYSTAL DISPLAY DEVICES

(75) Inventors: Yasuhiro Haseba, Kanagawa (JP); Shuichi Matsui, Chiba (JP); Hiroyuki Takeuchi, Chiba (JP); Yoshitaka Yagi, Chiba (JP); Fusayuki Takeshita, Chiba (JP); Etsuo Nakagawa, Chiba (JP)

(73) Assignee: Chisso Corporation, Osaka (JP)

( * ) Notice: Subject to any disclaimer, the term of this patent is extended or adjusted under 35 U.S.C. 154(b) by 0 days.

(21) Appl. No.: 09/582,920

(22) PCT Filed: Jan. 8, 1999

(86) PCT No.: PCT/JP99/00046
§ 371 (c)(1),
(2), (4) Date: Jul. 7, 2000

(87) PCT Pub. No.: WO99/35118
PCT Pub. Date: Jul. 15, 1999

(30) Foreign Application Priority Data

Jan. 9, 1998 (JP) .............................................. 10/14904

(51) Int. Cl.$^7$ ........................ C09K 19/30; C09K 19/34; C09K 19/12; C09K 19/20; C07C 69/75; C07C 69/76; C07D 239/24; C07D 319/06

(52) U.S. Cl. ............. 428/1.1; 252/299.61; 252/299.63; 252/299.64; 252/299.67; 544/298; 544/303; 549/369; 560/64; 560/65; 560/128; 570/126; 570/128; 570/131

(58) Field of Search ...................... 252/299.67, 299.61, 252/299.63, 299.62, 299.64, 299.65; 560/64, 65, 128; 544/298, 303; 549/369; 570/126, 128, 131; 428/1.1

(56) References Cited

U.S. PATENT DOCUMENTS 4,592,858 A * 6/1986 Higuchi et al. ......... 252/299.66
5,196,140 A * 3/1993 Poetsch et al. .......... 252/299.6

FOREIGN PATENT DOCUMENTS

JP 2-25451 1/1990
JP 2-304083 12/1990
JP 9-31064 2/1997

OTHER PUBLICATIONS

Torgova et al., "Phenacyl esters. A new class of liquid–crystalline compound", Liq. Cryst. (1991), 10(6), p. 881–886.

* cited by examiner

Primary Examiner—Shean C. Wu
(74) Attorney, Agent, or Firm—Wenderoth, Lind & Ponack, LLP

(57) ABSTRACT

Liquid crystalline compounds suitable for driving at a low voltage and at a wide temperature range, and suitable for high speed response, liquid crystal compositions comprising the compound, and liquid crystal display devices comprising the liquid crystal composition. The crystalline compounds are ester compounds expressed by the general formula (1)

$$R_1 (A_1-Za)_{n1} (A_2-Zb)_{n2} (A_3-Zc)_{n3} A_4-Zd-A_5-Ze-Y_1 \underset{Y_2}{\overset{}{\diagdown}} R_2 \quad (1)$$

wherein $R_1$ represents e.g. a hydrogen atom; $A_1$ to $A_5$ each independently represent e.g. 1,4-cyclohexylene, 1,4-phenylene, 1-cyclohexene-1,4-diyl, 3-cyclohexene-1,4-diyl, 1-sila-1,4-cyclohexylene, or 4-sila-1,4-cyclohexylene; bonding groups Za to Zd each independently represent e.g. a single bond, —$CH_2$—, —O—, —C≡C—, or an alkylene group or alkenylene group having 2 to 4 carbon; bonding group Ze represents e.g. a single bond, an alkylene group or alkenylene group having 1 to 10 carbon atoms; $n1$ to $n3$ are each independently 0 or 1, but $n1 \leq n2 \leq n3$; $Y_1$ and $Y_2$ each independently represent oxygen atom or sulfur atom; $R_2$ represents e.g. a halogen atom, a straight chain or branched alkyl group having 1 to 20 carbon atoms, or straight chain or branched alkenyl group having 2 to 20 carbon atoms; provided that when $A_5$ represents unsubstituted 1,4-phenylene, then Zd is a single bond, and $A_4$ is not 1,4-phenylene; and each atom which constitutes this compound may be replaced by its isotope.

16 Claims, No Drawings

ESTER COMPOUNDS, LIQUID CRYSTAL COMPOSITIONS AND LIQUID CRYSTAL DISPLAY DEVICES

TECHNICAL FIELD

The present invention relates to liquid crystalline compounds and liquid crystal compositions. More specifically, the invention relates to liquid crystalline ester compounds preferable as component of liquid crystal compositions particularly for TN mode, STN mode, or TFT mode, to liquid crystal compositions comprising the compounds, and to liquid crystal display devices fabricated by using the liquid crystal composition as a material to be incorporated therein. In this specification, the term "liquid crystalline compounds" is used as a generic name both for the compounds which exhibit a liquid crystal phase and the compounds which do not exhibit a liquid crystal phase but are useful as component of liquid crystal compositions.

BACKGROUND ART

Liquid crystal display devices employ optical anisotropy and dielectric anisotropy of liquid crystal substances; the devices are classified by their displaying method into various modes such as twisted nematic (TN) mode, dynamic scattering (DS) mode, guest-host (GH) mode, deformation of aligned phases (DAP) mode, super-twisted nematic (STN) mode, electrically controlled birefringence (VCB, ECB, or TB) mode, and vertical alignment (VA) mode; and properties of liquid crystal substances suitable for each of the modes are different. It is necessary to the liquid crystal substances used for any mode of display devices that the liquid crystal substances are stable against moisture, air, heat, and light. For liquid crystal materials employed in display devices particularly using active matrix driving, especially high voltage holding ratio is required.

In recent years, investigations for lowering driving voltage of liquid crystal display devices have been conducted and thus liquid crystal materials having large absolute value of dielectric anisotropy Δε have been sought. For instance, in TN mode, liquid crystal materials having positive and large Δε value make driving of the devices at a low voltage possible, and in VA mode, liquid crystal materials having negative and large Δε make the low voltage driving possible. Besides, in the case of in-plane switching (IPS) mode employing the change in birefringence of liquid crystal materials by on-off switching of transverse electric field (electric field directed parallel to the plane of the substrates), liquid crystal materials having large Δε or -Δε have been sought.

In order to increase response speed of liquid crystal display devices, low viscosity is required of liquid crystal materials. In order to make display in a practically wide temperature range possible, excellent miscibility at low temperatures and high clearing point are required of liquid crystal materials.

Further, it is also required that liquid crystal materials used for STN mode have steep threshold characteristics.

Since most favorable optical anisotropy value Δn of liquid crystal compositions is different depending on display mode and cell thickness, Δn value required of liquid crystal compounds is in a wide range.

It is known that when the benzene ring at the core part of liquid crystal compounds is replaced by cyclohexane ring, Δn value of the liquid crystal compounds becomes small (KIKAN KAGAKU SOSETSU (Seasonal publication, General Remarks in Chemistry) No. 22, 1994, Chemistry of Liquid Crystals, page 43). In connection with the structure of the core part, knowledge in the past on the characteristics of liquid crystalline compounds classified by the presence or absence of an aromatic ring such as benzene ring and pyrimidine ring at the core part is described below.

Liquid crystalline compounds having no aromatic ring at the core part generally have small Δn value. For instance, 4-(4-pentylcyclohexyl)cyclohexanecarbonitrile (Compound (10)) is described on page 44 of the Chemistry of Liquid Crystals described above. Extrapolated Δn value of this compound is 0.06 (according to the determination by the present inventors, the value is 0.068).

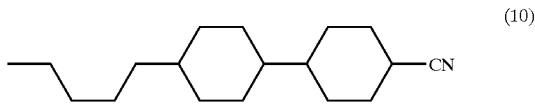

(10)

As shown in Example 31 (Comparative Example 1) described below, extrapolated Δε value of the compound (10) is as small as 3.7 and extrapolated value of viscosity is as high as 55.0 mPa·s according to the determinations by the present inventors. Thus, whereas the compound (10) has small Δn value, it is difficult to actualize low voltage driving of liquid crystal display devices due to its small Δε value, and it is also difficult to actualize high speed response due to its high viscosity. Besides, its voltage holding ratio is low, and therefore the compound cannot be used for liquid crystal display devices for TFT mode.

In Mol. Cryst. Liq. Cryst., 1991, Vol. 204, pages 86 and 84, 4-(4-propylcyclohexyl)cyclohexyl trifluoromethyl ketone (Compound (11)) and 4-(4-propylcyclohexyl) cyclohexanecarboxylic acid 2,2,2-trifluoroethyl ester (Compound (12)) are described, respectively. Whereas these compounds also have small Δn value, their Δε value are as small as 5.1 and 2.0, respectively, and thus it is difficult to actualize low voltage driving.

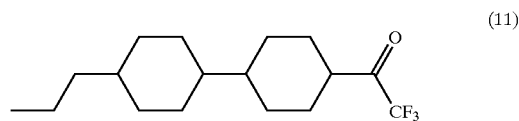

(11)

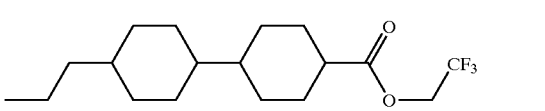

(12)

At present, exploitation of compounds having large absolute value of Δε and low viscosity while having small Δn value are required.

As the compounds having an aromatic ring at the core part and having large Δε value, following compounds in which cyano group or halogen atoms are bonded to the benzene ring at a terminal of molecule are known.

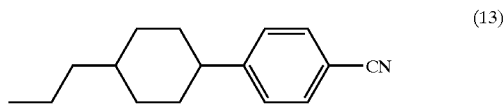

(13)

-continued

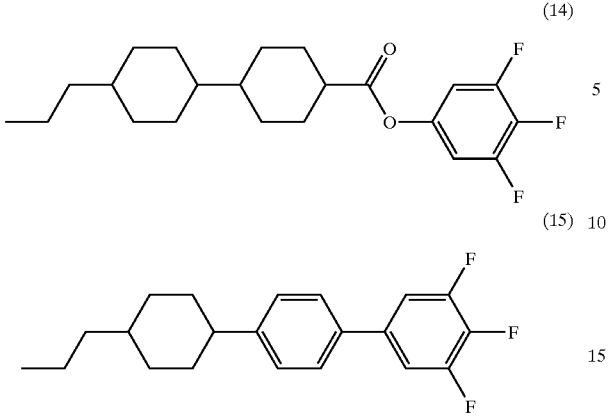

Whereas all these compounds have medium or large Δn value since they have an aromatic ring, the compound (13) has low voltage holding ratio and thus can not stand in the use for TFT. Whereas Compounds (14) and (15) have good voltage holding ratio, they have disadvantages that clearing point is low and viscosity is high. As shown in Example 32 (Comparative Example 2) described below, clearing point of the compound (14) is as low as 95.7° C. and its viscosity is as high as 46.3 mPa·s. Accordingly, exploitation of compounds having high clearing point, low viscosity, and high voltage holding ratio while having medium or large Δn value are currently required.

DISCLOSURE OF THE INVENTION

An object of the present invention is to solve the defects in conventional technology. Another object of them present invention is to provide liquid crystalline compounds having large Δε value and low viscosity while having small Δn value, or liquid crystalline compounds having high voltage holding ratio, high clearing point, and low viscosity while having medium or large Δn value; to provide liquid crystal compositions comprising one side or both sides of the compounds described above thereby low voltage driving, high speed response, and driving at a wide temperature range of liquid crystal display devices become possible; and to provide liquid crystal display devices fabricated by using the liquid crystal composition as material to be incorporated in the devices.

As a result of the investigations by the present inventors to achieve the objects described above, it has been found that compounds having an ester group in which a halogen atom or halogenated alkyl group is bonded to the carbon atom of carbonyl, and having no aromatic ring at the core part have small Δn value, large Δε value, low viscosity, and high voltage holding ratio, that such compounds as described above but having an aromatic ring at the core part have medium or large Δn value, high voltage holding ratio, high clearing point, and low viscosity, and that liquid crystal compositions comprising the former compound or the latter compound are the most suitable materials for low voltage driving, driving at a wide temperature range to be used, and high speed response of diversified liquid crystal display devices, leading to the accomplishment of the present invention.

That is, the present invention is summarized as follows:

(1) An ester compound expressed by the general formula (1)

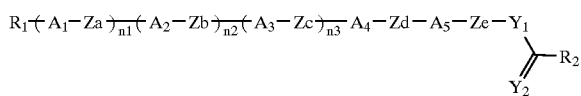

wherein $R_1$ represents hydrogen atom, cyano group, nitro group, amino group, a halogen atom, a straight chain or branched alkyl group having 1 to 20 carbon atoms, or a straight chain or branched alkenyl group having 2 to 20 carbon atoms; one or more hydrogen atoms in these alkyl group and alkenyl group may be replaced by halogen atoms; one or more —$CH_2$— in these alkyl group and alkenyl group may be replaced by oxygen atoms or sulfur atoms, but there is no case where oxygen atoms are adjacent; and one or more carbon atoms in these alkyl group and alkenyl group may be replaced by silicon atoms;

rings $A_1$ to $A_5$ each independently represent 1,4-cyclohexylene, 1,4-phenylene, 1-cyclohexene-1,4-diyl, 3-cyclohexene-1,4-diyl, 1-sila-1,4-cyclohexylene, or 4-sila-1,4-cyclohexylene; one or more —$CH_2$— in the 1,4-cyclohexylene, 1-cyclohexene-1,4-diyl, and 3-cyclohexene-1,4-diyl may each independently be replaced by oxygen atoms, sulfur atoms, —CO—, —CS—, $SiH_2$—, —NH—, —$CF_2$—, or —CFH—, but there is no case where oxygen atoms are adjacent; hydrogen atoms which bond to carbon atoms at position 2 and position 3, respectively, in the 1-cyclohexene-1,4-diyl or 3-cyclohexene-1,4-diyl may each independently be replaced by fluorine atoms; one or more hydrogen atoms in the 1,4-phenylene may each independently be replaced by halogen atoms, halogenated alkyl groups having 1 to 3 carbon atoms, methyl groups, cyano groups, or nitro groups; and one or more —CH= is the 1,4-phenylene may each independently be replaced by nitro groups;

bonding groups Za to Zd each independently represent single bond, —$CH_2$—, —O—, —C≡C—, or an alkylene group or alkenylene group having 2 to 4 carbon atoms; one or more hydrogen atoms in these groups may be replaced by halogen atoms; and —$CH_2$— in these groups may each independently be replaced by oxygen atom, sulfur atom, —CO—, —CS—, —NH—, —$CF_2$—, or —CFH—, but there is no case where oxygen atoms are adjacent;

bonding group Ze represents single bond, an alkylene group having 1 to 10 carbon atoms, or alkenylene group; and —$CH_2$— in these groups may each independently be replaced by oxygen atom, sulfur atom, —CO—, —$CF_2$—, —CFH—, —CH=CH—, —CF=CF—, —CF=CH—, or —C≡C—, but there is no case where oxygen atoms are adjacent;

n1 to n3 are each independently 0 or 1, but $n1 \leq n2 \leq n3$;

$Y_1$ and $Y_2$ each independently represent oxygen atom or sulfur atom;

$R_2$ represents a halogen atom, a straight chain or branched alkyl group having 1 to 20 carbon atoms, or straight chain or branched alkenyl group having 2 to 20 carbon atoms, one or more hydrogen atoms in these alkyl group and alkenyl group are replaced by halogen atoms; one or more —$CH_2$— in these groups may be replaced by oxygen atoms or sulfur atoms, but there is no case where oxygen atoms are adjacent; and one or more carbon atoms in these groups may be replaced by silicon atoms;

provided that when $A_5$ represents unsubstituted 1,4-phenylene in this compound, then Zd is single bond, Ze is single bond or an alkylene group having 1 to 10 carbon atoms in which alkylene group —$CH_2$— may independently be replaced by oxygen atom, sulfur atom, —$CF_2$—, —CFH—, —CH═CH—, —CF═CF—, —CF═CH—, or —C≡C—, but there is no case where oxygen atoms are adjacent, and $A_4$ is not 1,4-phenylene, and that when $A_5$ represents cyclohexylene ring and Ze represents single bond, then there is no case where $R_2$ represents an optically active monofluoroalkyl group, optically active monofluoroalkenyl group, or one of these groups in which one —$CH_2$— is replaced by oxygen atom; and each atom which constitutes this compound may be replaced by its isotope.

(2) The ester compound recited in (1) above wherein ring $A_5$ is 1,4-cyclohexylene, 1-cyclohexene-1,4-diyl, or 3-cyclohexene-1,4-diyl; one or more —$CH_2$— in these groups may each independently be replaced by oxygen atoms, sulfur atoms, —CO—, —CS—, —$SiH_2$—, —NH—, —$CF_2$—, or —CFH—, but there is no case where oxygen atoms are adjacent; hydrogen atoms which bond to carbon atoms at position 2 and position 3, respectively, in the 1-cyclohexene-1,4-diyl or 3-cyclohexene-1,4-diyl may be replaced by fluorine atoms; and both $Y_1$ and $Y_2$ are oxygen atoms in the general formula (1).

(3) The ester compound recited in (2) above wherein Ze is single bond in the general formula (1).

(4) The ester compound recited in (3) above wherein $R_2$ is a straight chain alkyl group having 1 to 5 carbon atoms in which alkyl group two or more hydrogen atoms are replaced by fluorine atoms in the general formula (1).

(5) The ester compound recited in (4) above wherein both n1 and n2 are 0, n3 is 1, both rings $A_4$ and $A_5$ are 1,4-cyclohexylene in which one or more —$CH_2$— may each independently be replaced by oxygen atoms, but there is no case where oxygen atoms are adjacent; and Zd is single bond in the general formula (1).

(6) The ester compound recited in (1) above wherein both n1 and n2 are 0, n3 is 0, and at least one of rings $A_3$, $A_4$, and $A_5$ is 1-cyclohexene-1,4-diyl or 3-cyclohexene-1,4-diyl in the general formula (1).

(7) The ester compound recited in (1) above wherein ring $A_5$ is 1,4-phenylene in which phenylene group one or more hydrogen atoms may each independently be replaced by halogen atoms, halogenated alkyl groups having 1 to 3 carbon atoms, methyl or nitro groups, and one or more —CH═ may each independently be replaced by nitrogen atoms in the general formula (1).

(8) The ester compound recited in (7) above wherein ring $A_5$ is. 1,4-phenylene in which one or more hydrogen atoms are replaced by fluorine atoms in the general formula (1).

(9) The ester compound recited in (1) above 1 wherein $R_1$ is a straight chain alkyl group having 1 to 20 carbon atoms or a straight chain alkenyl group having 2 to 20 carbon atoms; one or more hydrogen atoms in which groups may be replaced by halogen atoms, one or more —$CH_2$— in the groups may be replaced by oxygen atoms or sulfur atoms, but there is no case where oxygen atoms are adjacent; and one or more carbon atoms in the groups may be replaced by silicon atoms in the general formula (1).

(10) A liquid crystal composition comprising at least one ester compound recited in any one of (1) to (9) above.

(11) A liquid crystal composition comprising, as a first component, at least one ester compound recited in any one of (1) to (9) above, and comprising, as a second component, at least one compound selected from the group consisting of the compounds expressed by any one of the general formulas (2), (3), and (4)

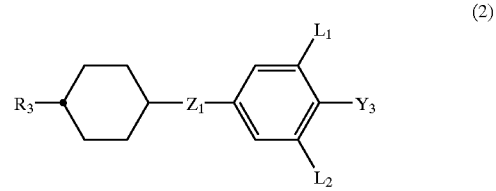

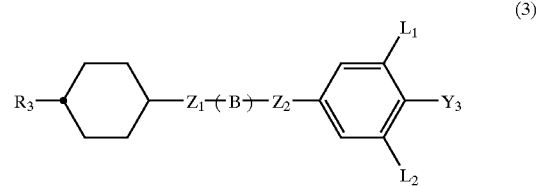

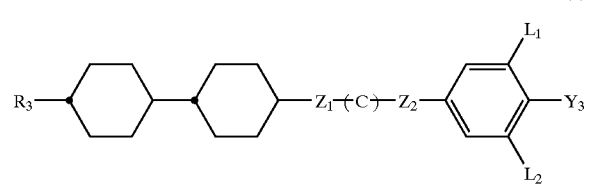

wherein $R_3$, $Y_3$, $L_1$, $L_2$, $Z_1$, and $Z_2$ may be the same or different among each of the formulas;

$R_3$ represents an alkyl group having 1 to 10 carbon atoms in which alkyl group one or not-adjacent two or more methylene groups may be replaced by oxygen atoms or —CH═CH—; and any hydrogen atom in the alkyl group may be replaced by fluorine atom;

$Y_3$ represents fluorine atom, chlorine atom, —$OCF_3$, —$OCF_2H$, —$CF_3$, —$CF_2H$, —$CFH_2$, —$OCF_2CF_2H$, or —$OCF_2CFHCF_3$;

$L_1$ and $L_2$ each independently represent hydrogen atom or fluorine atom;

$Z_1$ and $Z_2$ each independently represent —$CH_2CH_2$—, —$CH_2CH_2CH_2CH_2$—, —COO—, —$CF_2O$—, —$OCF_2$—, —CH═CH—, or single bond;

ring B represents trans-1,4-cyclohexylene or 1,3-dioxane-2,5-diyl, or 1,4-phenylene in which hydrogen atom may be replaced by fluorine atom;

ring C represents trans-1,4-cyclohexylene, or 1,4-phenylene in which hydrogen atom may be replaced by fluorine atom; and each atom which constitutes these compounds may be replaced by its isotope.

(12) A liquid crystal composition comprising, as a first component, at least one compound recited in any one of (1) to (9) above, and comprising, as a second component, at least one compound selected from the group consisting of the compounds expressed by the general formula (5) or (6)

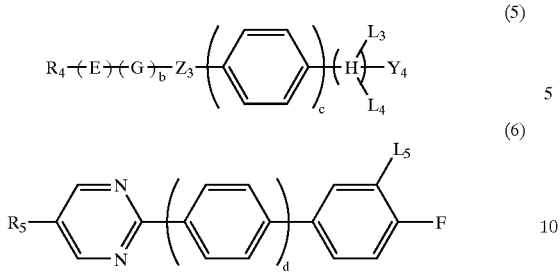

wherein $R_4$ and $R_5$ each independently represent an alkyl group having 1 to 10 carbon atoms in which alkyl group one or not-adjacent two or more methylene groups may be replaced by oxygen atoms or —CH=CH—; and hydrogen atom in the group may be replaced by fluorine atom;

$Y_4$ represents —CN or —C≡C—CN;

ring E represents trans-1,4-cyclohexylene, 1,4-phenylene, 1,3-dioxane-2,5-diyl, or pyrimidine-2,5-diyl;

ring G represents trans-1,4-cyclohexylene or pyrimidine-2,5-diyl, or 1,4-phenylene in which hydrogen atom may be replaced by fluorine atom;

ring H represents trans-1,4-cyclohexylene or 1,4-phenylene;

$Z_3$ represents —CH$_2$CH$_2$—, —COO—, or single bond;

$L_3$, $L_4$, and $L_5$ each independently represent hydrogen atom or fluorine atom;

b, c, and d are each independently 0 or 1; and each atom which constitutes these compounds may be replaced by its isotope.

(13) A liquid crystal composition comprising, as a first component, at least one compound recited in any one of (1) to (9) above, comprising, as a second component, at least one compound selected from the group consisting of the compounds expressed by any of the general formula (2), (3), and (4) described above, and comprising, as a third component, at least one compound selected from the group consisting of the compounds expressed any one of the general formulas (7), (8), and (9)

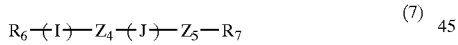

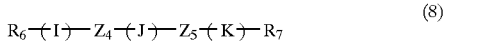

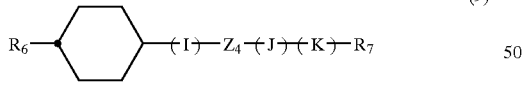

wherein $R_6$, $R_7$, I, J, and K may be the same or different among each of the formulas;

$R_6$ and $R_7$ each independently represent an alkyl group having 1 to 10 carbon atoms in which alkyl group one or not-adjacent two or more methylene groups may be replaced by oxygen atoms or —CH=CH—; and any hydrogen atom in the group may be replaced by fluorine atom;

ring I, ring J, and ring K each independently represent trans-1,4-cyclohexylene or pyrimidine-2,5-diyl, or 1,4-phenylene in which hydrogen atom may be replaced by fluorine atom;

$Z_4$ and $Z_5$ each independently represent —C≡C—, —COO—, —CH$_2$CH$_2$—, —CH=CH—, or single bond; and each atom which constitutes these compounds may be replaced by its isotope.

(14) A liquid crystal composition comprising, as a first component, at least one compound recited in any one of (1) to (9) above, comprising, as a second component, at least one compound selected from the group consisting of the compounds expressed by the general formula (5) or (6) described above, and comprising, as a third component, at least one compound selected from the group consisting of the compounds expressed by any one of the general formulas (7), (8), and (9) described above.

(15) A liquid crystal composition comprising, as a first component, at least one compound recited in any one of (1) to (9) above, comprising, as a part of a second component, at least one compound selected from the group consisting of the compounds expressed by any one of the general formulas (2), (3), and (4), comprising, as another part of the second component, at least one compound selected from the group consisting of the compounds expressed by the general formula (5) or (6) described above, and comprising, as a third component, at least one compound selected from the group consisting of the compounds expressed by any one of the general formulas (7), (8), and (9) described above.

(16) A liquid crystal composition recited in any one of (10) to (15) above in which at least one optically active compound is further comprised.

(17) A liquid crystal display device comprising a liquid crystal composition recited in any one of (10) to (16) above.

BEST MODE FOR CARRYING OUT THE INVENTION

Ester compounds of the present invention expressed by the general formula (1) have two to five rings at its core part. Also, in the compounds of the present invention, a halogen atom, halogenated alkyl group, or halogenated alkenyl group is bonded to the carbon atom of carbonyl in at least one ester group. Since the compounds of the present invention have such a specific structure as described above, the compounds which have no aromatic ring at the core part have small Δn, large Δε, low viscosity, and high voltage holding ratio; and the compounds having aromatic ring at the core part have medium or large Δn, large Δε, high clearing point, low viscosity, and high voltage holding ratio.

Such effect was achieved for the first time by the fact that the liquid crystalline compounds have a halogen atom or halogenated alkyl group bonding to the carbon atom of carbonyl in an ester group in the molecule.

By using compounds having no aromatic ring at the core part among liquid crystalline compounds expressed by the general formula (1), liquid crystal compositions which make low voltage driving and high speed response of liquid crystal display devices possible and have small Δn can be produced. By using compounds having an aromatic ring at the core part, on the other hand, liquid crystal compositions which make driving at a wide temperature range and high speed response possible, and have medium or large Δn can be produced.

Any of the groups shown as $R_1$ makes the compounds expressed by the general formula (1) develop excellent characteristics. The compounds in which $R_1$ is an alkyl group having 1 to 7 carbon atoms, alkenyl group having 2 to 7 carbon atoms, or alkenyl group wherein two fluorine atoms are directly bonded to double bond develop low viscosity.

Among those, the compounds in which $R_1$ is an alkyl group can stand active matrix driving since they develop high voltage holding ratio, and the compounds in which $R_1$ is an alkenyl group improve particularly steepness of threshold characteristics.

The compounds in which $R_1$ is a fluoroalkyl group having 1 to 7 carbon atoms are excellent in miscibility at low temperatures, and the compounds in which $R_1$ is an alkyl group wherein one $CH_2$ is replaced by oxygen atom, particularly alkoxymethyl group increase $\Delta\epsilon$ value. Any of these compounds in which $R_1$ is fluoroalkyl group or alkoxyalkyl group have high voltage holding ratio.

Any group shown as bonding groups Za to Zd in the general formula described above make the compounds which are expressed by the general formula (1) develop excellent characteristics. The compounds in which bonding groups Za to Zd are single bonds develop high clearing point, low viscosity, excellent miscibility with other liquid crystalline compounds or liquid crystal compositions at low temperatures, and high voltage holding ratio. Whereas —$CH_2CH_2$— is slightly inferior in the aspect of viscosity compared with single bond, it makes the compounds develop more excellent miscibility at low temperatures. Whereas —COO— is slightly inferior in voltage holding ratio compared with single bond, it makes the compounds develop high clearing point and large $\Delta\epsilon$ value. Besides, —$CF_2O$— makes the compounds develop low viscosity and comparatively large $\Delta\epsilon$ compared with single bond. Whereas —CH=CH— is slightly inferior in voltage holding ratio compared with single bond, it makes the compounds develop low viscosity and steep threshold characteristics.

Any group shown as bonding group Ze in the general formula (1) makes the compounds develop excellent characteristics. Particularly, when Ze is single bond, it makes the compounds develop high clearing point, low viscosity, excellent miscibility with other liquid crystalline compounds or liquid crystal compositions at low temperatures, and high voltage holding ratio, and when Ze is —$CH_2CH_2$—, it makes the compounds develop excellent miscibility at low temperatures whereas it is slightly inferior in the aspect of viscosity compared with single bond.

In the general formula (1), n1 to n3 are each independently 0 or 1 provided that $n1 \leq n2 \leq n3$. As specific combination of n1, n2, and n3, while four kind of combinations of (n1, n2, n3)=(0, 0, 0), (0, 0, 1), (0, 1, 1), or (1, 1, 1) can be mentioned, the compounds of (n1, n2, n3)=(0, 0, 0) have low viscosity and are excellent in miscibility at low temperatures, the compounds of (n1, n2, n3)=(0, 0, 1) have comparatively high clearing point and comparatively low viscosity, and the compounds of (n1, n2, n3)=(0, 1, 1) have high clearing point.

While any terminal substituent $R_2$ in the general formula (1) described above makes the compounds develop excellent characteristics, particularly $CF_3$ and $CF_2CF_3$ make them develop large $\Delta\epsilon$ and low viscosity, and $CF_2H$ makes the compounds develop high clearing point whereas it is slightly inferior in $\Delta\epsilon$ compared with $CF_3$.

While various type of structures can be applied at the core part in the general formula (1) described above, any of them make the compounds develop excellent characteristics. Among them, some examples are shown in following general formulas (1-1) to (1-32):

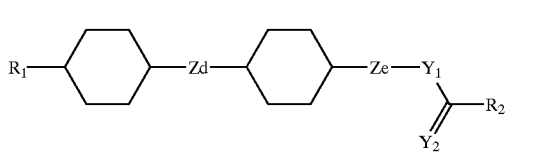

(1-1)

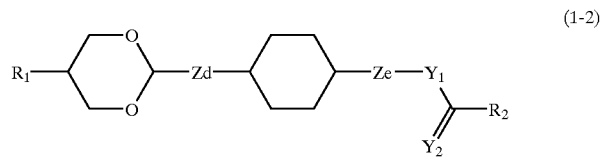

(1-2)

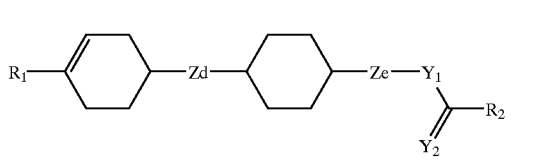

(1-3)

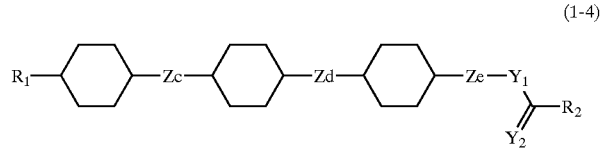

(1-4)

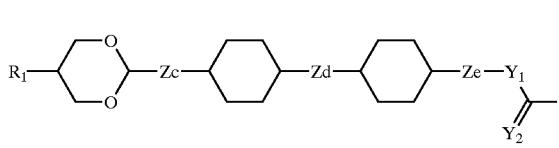

(1-5)

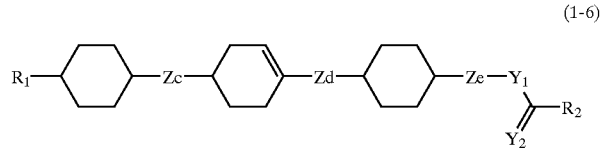

(1-6)

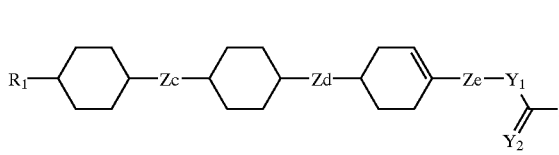

(1-7)

(1-8)

-continued
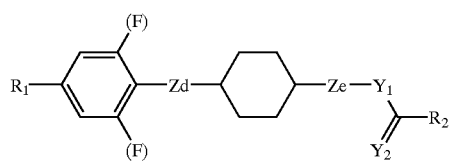
(1-9)
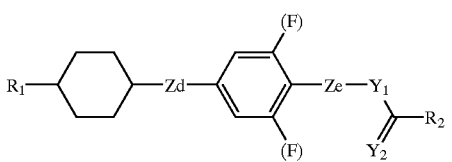
(1-10)
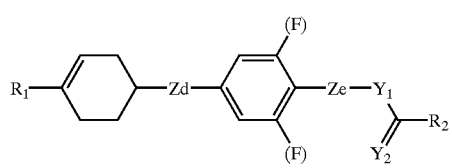
(1-11)
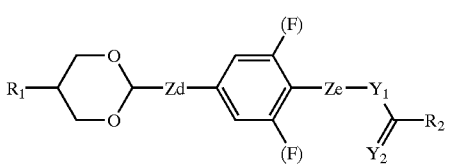
(1-12)
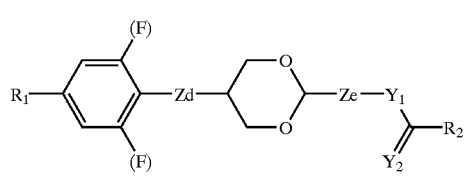
(1-13)
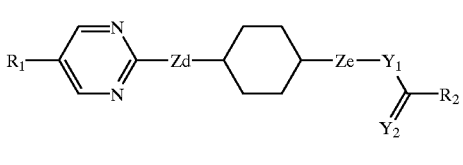
(1-14)
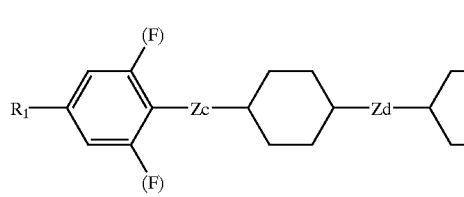
(1-15)
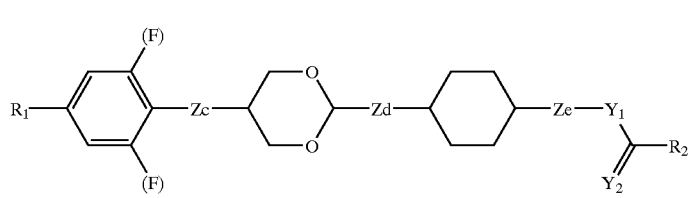
(1-16)
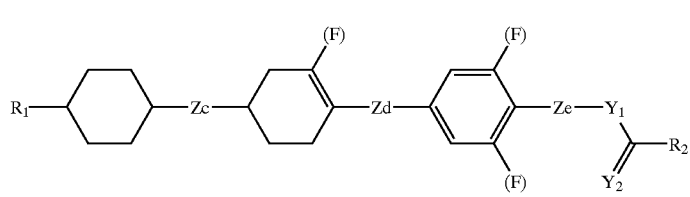
(1-17)
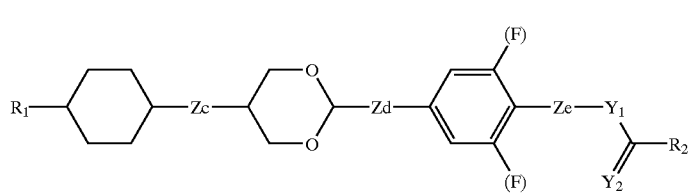
(1-18)
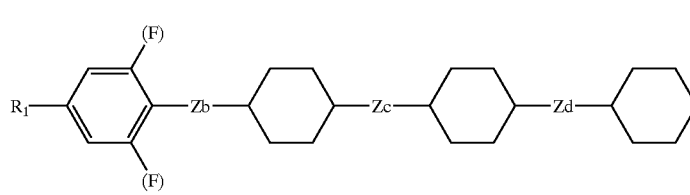
(1-19)
(1-20)

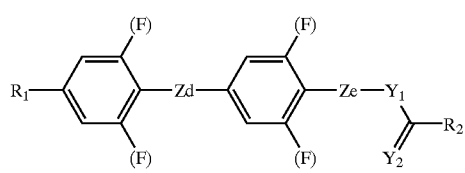 (1-21)
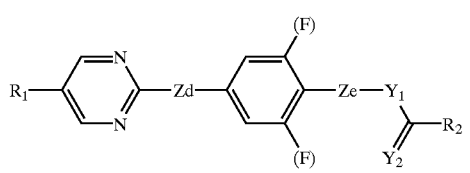 (1-22)
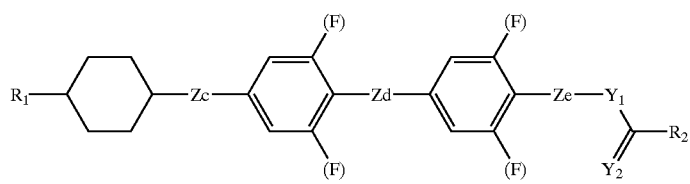 (1-23)
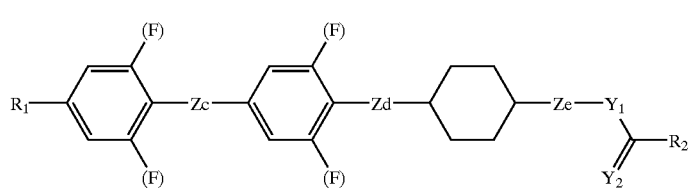 (1-24)
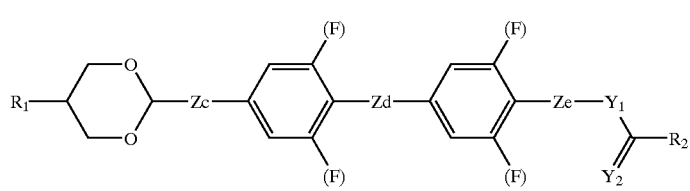 (1-25)
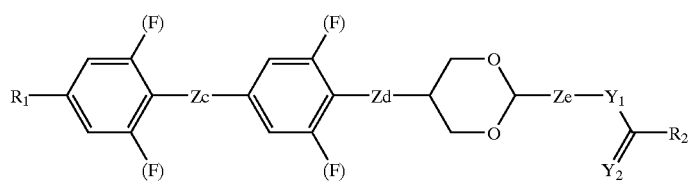 (1-26)
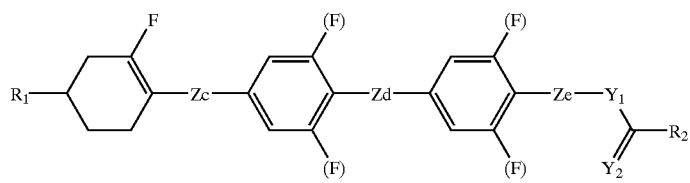 (1-27)
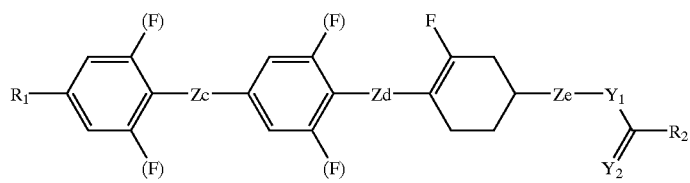 (1-28)
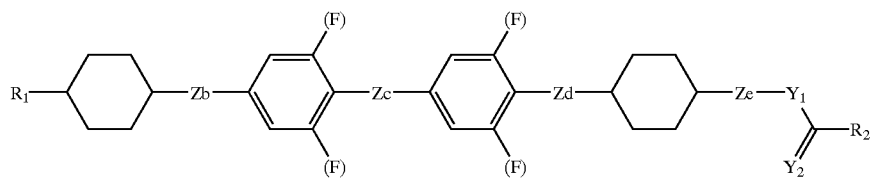 (1-29)

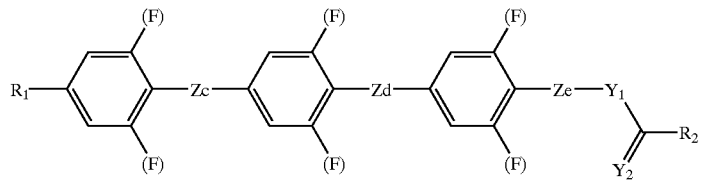

(1-30)

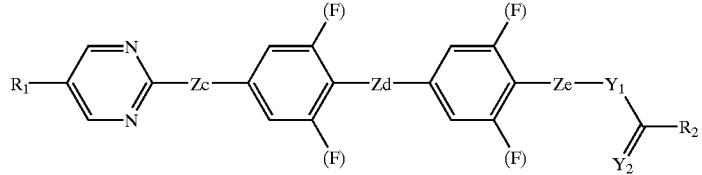

(1-31)

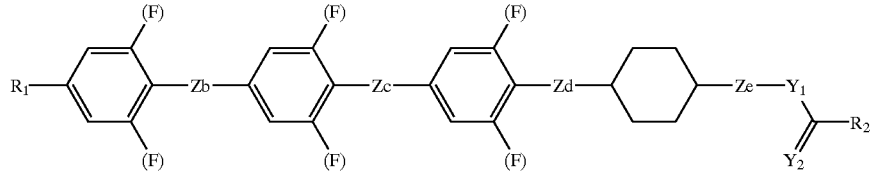

(1-32)

Among the compounds described above, the compounds expressed by one of the general formulas (1-1) to (1-8) have small Δn. The compounds in which the core part is formed only cyclohexane rings like the compounds of the general formula (1-1) or (1-4) have low viscosity, and the compounds having dioxane ring at the core part like the compounds of the general formulas (1-2), (1-5), or (1-8) have large Δε. Further, the compounds having cyclohexene ring like those of the general formulas (1-3), (1-6), (1-7), or (1-8) are excellent in miscibility at low temperatures.

Among the compounds described above, the compounds expressed by one of the general formulas (1-9) to (1-20) have medium extent of Δn, and Δε value of the compounds becomes larger as the number of fluorine atoms bonded to benzene ring increases. The compounds having pyrimidine ring or dioxane ring at the core part like the compounds of the general formula (1-12), (1-13), (1-14), (1-16), (1-18), or (1-20) have large Δε, the compounds having cyclohexene ring like the compounds of the general formula (1-11) are excellent in miscibility at low temperatures, and the compounds having 2-fluorocyclohexene ring like the compounds of the general formula (1-17) have a wide temperature range of nematic phase.

Among the compounds described above, the compounds of one of the general formulas (1-21) to (1-32) have large Δn; Δε of the compounds becomes larger as the number of fluorine atom bonded to benzene ring increases; the compounds having pyrimidine ring or dioxane ring have large Δε; the compounds having cyclohexene ring are excellent in miscibility at low temperatures; and the compounds having 2-fluorocyclohexene ring exhibit nematic phase at a wide temperature range.

As described above, any of the compounds of the present invention have a halogen atom, halogenated alkyl group, or halogenated alkenyl group bonded to the carbon atom of carbonyl in at least one ester group, and have such excellent features that the compounds of the present invention have larger Δε value and lower viscosity while having the same extent of Δn compared with conventional compounds having small Δn, and that the compounds of the present invention have higher clearing point and low viscosity while having the same extent of Δn compared with conventional compounds having medium or large Δn.

In the compounds of the present invention, each atom which constitutes the compounds may be replaced by its isotope, and characteristics of the compounds are not changed by such replacement.

While the compounds of the present invention are suitable as a component of liquid crystal compositions particularly for TFT mode, the compounds are useful as a component of the liquid crystal compositions even for other uses, for example, for TN mode, guest-host mode, polymer dispersion mode, dynamic scattering mode, STN mode, IPS mode, OCB mode,or R-OCB mode, and further can be used as a compound for forming ferroelectric liquid crystal compositions or antiferroelectric liquid crystal compositions.

Liquid crystal compositions provided according to the present invention comprise, as a first component, at least one liquid crystalline compound expressed by the general formula (1).

The content of the compound expressed by the general formula (1) in the liquid crystal compositions of the present invention is necessary to be 0.1 to 99.9% by weight based on the amount of liquid crystal composition to develop excellent characteristics, and the content is preferably 1 to 50% by weight and more desirably 3 to 20% by weight.

While the liquid crystal compositions of the present invention may comprise only the first component described above, the compositions in which at least one compound selected from the group consisting of the compounds expressed by one of the general formulas (2), (3), and (4) (hereinafter referred to as second component A) described above and/or at least one compound selected from the group consisting of the compounds expressed by the general formula (5) or (6) (hereinafter referred to as second component B) described above is added as a second component, and at least one compound selected from the group consisting of the compounds expressed by one of the general formulas (7), (8), and (9) is further added as a third component, in addition to the first component are preferable. Still further, an optically active compound and known compounds for the purpose of adjusting threshold voltage, temperature range of liquid crystal phase, Δε, Δn, viscosity, and the like can be added as other component.

Among the second component A described above, the compounds expressed by one of the general formulas (2-1) to (2-9) can be mentioned as preferable examples of the compounds expressed by the general formula (2), the compounds expressed by one of the general formulas (3-1) to (3-69) as preferable examples of the compounds expressed by the general formula (3), and the compounds expressed by one of the general formulas (4-1) to (4-24) as preferable examples of the compounds expressed by the general formula (4), respectively.

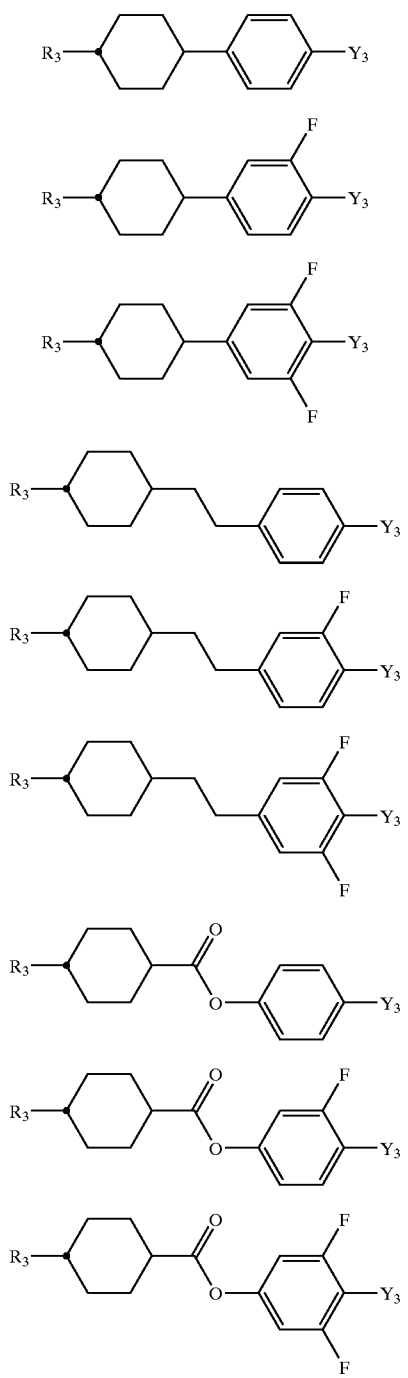

-continued

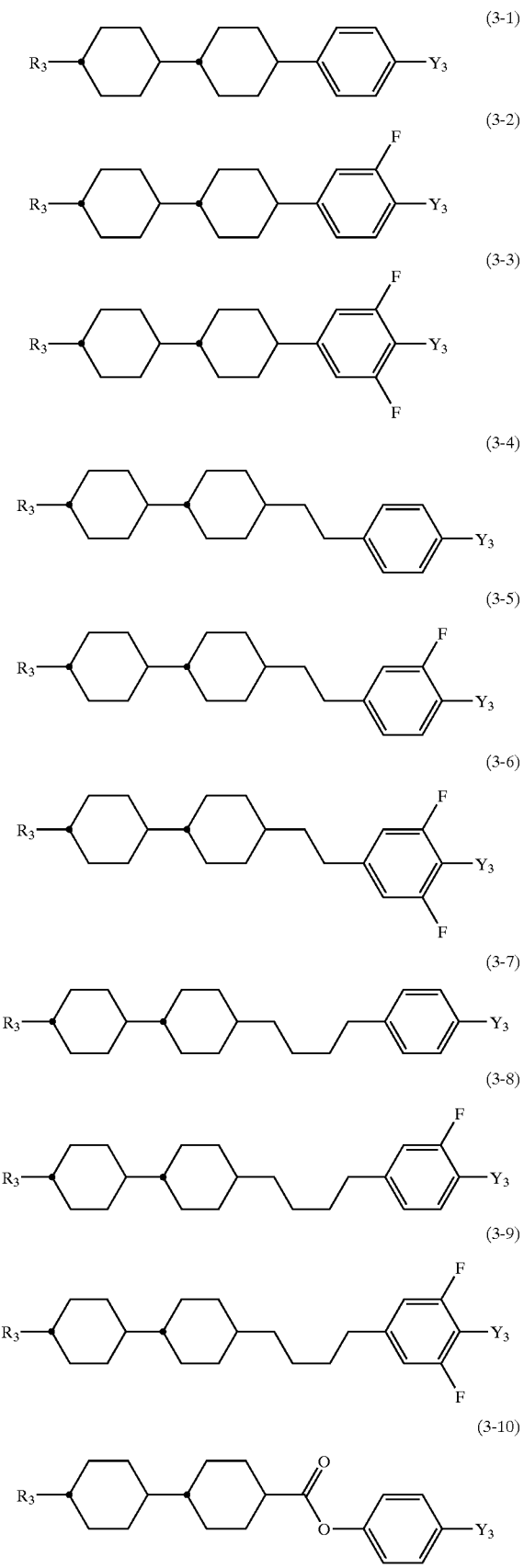

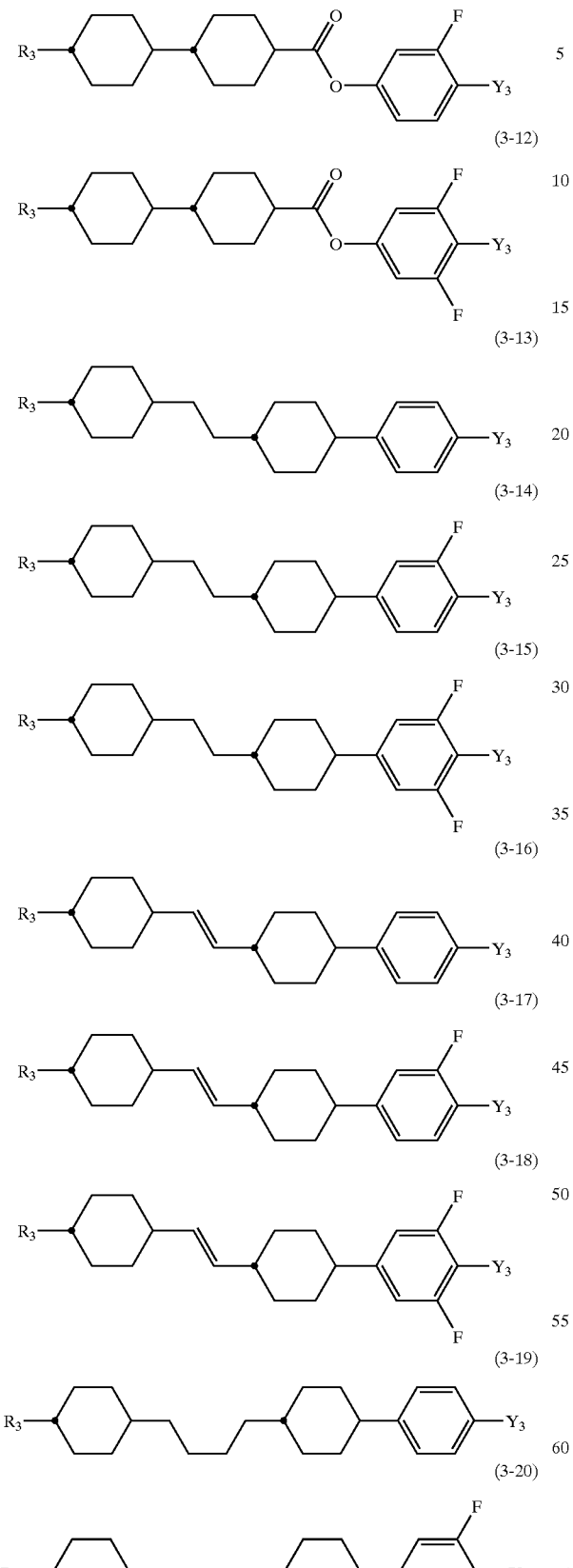
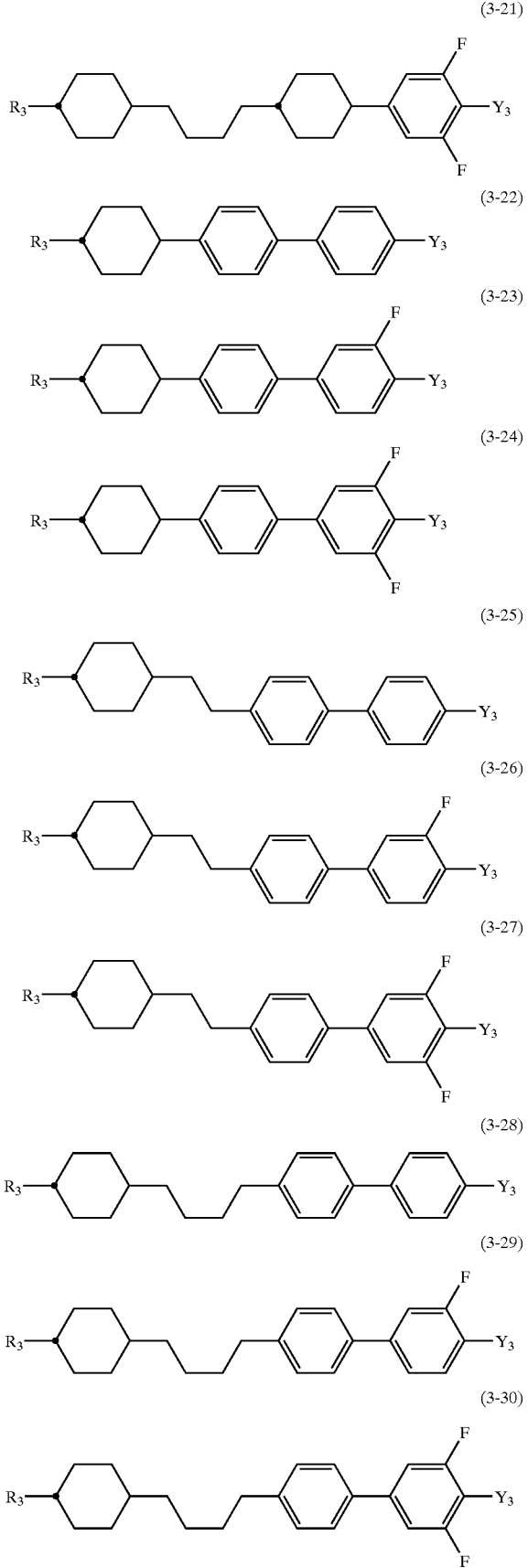

-continued
(3-31) 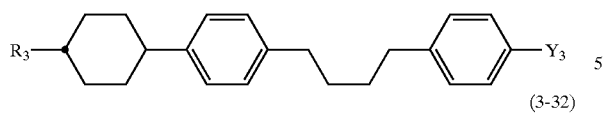
(3-32) 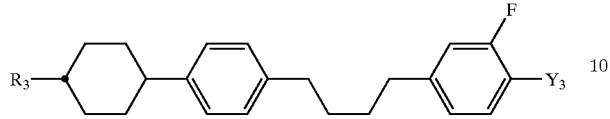
(3-33) 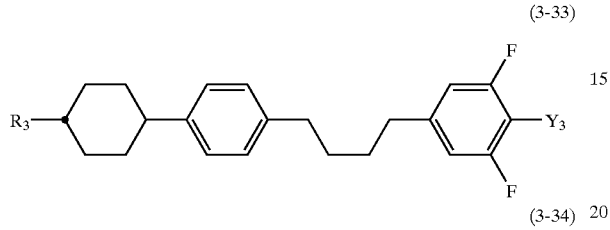
(3-34) 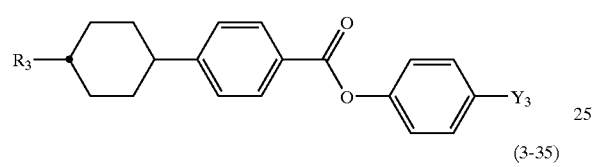
(3-35) 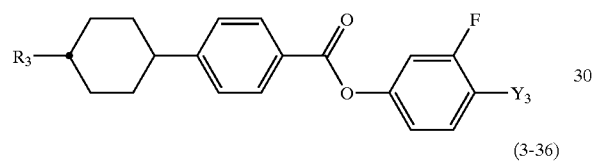
(3-36) 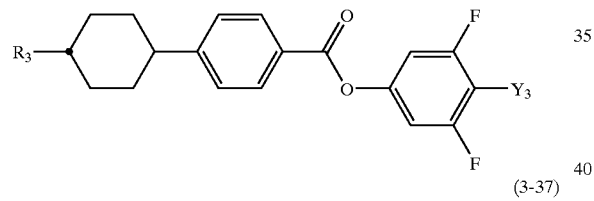
(3-37) 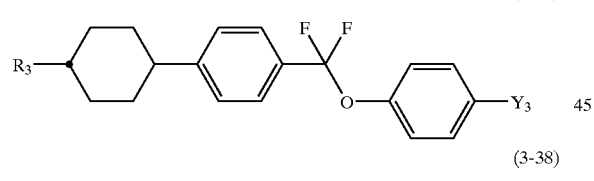
(3-38) 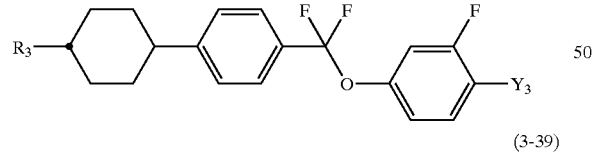
(3-39) 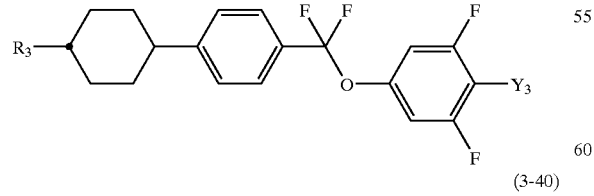
(3-40) 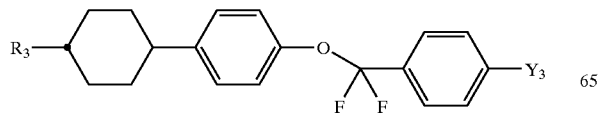
-continued
(3-41) 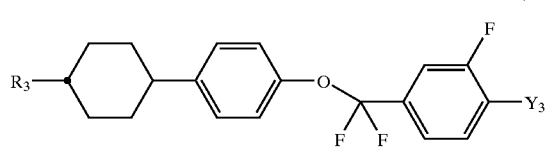
(3-42) 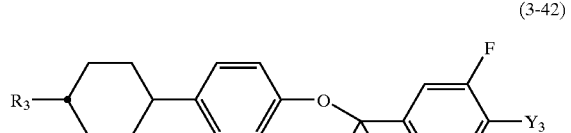
(3-43) 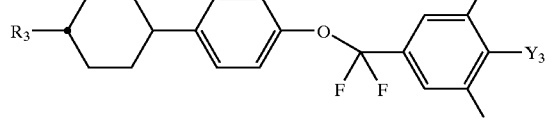
(3-44) 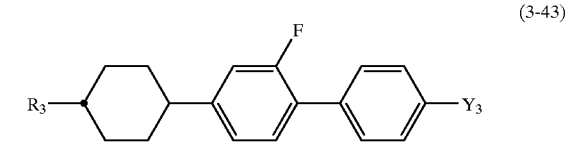
(3-45) 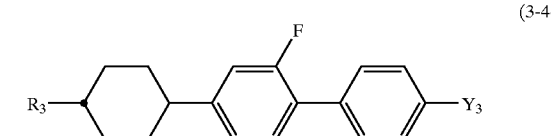
(3-46) 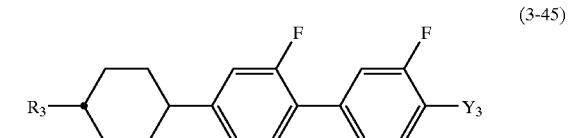
(3-47) 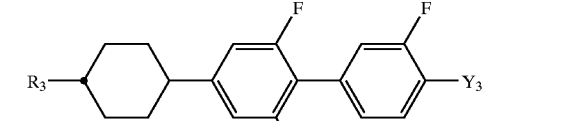
(3-48) 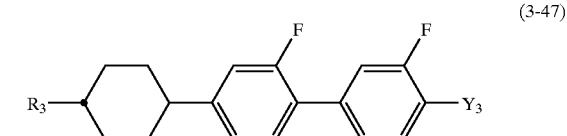
(3-49) 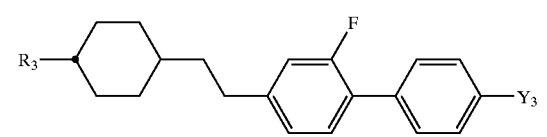

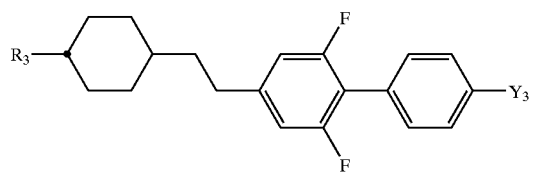
(3-50)
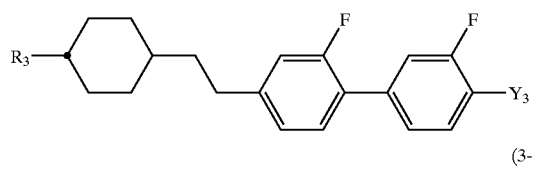
(3-51)
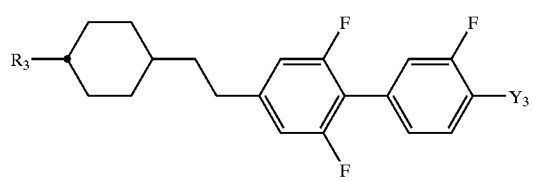
(3-52)
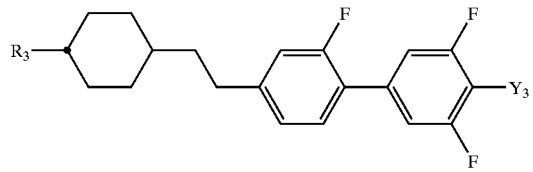
(3-53)
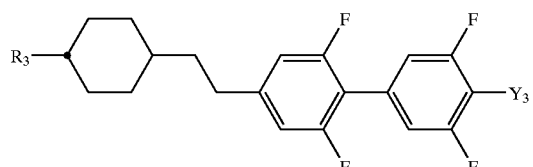
(3-54)
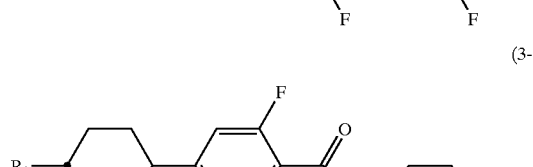
(3-55)
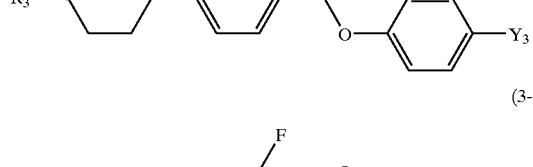
(3-56)
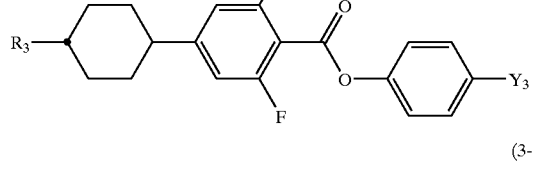
(3-57)
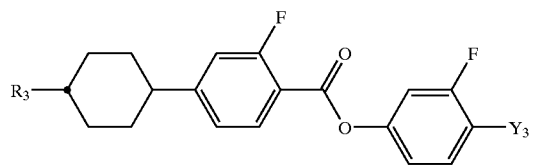
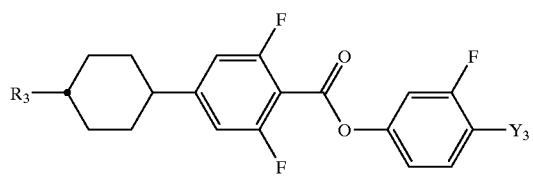
(3-58)
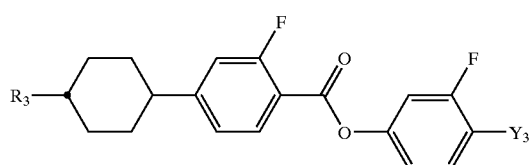
(3-59)
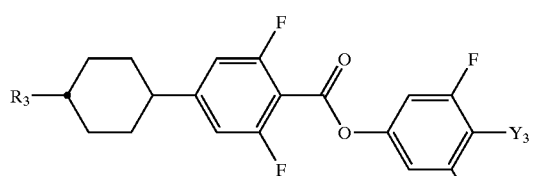
(3-60)
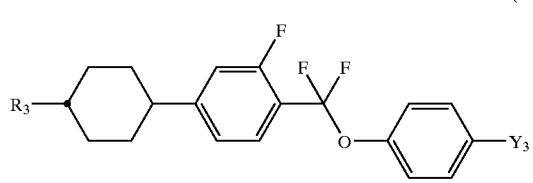
(3-61)
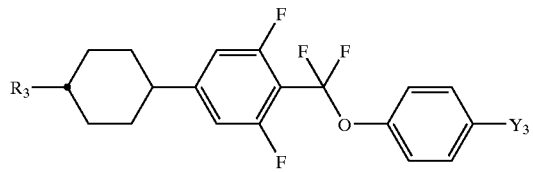
(3-62)
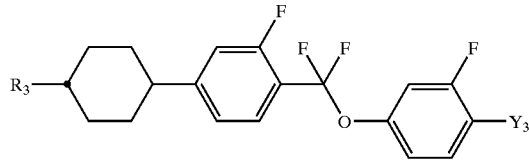
(3-63)
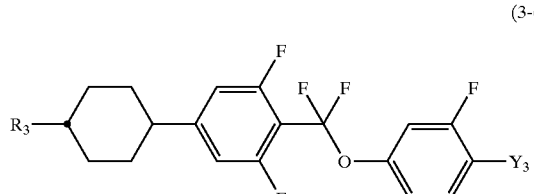
(3-64)

(3-65) 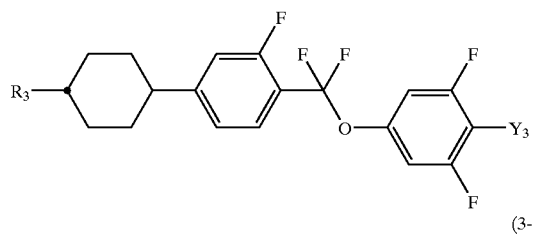
(3-66) 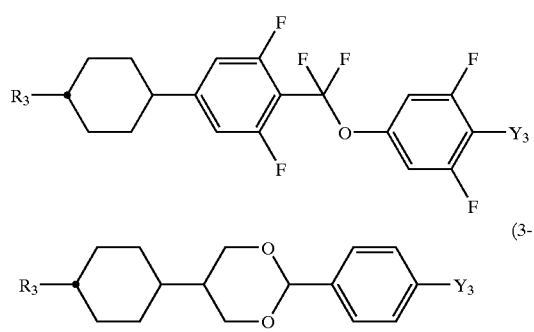
(3-67)
(3-68) 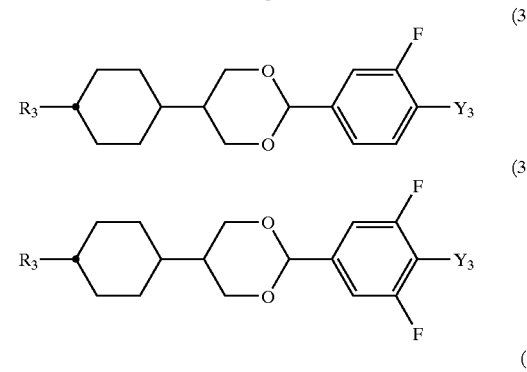
(3-69)
(4-1) 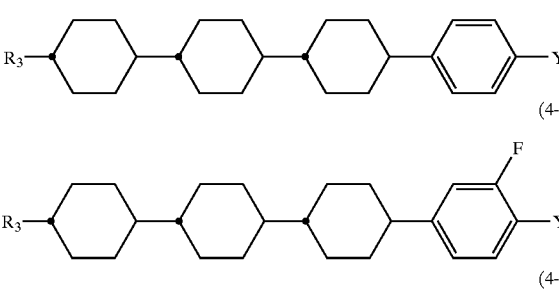
(4-2)
(4-3)
(4-4) 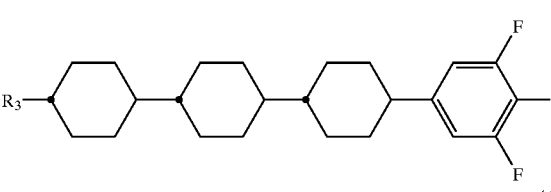
(4-5) 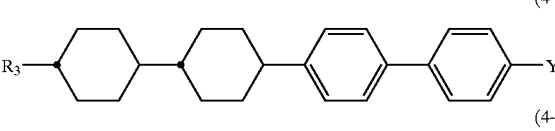
(4-6) 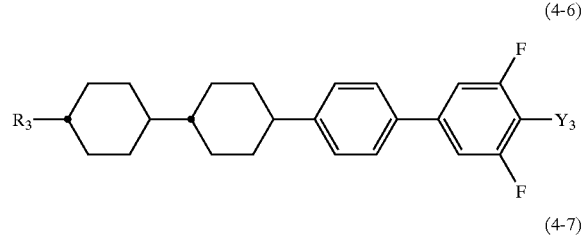
(4-7)
(4-8) 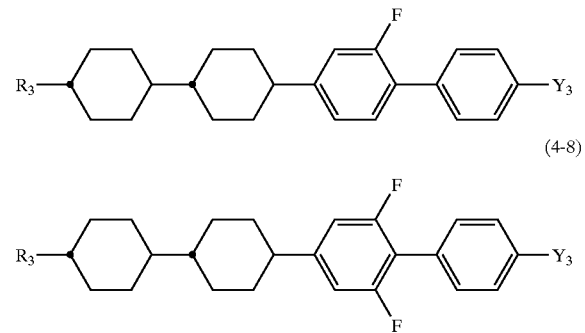
(4-9)
(4-10) 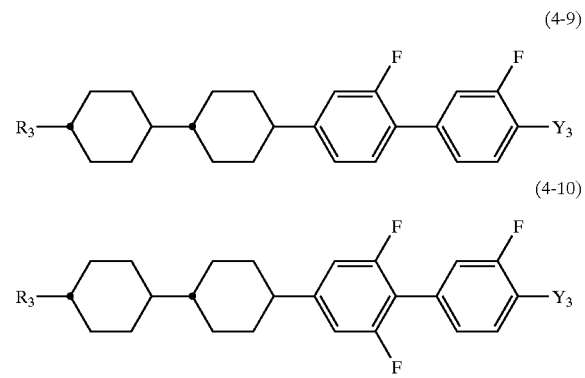
(4-11)
(4-12) 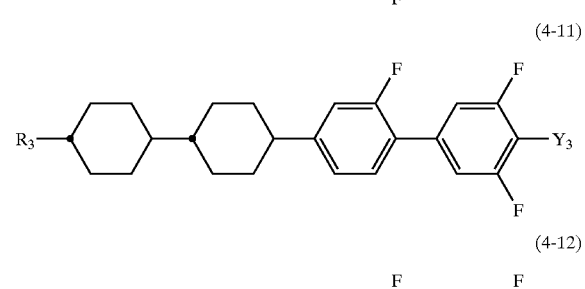
(4-13) 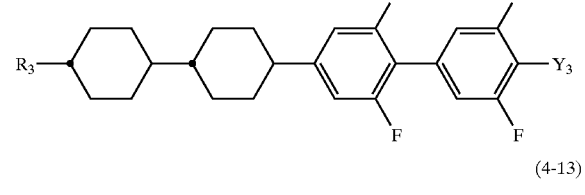
(4-14) 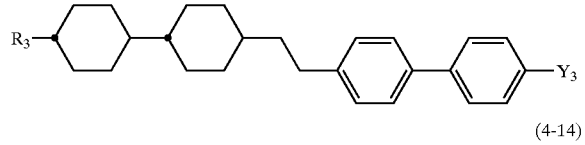

(4-15)
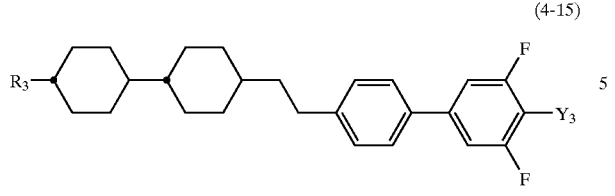

(4-16)

(4-17)
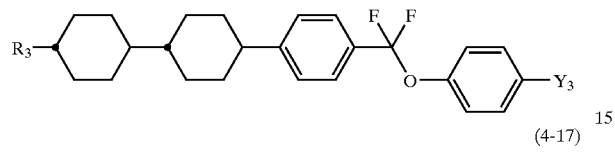

(4-18)

(4-19)
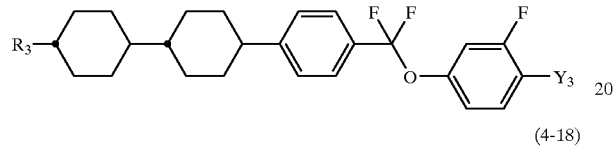

(4-20)
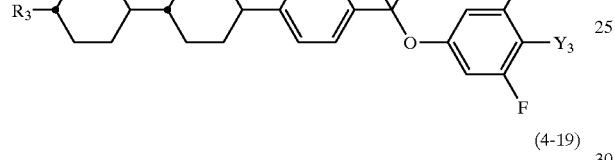

(4-21)
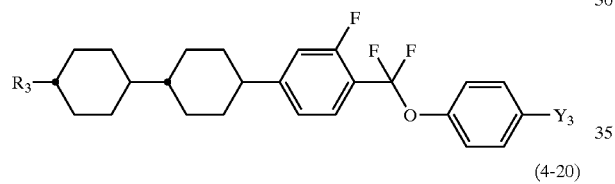

(4-22)
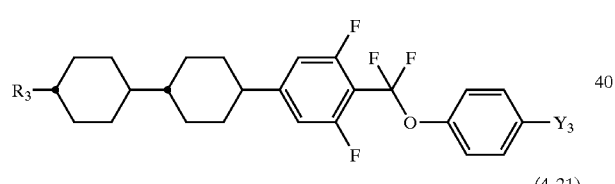

(4-23)
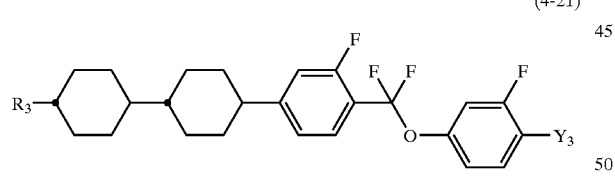

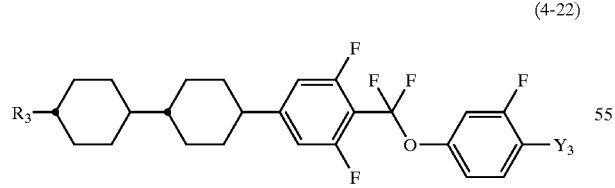

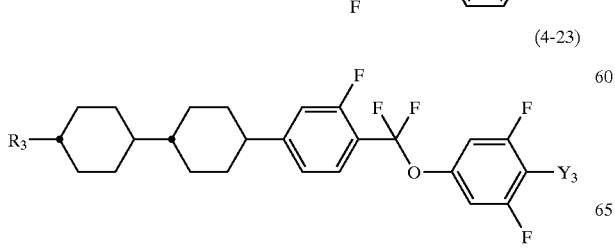

(4-24)
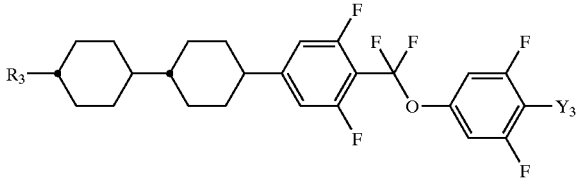

wherein $R_3$ and $Y_3$ have the same meaning as described above.

The compounds expressed by one of these general formulas (2) to (4) have positive $\Delta\epsilon$, are excellent in thermal stability and chemical stability, and are useful when liquid crystal compositions for TFT mode of which high reliability such that voltage holding ratio is high (specific resistance is large) is required are produced.

When liquid crystal compositions for TFT mode are produced, the content of the compound expressed by one of the general formulas (2) to (4) is suitably in the range of 1 to 99% by weight based on the total amount of liquid crystal composition, and the content is preferably 10 to 97% by weight and more desirably 40 to 95% by weight. At that time, the compounds expressed by one of the general formulas (7) to (9) may be used together.

While the compounds expressed by one of the general formulas (2) to (4) can be used even when liquid crystal compositions for STN mode or TN mode are produced, their content at that time is preferably less than 50% by weight based on the total amount of liquid crystal composition since the effect of the compounds of lowering threshold voltage of liquid crystal compositions is small.

Among the second component B, the compounds expressed by one of the general formulas (5-1) to (5-40) can be mentioned as preferable examples of the compounds expressed by the general formula (5), and the compounds expressed by one of the general formulas (6-1) to (6-3) as preferable examples of the general formula (6), respectively.

(5-1)
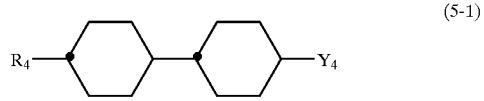

(5-2)

(5-3)

(5-4)
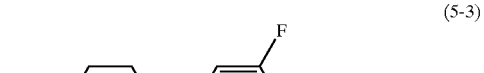

(5-5)
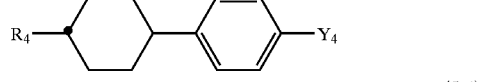

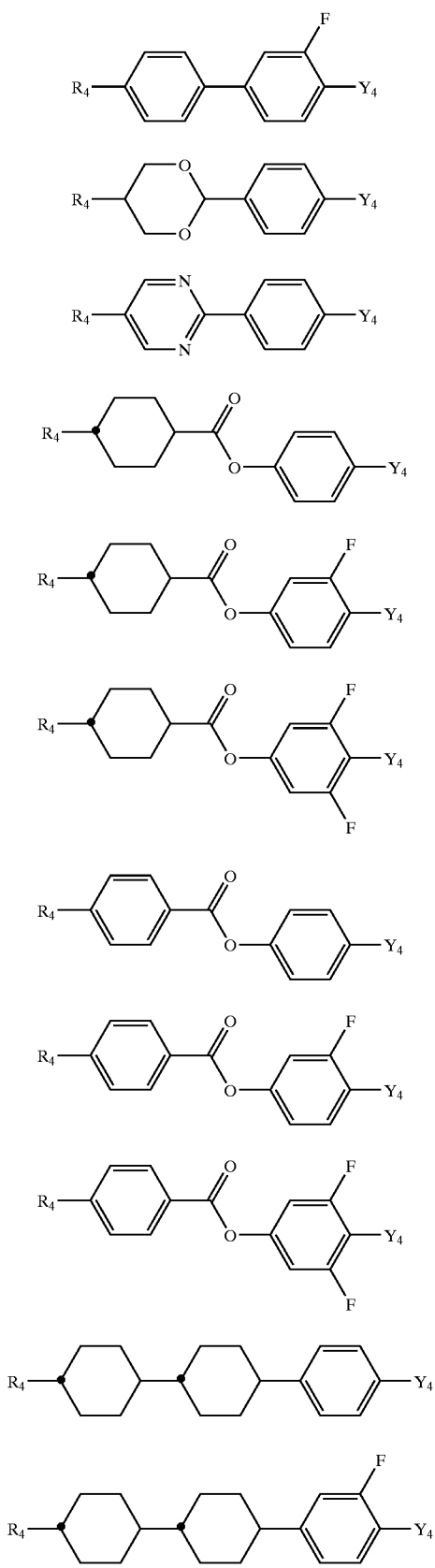
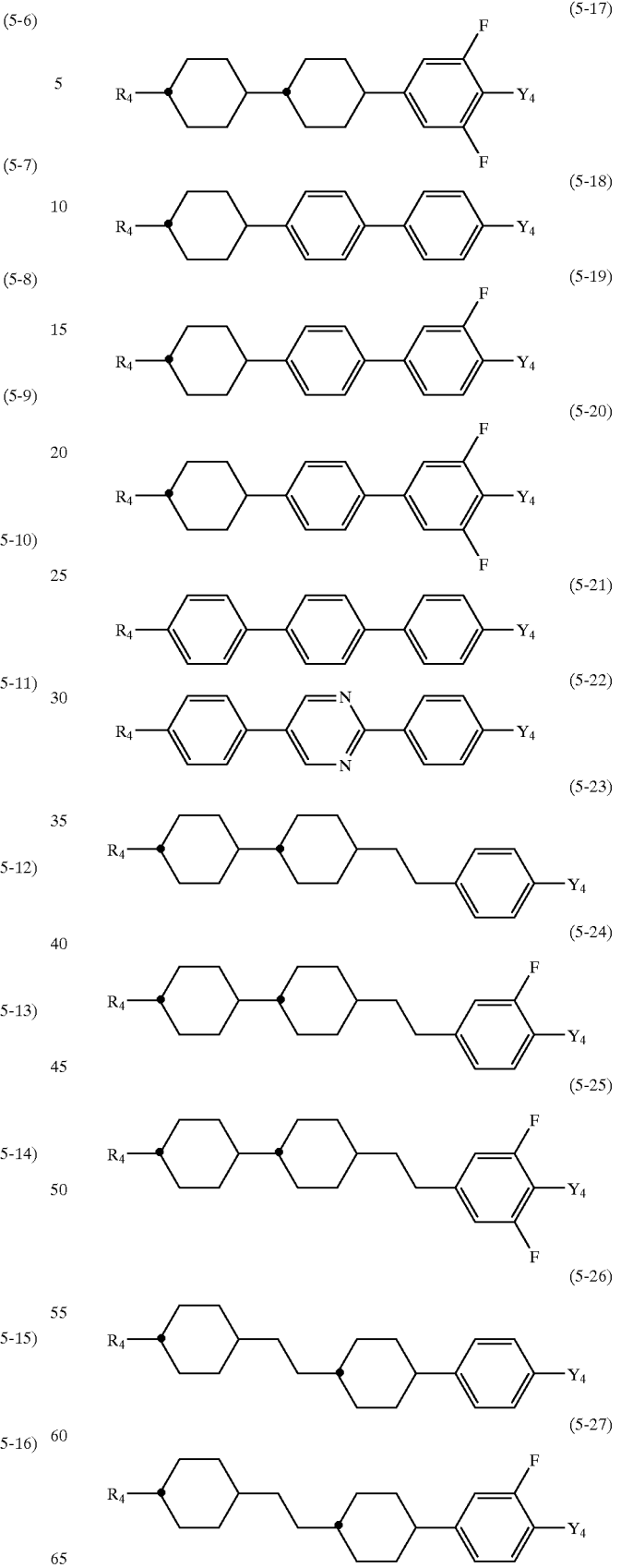

(5-28) 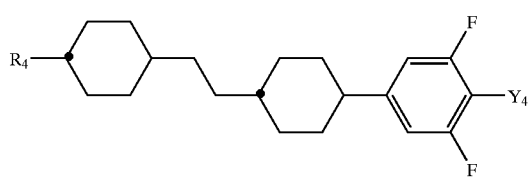

(5-29) 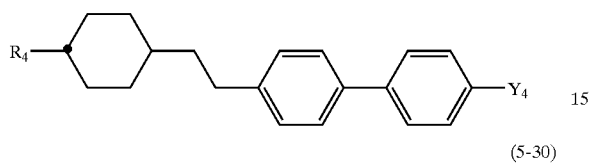

(5-30) 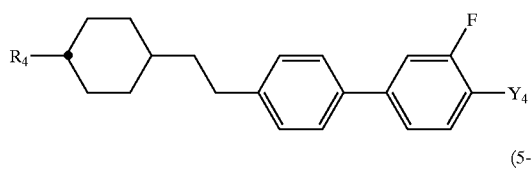

(5-31) 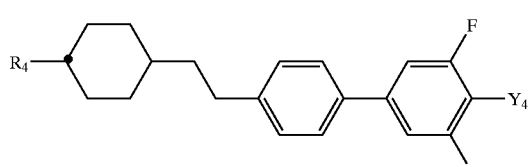

(5-32) 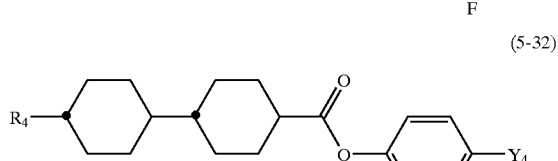

(5-33) 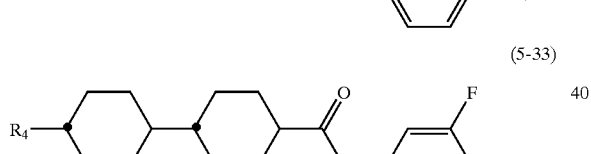

(5-34) 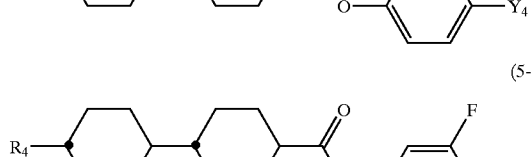

(5-35) 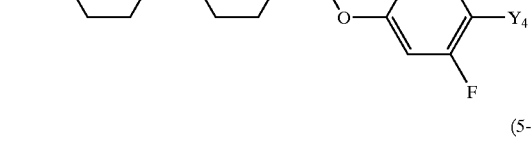

(5-36) 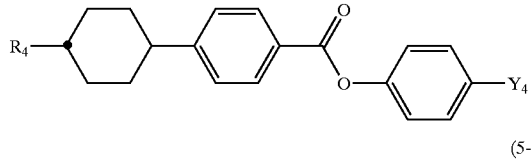

(5-37) 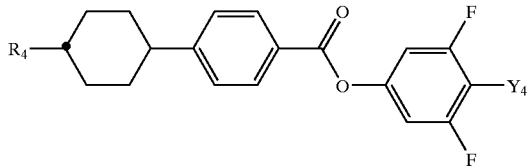

(5-38) 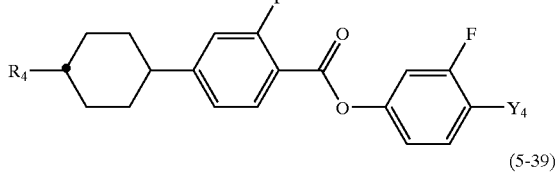

(5-39) 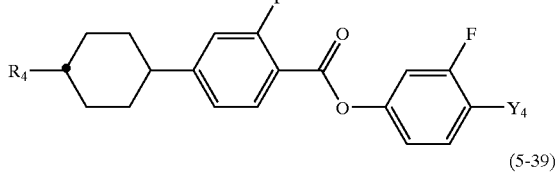

(5-40) 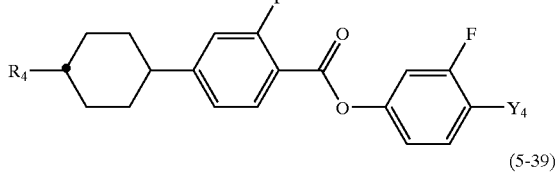

(6-1) 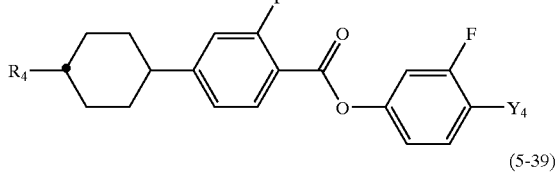

(6-2) 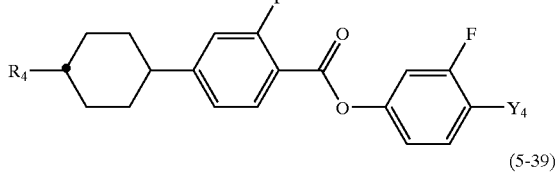

(6-3) 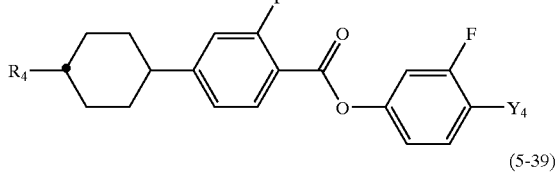

wherein $R_4$, $R_5$, and $Y_4$ have the same meaning as described above.

These compounds expressed by the general formula (5) or (6) have positive and large $\Delta\epsilon$ value, and are used particularly for the purpose of lowering threshold voltage of liquid crystal compositions. Also, they are used for the purpose of improving the steepness of threshold characteristics of liquid crystal compositions for STN mode or TN mode including for the purpose of adjusting $\Delta N$ and widening nematic range such as raising clearing point of liquid crystal compositions, and are useful compounds when liquid crystal compositions particularly for STN mode or TN mode are produced.

The compounds can lower threshold voltage of liquid crystal compositions according as their content is increased, but, on the other hand, they bring about increase of viscosity. Therefore, it becomes more advantageous for driving the devices at a low voltage as their content increases, so far as viscosity of liquid crystal compositions satisfies required characteristics.

From such circumstances, when liquid crystal compositions for STN mode or TN mode are produced, the content of the compounds of the general formula (5) or (6) is suitably in the range of 0.1 to 99.9% by weight, preferably 10 to 97% by weight, and more desirably 40 to 95% by weight based on the total amount of liquid crystal composition.

Among the third component described above, the compounds expressed by one of the general formulas (7-1) to (7-11) can be mentioned as preferable examples of the compounds expressed by the general formula (7), the compounds expressed by one of the general formulas (8-1) to (8-18) as preferable examples of the general formula (8), and the compounds expressed by one of the general formulas (9-1) to (9-6) as preferable examples of the general formula (9), respectively.

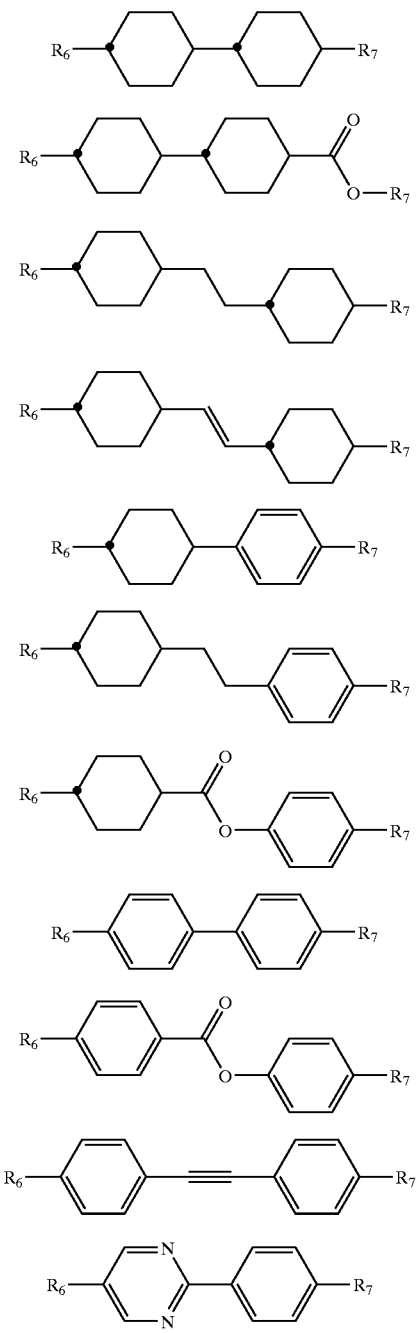

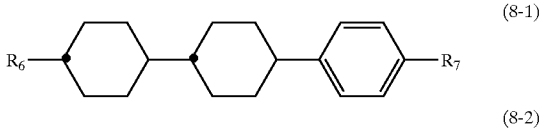
(8-1)

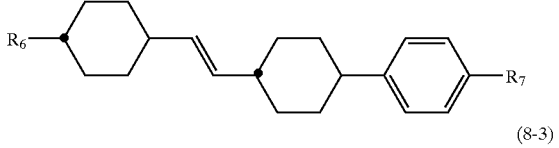
(8-2)

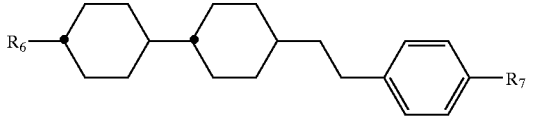
(8-3)

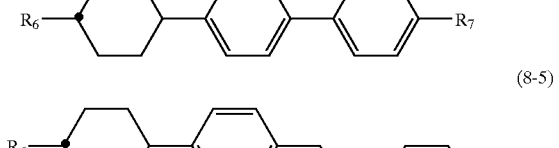
(8-4)

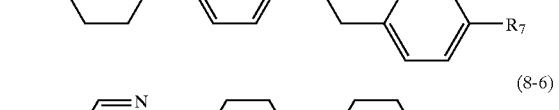
(8-5)

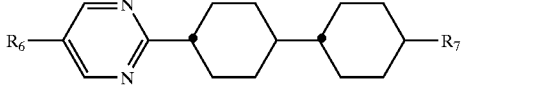
(8-6)

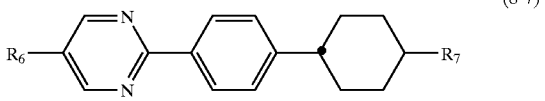
(8-7)

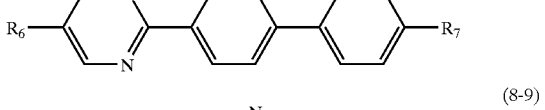
(8-8)

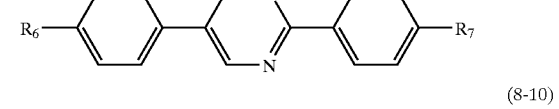
(8-9)

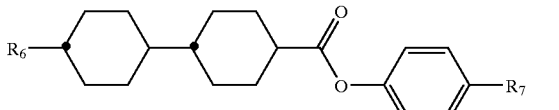
(8-10)

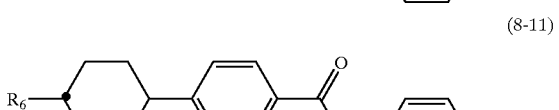
(8-11)

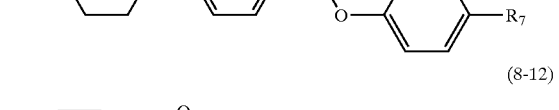
(8-12)

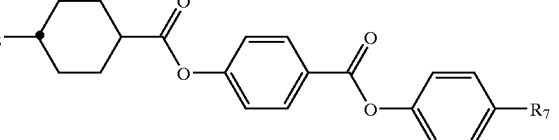

(8-13)
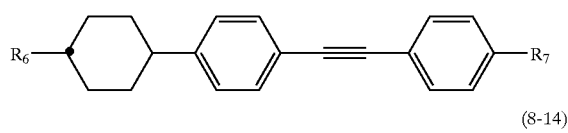

(8-14)
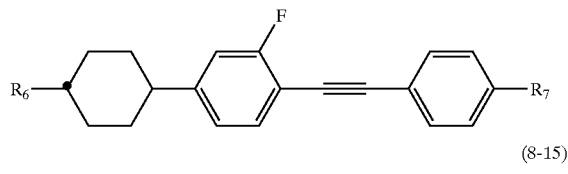

(8-15)
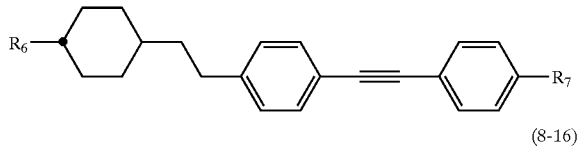

(8-16)
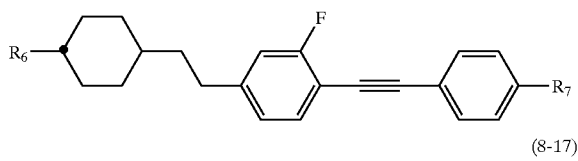

(8-17)
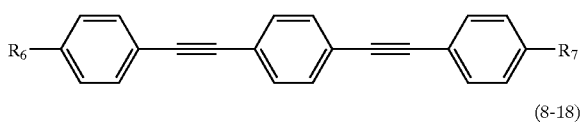

(8-18)
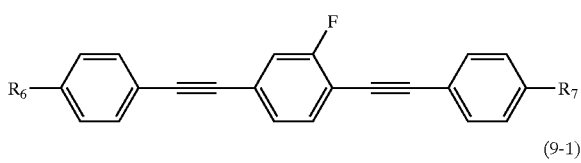

(9-1)
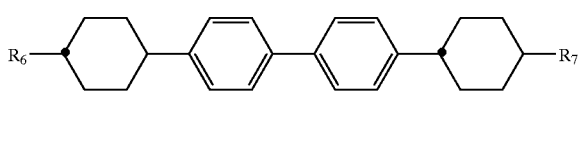

(9-2)
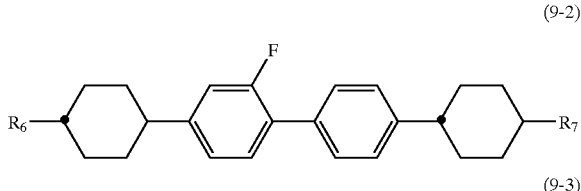

(9-3)
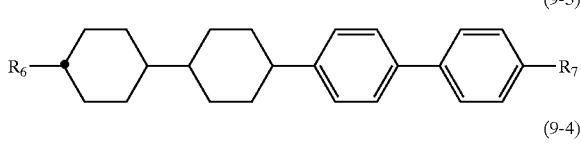

(9-4)
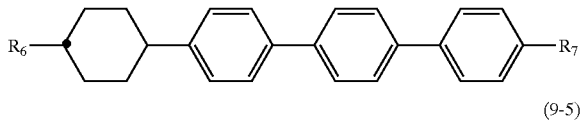

(9-5)
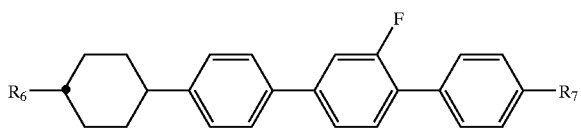

(9-6)
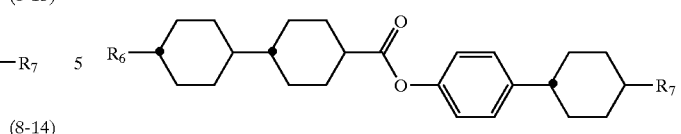

wherein $R_6$ and $R_7$ have the same meaning as described above.

The compounds expressed by one of the general formulas (7) to (9) have a small absolute Δε value close to zero. Among them, the compounds expressed by the general formula (7) are used principally for the purpose of adjusting viscosity or adjusting Δn of liquid crystal compositions, the compounds expressed by the general formula (8) or (9) are used for the purpose of widening nematic range such as raising clearing point, and adjusting Δn of liquid crystal compositions.

These compounds raise threshold voltage of liquid crystal compositions according as their content is increased, but, on the other hand, they reduce viscosity. Thus, their content is desirably high so far as threshold voltage of liquid crystal compositions satisfies required characteristics.

From such circumstances, when liquid crystal compositions for TFT mode are produced, the content of the compounds expressed by one of the general formulas (7) to (9) is suitably less than 40% by weight, and preferably less than 35% by weight based on the total amount of liquid crystal composition. On the other hand, when liquid crystal compositions for STN mode or TN mode are produced, the content of the compounds expressed by one of the general formulas (7) to (9) is suitably less than 70% by weight and preferably less than 60% by weight based on the total amount of liquid crystal composition.

Excepting such a specific case as liquid crystal compositions for OCB (Optically Compensated Birefringence) mode, an optically active compound is generally added to the liquid crystal compositions for the purpose of inducing helical structure of liquid crystal compositions to adjust required twist angle and to prevent reverse twist. Optical active compounds added to the liquid crystal compositions of the present invention are not specifically restricted so far as the purposes described above are achieved. While they can be selected from a wide range of known optically active compounds, the optically active compounds expressed by one of the following formulas (Op-1) to (Op-8) can preferably be mentioned.

(Op-1)
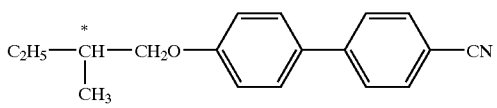

(Op-2)
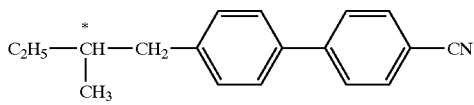

(Op-3)
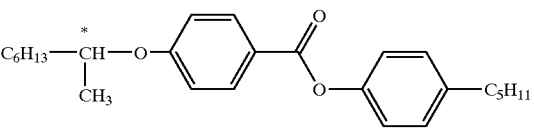

-continued (Op-4)
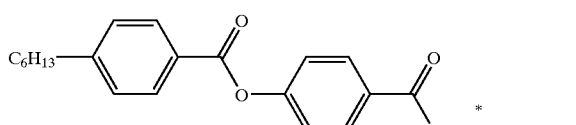

(Op-5)
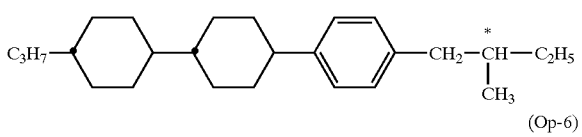

(Op-6)
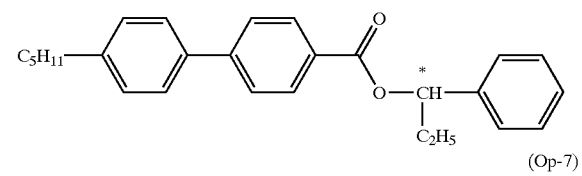

(Op-7)
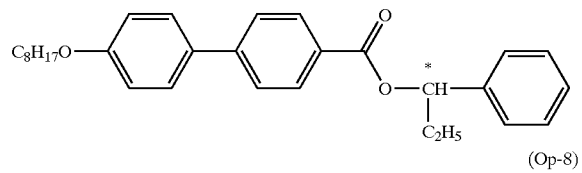

(Op-8)
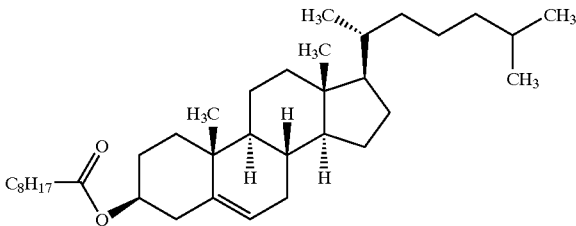

By adding one of these optically active compounds, the pitch of the twist of liquid crystal compositions can be adjusted. Pitch of the twist is preferably adjusted in the range of 40 to 200 μm in the case of liquid crystal compositions for TFT mode or TN mode, preferably adjusted in the range of 6 to 20 μm in the case of liquid crystal compositions for STN mode, and preferably adjusted in the range of 1.5 to 4 μm in the case of liquid crystal compositions for bistable TN mode.

At this time, two or more kind of optically active compounds may be added for the purpose of adjusting the dependency of the pitch length on temperature.

The liquid crystal compositions provided according to the present invention can be produced by methods which are conventional by themselves, for instance, by a method in which various components are dissolved in one another at a high temperature.

Further, the liquid crystal compositions of the present invention can be used as ones for guest-host (GH) mode by adding a dichroic dye such as merocyanine type, styryl type, azo type, azomethine type, azoxy type, quinophthalone type, anthraquinone type, and tetrazine type thereto. Furthermore, the liquid crystal compositions can be used as NCAP which is prepared by the microencapsulation of a nematic liquid crystal, or as liquid crystal compositions for polymer dispersed liquid crystal display devices (PDLCD) represented by polymer net work liquid crystal display devices (PNLCD) prepared by forming a polymer of three-dimensional reticulated structure in a liquid crystal. Still further, the liquid crystal compositions of the present invention can be used as ones for electrically controlled birefringence (ECB) mode or dynamic scattering (DS) mode.

As examples of the nematic liquid crystal compositions of the present invention, the following composition examples 1 through 41 can be shown.

Each of the compounds in the following composition examples is designated by making groups shown in each of the columns of left side terminal group, bonding group, ring structure, and right side terminal group correspond to symbols shown in each of their columns according to the definitions shown in Table 1 described below. Particularly, positions of deuteriums on cyclohexane ring are indicated by the numerals added at right side shoulder of L in Table 2, and designated like examples shown in the Table together with symbol D indicating the deuterium.

Compounds shown in the compositions examples and those in the examples described below to both of which the same Compound No. is added means the same compound, and the content of compounds is shown in % by weight unless otherwise specified.

Characteristic data in Composition Examples are shown by TNI (nematic-isotropic liquid phase transition temperature or clearing point), η (viscosity: determined at 20.0° C.), Δn (optical anisotropy value: determined at 25.0° C.), Δε (dielectric anisotropy value: determined at 25.0° C.), and Vth (threshold voltage: determined at 25.0° C.).

TABLE 1

| Method for designating compounds by using symbols $R-(A_1)-Z_1-\cdots-Z_n-(A_n)-X$ | |
|---|---|
| 1) Left side terminal group R— | Symbol |
| $C_nH_{2n+1}$— | n— |
| $C_nH_{2n+1}O$— | nO— |
| $C_nH_{2n+1}OC_mH_{2m}$— | nOm— |
| $CH_2$=CH— | v— |
| $CH_2$=CHC$_n$H$_{2n}$— | Vn— |
| $C_nH_{2n+1}CH$=CHC$_m$H$_{2m}$— | nVm— |
| $CF_2$=CH$_2$— | VFF— |
| 2) Ring structure —(A$_1$)—, —(A$_n$)— | Symbol |
| 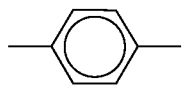 | B |
| 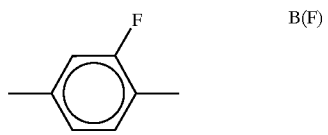 | B(F) |
| 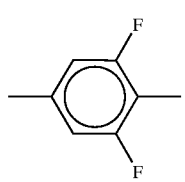 | B(F,F) |
|  | H |

TABLE 1-continued

Method for designating compounds by using symbols
R—(A₁)—Z₁—······—Zₙ—(Aₙ)—X

| Structure | Symbol |
|---|---|
| pyrimidine ring | Py |
| dioxane ring | G |
| cyclohexene (1,4) | Ch |
| 2-F cyclohexene | Ch(2F) |
| cyclohexene (other) | (Ch) |

3) Bonding group
—Z₁—, —Zₙ—  Symbol

| | |
|---|---|
| —C₂H₄— | 2 |
| —C₄H₈— | 4 |
| —COO— | E |
| —C≡C— | T |
| —CH=CH— | V |
| —CF₂O— | CF2O |
| —OCF₂— | OCF2 |

4) Right side terminal group —X  Symbol

| | |
|---|---|
| —F | —F |
| —Cl | —CL |
| —CN | —C |
| —CF₃ | —CF3 |
| —CF₂CF₃ | —CF2CF3 |
| —OCF₃ | —OCF3 |
| —OCF₂H | —OCF2H |
| —CₙH₂ₙ₊₁ | —n |
| —OCₙH₂ₙ₊₁ | —On |
| —COOCH₃ | —EMe |
| —CₙH₂ₙCH=CH₂ | —nV |
| —CₘH₂ₘCH=CHCₙH₂ₙ₊₁ | —mVn |
| —CₘH₂ₘCH=CHCₙH₂ₙF | —mVnF |
| —CH=CF₂ | —VFF |
| —CₙH₂ₙCH=CF₂ | —nVFF |
| —OCOCF₃ | —(E)CF3 |
| —CₙH₂ₙOCOCF₃ | —n(E)CF3 |

5) Examples of designation

Example 1    3-H2B(F,F)B(F)—F

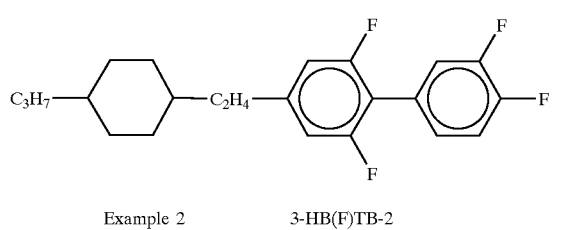

Example 2    3-HB(F)TB-2

TABLE 1-continued

Method for designating compounds by using symbols
R—(A₁)—Z₁—······—Zₙ—(Aₙ)—X

Example 3    1V2-BEB(F,F)—C

Example 4    3HH(E)CF3

TABLE 2

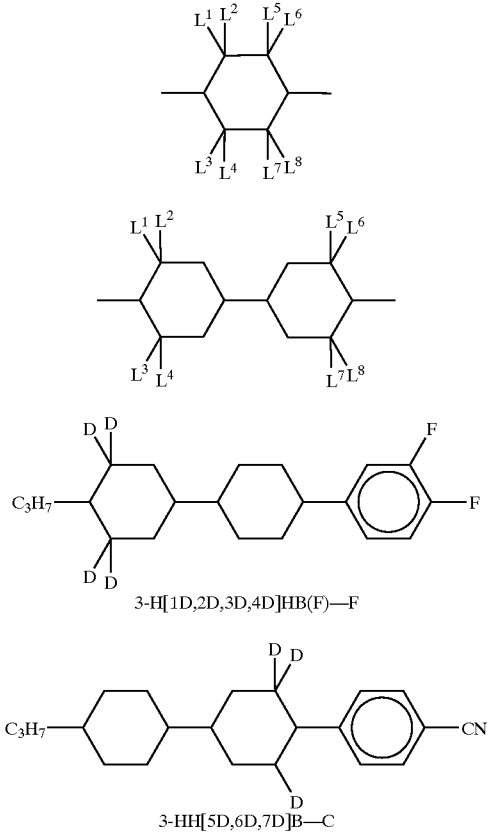

3-H[1D,2D,3D,4D]HB(F)—F

3-HH[5D,6D,7D]B—C

Composition Example 1

| | | |
|---|---|---|
| 3-HH—(E)CF3 | (No. 3) | 20.0% |
| 2-HH—(E)CF3 | (No. 2) | 14.0% |
| 3-BHH—(E)CF3 | (No. 251) | 10.0% |
| 5-HHB(F)—F | | 16.0% |
| 2-H2HB(F)—F | | 10.0% |
| 3-H2HB(F)—F | | 5.0% |
| 2-HBB(F)—F | | 6.0% |
| 3-HBB(F)—F | | 6.0% |
| 5-HBB(F)—F | | 13.0% |

Characteristic values of this composition were as follows:
TNI=70.4 (° C.)
$\eta$=20.8 (mPa·s)
$\Delta$n=0.079
$\Delta\epsilon$=5.0
Vth=2.31 (V)

Composition Example 2

| | | |
|---|---|---|
| 3-HH—(E)CF3 | (No. 3) | 10.0% |
| 3-HH-1(E)CF3 | (No. 31) | 10.0% |
| 7-HB(F,F)—F | | 3.0% |
| 3-HB—O2 | | 7.0% |
| 3-HHB(F)—F | | 10.0% |
| 2-HBB(F)—F | | 9.0% |
| 3-HBB(F)—F | | 9.0% |
| 5-HBB(F)—F | | 16.0% |
| 2-HBB—F | | 4.0% |
| 3-HBB—F | | 4.0% |
| 5-HBB—F | | 3.0% |
| 3-HBB(F,F)—F | | 5.0% |
| 5-HBB(F,F)—F | | 10.0% |

Characteristic values of this composition were as follows:
TNI=67.1 (° C.)
$\eta$=22.5 (mPa·s)
$\Delta$n=0.104
$\Delta\epsilon$=5.1
Vth=2.16 (V)

Composition Example 3

| | | |
|---|---|---|
| 3-HH—(E)CF3 | (No.3) | 8.0% |
| 3-BHH—(E)CF3 | (No. 251) | 8.0% |
| 3-HB—CL | | 10.0% |
| 5-HB—CL | | 4.0% |
| 7-HB—CL | | 4.0% |
| 1O1-HH-5 | | 3.0% |
| 2-HBB(F)—F | | 8.0% |
| 3-HBB(F)—F | | 8.0% |
| 4-HHB—CL | | 8.0% |
| 5-HHB—CL | | 8.0% |
| 3-H2HB(F)—CL | | 4.0% |
| 3-HBB(F,F)—F | | 10.0% |
| 5-H2BB(F,F)—F | | 9.0% |
| 3-HB(F)VB—2 | | 4.0% |
| 3-HB(F)VB—3 | | 4.0% |

Characteristic values of this composition were as follows:
TNI=77.3 (° C.)
$\eta$=18.5 (mPa·s)
$\Delta$n=0.110
$\Delta\epsilon$=4.8
Vth=2.39 (V)

Composition Example 4

| | | |
|---|---|---|
| 3-HH—(E)CF3 | (No. 3) | 5.0% |
| 2-HHB(F)—F | | 17.0% |
| 3-HHB(F)—F | | 17.0% |
| 5-HHB(F)—F | | 16.0% |
| 2-H2HB(F)—F | | 10.0% |
| 5-H2HB(F)—F | | 10.0% |
| 2-HBB(F)—F | | 6.0% |
| 3-HBB(F)—F | | 6.0% |
| 5-HBB(F)—F | | 13.0% |

Characteristic values of this composition were as follows:
TNI=96.5 (° C.)
$\eta$=14.2 (mPa·s)
$\Delta$n=0.094
$\Delta\epsilon$=5.1
Vth=2.18 (V)
Pitch of the liquid crystal composition prepared by adding 0.3 part by weight of the optically active compound expressed by the formula (Op-8) described above to 100 parts by weight of the composition 4 described above was 76.8 $\mu$m.

Composition Example 5

| | | |
|---|---|---|
| 3-HH—(E)CF3 | (No. 3) | 5.0% |
| 1V2-BEB(F,F)—C | | 5.0% |
| 3-HB—C | | 25.0% |
| 1-BTB-3 | | 5.0% |
| 2-BTB-1 | | 10.0% |
| 3-HH-4 | | 6.0% |
| 3-HHB-1 | | 11.0% |
| 3-HHB-3 | | 9.0% |
| 3-H2BTB-2 | | 4.0% |
| 3-H2BTB-3 | | 4.0% |
| 3-H2BTB-4 | | 4.0% |
| 3-HB(F)TB-2 | | 6.0% |
| 3-HB(F)TB-3 | | 6.0% |

Characteristic values of this composition were as follows:
TNI=88.8 (° C.)
$\eta$=15.3 (mPa·s)
$\Delta$n=0.163
$\Delta\epsilon$=7.5
Vth=1.99 (V)
Pitch of the liquid crystal composition prepared by adding 0.8 part by weight of the optically active compound expressed by the formula (Op-4) described above to 100 parts by weight of the composition 5 described above was 11.7 $\mu$m.

Composition Example 6

| | | |
|---|---|---|
| 3-HH—(E)CF3 | (No. 3) | 8.0% |
| 3-HHB(F,F)—F | | 9.0% |
| 3-H2HB(F,F)—F | | 8.0% |
| 4-H2HB(F,F)—F | | 8.0% |
| 3-HBB(F,F)—F | | 21.0% |

-continued

| | | |
|---|---|---|
| 5-HBB(F,F)—F | | 20.0% |
| 3-H2BB(F,F)—F | | 10.0% |
| 5-HHBB(F,F)—F | | 3.0% |
| 5-HHEBB—F | | 2.0% |
| 3-HH2BB(F,F)—F | | 3.0% |
| 1O1-HBBH-4 | | 4.0% |
| 1O1-HBBH-5 | | 4.0% |

Characteristic values of this composition were as follows:

TNI=93.4 (° C.)

η=32.9 (mPa·s)

Δn=0.114

Δε=8.9

Vth=1.81 (V)

Pitch of the liquid crystal composition prepared by adding 0.25 part by weight of the optically active compound expressed by the formula (Op-5) described above to 100 parts by weight of the composition 6 described above was 61.1 μm.

Composition Example 7

| | | |
|---|---|---|
| 3-HH—(E)CF3 | (No. 3) | 5.0% |
| 2-HH—(E)CF3 | (No. 2) | 4.0% |
| 5-HB—F | | 12.0% |
| 7-HB—F | | 7.0% |
| 2-HHB—OCF3 | | 7.0% |
| 3-HHB—OCF3 | | 7.0% |
| 4-HHB—OCF3 | | 7.0% |
| 5-HHB—OCF3 | | 5.0% |
| 3-HH2B—OCF3 | | 4.0% |
| 5-HH2B—OCF3 | | 4.0% |
| 3-HHB(F,F)—OCF3 | | 5.0% |
| 3-HBB(F)—F | | 10.0% |
| 5-HBB(F)—F | | 10.0% |
| 3-HH2B(F)—F | | 3.0% |
| 3-HB(F)BH-3 | | 3.0% |
| 5-HBBH-3 | | 3.0% |
| 3-HHB(F,F)—OCF2H | | 4.0% |

Characteristic values of this composition were as follows:

TNI=88.0 (° C.)

η=17.2 (mPa·s)

Δn=0.094

Δε=5.1

Vth=2.11 (V)

Composition Example 8

| | | |
|---|---|---|
| 3-HH—(E)CF3 | (No. 3) | 5.0% |
| 2-HH—(E)CF3 | (No. 2) | 5.0% |
| 3-HH-1(E)CF3 | (No. 31) | 5.0% |
| 3-BHH—(E)CF3 | (No. 251) | 5.0% |
| 2-HHB(F)—F | | 2.0% |
| 3-HHB(F)—F | | 2.0% |
| 5-HHB(F)—F | | 2.0% |
| 2-HBB(F)—F | | 6.0% |
| 3-HBB(F)—F | | 6.0% |
| 5-HBB(F)—F | | 10.0% |
| 2-H2BB(F)—F | | 9.0% |
| 3-H2BB(F)—F | | 9.0% |
| 3-HBB(F,F)—F | | 5.0% |
| 5-HBB(F,F)—F | | 19.0% |

-continued

| | |
|---|---|
| 1O1-HBBH-4 | 5.0% |
| 1O1-HBBH-5 | 5.0% |

Characteristic values of this composition were as follows:

TNI=90.5 (° C.)

η=32.1 (mPa·s)

Δn=0.120

Δε=6.2

Vth=2.03 (V)

Composition Example 9

| | | |
|---|---|---|
| 3-HH—(E)CF3 | (No. 3) | 10.0% |
| 2-HH—(E)CF3 | (No. 2) | 10.0% |
| 1V2-BEB(F,F)—C | | 5.0% |
| 3-HB—C | | 25.0% |
| 1-BTB-3 | | 5.0% |
| 3-HH-4 | | 6.0% |
| 3-HHB-1 | | 11.0% |
| 3-HHB-3 | | 4.0% |
| 3-H2BTB-2 | | 4.0% |
| 3-H2BTB-3 | | 4.0% |
| 3-H2BTB-4 | | 4.0% |
| 3-HB(F)TB-2 | | 6.0% |
| 3-HB(F)TB-3 | | 6.0% |

Characteristic values of this composition were as follows:

TNI=79.2 (° C.)

η=18.2 (mPa·s)

Δn=0.139

Δε=8.0

Vth=1.96 (V)

Composition Example 10

| | | |
|---|---|---|
| 3-HH—(E)CF3 | (No. 3) | 8.0% |
| 2-HH—(E)CF3 | (No. 2) | 12.0% |
| 3-HH-1(E)CF3 | (No. 31) | 5.0% |
| 3-BHH—(E)CF3 | (No. 251) | 8.0% |
| 3O1-BEB(F)—C | | 15.0% |
| 4O1-BEB(F)—C | | 13.0% |
| 2-HHB(F)—C | | 15.0% |
| 3-HB(F)TB-2 | | 4.0% |
| 3-HB(F)TB-3 | | 4.0% |
| 3-HB(F)TB-4 | | 4.0% |
| 3-HHB-1 | | 8.0% |
| 3-HHB—O1 | | 4.0% |

Characteristic values of this composition were as follows:

TNI=74.4 (° C.)

η=68.8 (mPa·s)

Δn=0.121

Δε=24.8

Vth=1.20 (V)

Composition Example 11

| | | |
|---|---|---|
| 3-HH—(E)CF3 | (No. 3) | 15.0% |
| 1V2-BEB(F,F)—C | | 6.0% |
| 3-HB—C | | 18.0% |
| 2-BTB-1 | | 10.0% |
| 5-HH—VFF | | 15.0% |
| 1-BHH—VFF | | 8.0% |
| 1-BHH-2VFF | | 11.0% |
| 3-H2BTB-2 | | 5.0% |
| 3-H2BTB-3 | | 4.0% |
| 3-H2BTB-4 | | 4.0% |
| 3-HHB-1 | | 4.0% |

Characteristic values of this composition were as follows:

TNI=76.7 (° C.)

$\eta$=15.1 (mPa·s)

$\Delta n$=0.130

$\Delta \epsilon$=7.4

Vth=1.88 (V)

Composition Example 12

| | | |
|---|---|---|
| 3-HH—(E)CF3 | (No. 3) | 10.0% |
| 7-HB(F,F)—F | | 5.0% |
| 3-H2HB(F,F)—F | | 12.0% |
| 3-HHB(F,F)—F | | 10.0% |
| 4-HHB(F,F)—F | | 5.0% |
| 3-HBB(F,F)—F | | 10.0% |
| 3-HHEB(F,F)—F | | 10.0% |
| 4-HHEB(F,F)—F | | 3.0% |
| 5-HHEB(F,F)—F | | 3.0% |
| 2-HBEB(F,F)—F | | 3.0% |
| 3-HBEB(F,F)—F | | 5.0% |
| 5-HBEB(F,F)—F | | 3.0% |
| 3-HGB(F,F)—F | | 15.0% |
| 3-HHBB(F,F)—F | | 6.0% |

Characteristic values of this composition were as follows:

TNI=71.1 (° C.)

$\eta$=31.8 (mPa·s)

$\Delta n$=0.083

$\Delta \epsilon$=13.0

Vth=1.39 (V)

Composition Example 13

| | | |
|---|---|---|
| 3-BHH—(E)CF3 | (No. 251) | 4.0% |
| 2-BCF2OBH—(E)CF3 | (No. 275) | 3.0% |
| 3-BHHH—(E)CF3 | (No. 301) | 3.0% |
| 5-H4HB(F,F)—F | | 7.0% |
| 5-H4HB—OCF3 | | 15.0% |
| 3-H4HB(F,F)—CF3 | | 8.0% |
| 3-HB—CL | | 6.0% |
| 5-HB—CL | | 4.0% |
| 2-H2BB(F)—F | | 5.0% |
| 3-H2BB(F)—F | | 10.0% |
| 5-HVHB(F,F)—F | | 5.0% |
| 3-HHB—OCF3 | | 5.0% |
| 3-H2HB—OCF3 | | 5.0% |
| V-HHB(F)—F | | 5.0% |
| 3-HHB(F)—F | | 5.0% |
| 5-HHEB—OCF3 | | 2.0% |
| 3-HBEB(F,F)—F | | 5.0% |
| 5-HH—V2F | | 3.0% |

Composition Example 14

| | | |
|---|---|---|
| 3-HH-1(E)CF3 | (No. 31) | 4.0% |
| 3-HH-2(E)CF3 | (No. 34) | 4.0% |
| VFF—HH—(E)CF3 | (No. 16) | 4.0% |
| 5-HB—CL | | 12.0% |
| 3-HH-4 | | 2.0% |
| 3-HB—O2 | | 20.0% |
| 3-H2HB(F,F)—F | | 3.0% |
| 3-HHB(F,F)—F | | 8.0% |
| 3-HBB(F,F)—F | | 6.0% |
| 2-HHB(F)—F | | 5.0% |
| 3-HHB(F)—F | | 5.0% |
| 5-HHB(F)—F | | 5.0% |
| 2-H2HB(F)—F | | 2.0% |
| 3-H2HB(F)—F | | 1.0% |
| 5-H2HB(F)—F | | 2.0% |
| 3-HHBB(F,F)—F | | 4.0% |
| 3-HBCF2OB—OCF3 | | 4.0% |
| 5-HBCF2OB(F,F)—CF3 | | 4.0% |
| 3-HHB-1 | | 3.0% |
| 3-HHB—O1 | | 2.0% |

Composition Example 15

| | | |
|---|---|---|
| 3-HH—(E)CF3 | (No. 3) | 5.0% |
| 3-B(F,F)2HH—(E)CF3 | (No. 255) | 2.0% |
| 3-GH—(E)CF3 | (No. 43) | 2.0% |
| 3-GB(F,F)EH—(E)CF3 | (No. 259) | 2.0% |
| 3-HH-2(E)CF3 | (No. 34) | 2.0% |
| 1-BCh(2F)H—(E)CF3 | (No. 262) | 2.0% |
| 3-H2HB(F,F)—F | | 7.0% |
| 5-H2HB(F,F)—F | | 8.0% |
| 3-HHB(F,F)—F | | 10.0% |
| 4-HHB(F,F)—F | | 5.0% |
| 3-HH2B(F,F)—F | | 9.0% |
| 5-HH2B(F,F)—F | | 9.0% |
| 3-HBB(F,F)—F | | 15.0% |
| 3-HBEB(F,F)—F | | 2.0% |
| 4-HBEB(F,F)—F | | 2.0% |
| 5-HBEB(F,F)—F | | 2.0% |
| 3-HHEB(F,F)—F | | 10.0% |
| 4-HHEB(F,F)—F | | 3.0% |
| 5-HHEB(F,F)—F | | 3.0% |

Composition Example 16

| | | |
|---|---|---|
| 3-HB—(E)CF3 | (No. 191) | 2.0% |
| 3-B(F,F)H—(E)CF3 | (No. 142) | 2.0% |
| VFF—HH—(E)CF3 | (No. 16) | 2.0% |
| 2-BCF2OBH—(E)CF3 | (No. 275) | 2.0% |
| 5-ChH—(E)CF3 | (No. 122) | 2.0% |
| 7-HB(F)—F | | 5.0% |
| 5-H2B(F)—F | | 5.0% |
| 3-HB—O2 | | 10.0% |
| 3-HH-4 | | 2.0% |
| 3-HH(5D,6D,7D)-4 | | 3.0% |
| 2-HHB(F)—F | | 10.0% |
| 3-HHB(F)—F | | 10.0% |
| 5-HH(5D,6D,7D)B(F)—F | | 10.0% |
| 3-H2HB(F)—F | | 5.0% |

-continued

| | | |
|---|---|---|
| 2-HBB(F)—F | | 3.0% |
| 3-HBB(F)—F | | 3.0% |
| 5-HBB(F)—F | | 6.0% |
| 2-H2BB(F)—F | | 5.0% |
| 3-H2BB(F)—F | | 6.0% |
| 3-HHB-1 | | 2.0% |
| 3-HHB—O1 | | 3.0% |
| 3-HHB-3 | | 2.0% |

Composition Example 17

| | | |
|---|---|---|
| 3-GB—(E)CF3 | (No. 201) | 2.0% |
| 3-HH—(E)CF2H | (No. 4) | 2.0% |
| V2-BH2H—(E)CF3 | (No. 258) | 2.0% |
| 3-GB(F,F)—(E)CF3 | (No. 202) | 2.0% |
| 3-BHHH—(E)CF3 | (No. 301) | 2.0% |
| 3-HH—(E)CF2CF3 | (No. 6) | 2.0% |
| 7-HB(F,F)—F | | 3.0% |
| 3-H2HB(F,F)—F | | 12.0% |
| 4-H2HB(F,F)—F | | 10.0% |
| 5-H2HB(F,F)—F | | 10.0% |
| 3-HHB(F,F)—F | | 5.0% |
| 4-HHB(F,F)—F | | 5.0% |
| 3-HH2B(F,F)—F | | 15.0% |
| 5-HH2B(F,F)—F | | 10.0% |
| 5-HBB(F,F)—F | | 12.0% |
| 3-HBCF2OB(F,F)—F | | 6.0% |

Composition Example 18

| | | |
|---|---|---|
| 3-B(F,F)2HH—(E)CF3 | (No. 255) | 3.0% |
| 3-HB—(E)CF3 | (No. 191) | 3.0% |
| 3-HH—2(E)CF3 | (No. 34) | 4.0% |
| 5-ChH—(E)CF3 | (No. 122) | 2.0% |
| V2—BH2H—(E)CF3 | (No. 258) | 2.0% |
| 2O1—BEB(F)—C | | 5.0% |
| 3O1—BEB(F)—C | | 12.0% |
| 5O1—BEB(F)—C | | 4.0% |
| 1V2—BEB(F,F)—C | | 10.0% |
| 3-HH—EMe | | 6.0% |
| 3-HB—O2 | | 18.0% |
| 7-HEB—F | | 2.0% |
| 3-HHEB—F | | 2.0% |
| 5-HHEB—F | | 2.0% |
| 3-HBEB—F | | 4.0% |
| 2O1-HBEB(F)—C | | 2.0% |
| 3-HB(F)EB(F)—C | | 2.0% |
| 3-HBEB(F,F)—C | | 2.0% |
| 3-HHB—F | | 4.0% |
| 3-HHB—O1 | | 4.0% |
| 3-HHB-3 | | 3.0% |
| 3-HEBEB—F | | 2.0% |
| 3-HEBEB-1 | | 2.0% |

Composition Example 19

| | | |
|---|---|---|
| 3-GH—(E)CF3 | (No. 43) | 2.0% |
| 3-GB(F,F)EH—(E)CF3 | (No. 259) | 2.0% |
| 1-BCh(2F)H—(E)CF3 | (No. 262) | 2.0% |
| VFF—HH—(E)CF3 | (No. 16) | 2.0% |
| 2-BCF2OBH—(E)CF3 | (No. 275) | 2.0% |
| 3-HH—(E)CF2CF3 | (No. 6) | 2.0% |
| 2-HB—C | | 5.0% |
| 3-HB—C | | 12.0% |
| 3-HB—O2 | | 3.0% |

-continued

| | | |
|---|---|---|
| 2-BTB-1 | | 3.0% |
| 3-HHB-1 | | 8.0% |
| 3-HHB—F | | 4.0% |
| 3-HHB—O1 | | 5.0% |
| 3-HHB-3 | | 14.0% |
| 3-HHEB—F | | 4.0% |
| 5-HHEB—F | | 4.0% |
| 2-HHB(F)—F | | 7.0% |
| 3-HHB(F)—F | | 7.0% |
| 5-HHB(F)—F | | 7.0% |
| 3-HHB(F,F)—F | | 5.0% |

Composition Example 20

| | | |
|---|---|---|
| 3-B(F,F)H—(E)CF3 | (No. 142) | 4.0% |
| 3-GB—(E)CF3 | (No. 201) | 4.0% |
| 3-HH—(E)CF2H | (No. 4) | 3.0% |
| 3-GB(F,F)—(E)CF3 | (No. 202) | 2.0% |
| 3-BHHH—(E)CF3 | (No. 301) | 4.0% |
| V2—HB—C | | 12.0% |
| 1V2—HB—C | | 12.0% |
| 3-HB—C | | 15.0% |
| 3-H(1D,2D,3D)B—C | | 9.0% |
| 3-HB(F)—C | | 5.0% |
| 2-BTB-1 | | 2.0% |
| 3-HH-4 | | 8.0% |
| 3-HH—VFF | | 2.0% |
| 2-H(1D,2D,3D)HB—C | | 3.0% |
| 3-HHB—C | | 6.0% |
| 3-HB(F)TB-2 | | 4.0% |
| 3-H2BTB-2 | | 5.0% |

Composition Example 21

| | | |
|---|---|---|
| 4-HH—(E)CF3 | (No. 1) | 5.0% |
| 1V2—BEB(F,F)—C | | 5.0% |
| 3-HB—C | | 25.0% |
| 1-BTB-3 | | 5.0% |
| 2-BTB-1 | | 5.0% |
| 3-HH-4 | | 11.0% |
| 3-HHB-1 | | 11.0% |
| 3-HHB-3 | | 9.0% |
| 3-H2BTB-2 | | 4.0% |
| 3-H2BTB-3 | | 4.0% |
| 3-H2BTB-4 | | 4.0% |
| 3-HB(F)TB-2 | | 6.0% |
| 3-HB(F)TB-3 | | 6.0% |

Characteristic values of this composition were as follows:

TNI=91.9 (° C.)

$\eta$=15.2 (mPa·s)

$\Delta n$=0.152

$\Delta \epsilon$=7.8

Vth=2.02 (V)

Pitch of the liquid crystal composition prepared by adding 0.8 part by weight of the optically active compound expressed by the formula (Op-4) described above to 100 parts by weight of the composition 21 described above was 11.3 µm.

Composition Example 22

| | | |
|---|---|---|
| 4H(Ch)H—(E)CF3 | (No. 343) | 5.0% |
| 2O1—BEB(F)—C | | 5.0% |
| 3O1—BEB(F)—C | | 15.0% |
| 4O1—BEB(F)—C | | 13.0% |
| 5O1—BEB(F)—C | | 13.0% |
| 2-HHB(F)—C | | 15.0% |
| 3-HHB(F)—C | | 15.0% |
| 3-HB(F)TB-2 | | 4.0% |
| 3-HB(F)TB-3 | | 4.0% |
| 3-HB(F)TB-4 | | 4.0% |
| 3-HHB-1 | | 3.0% |
| 3-HHB—O1 | | 4.0% |

Characteristic values of this composition were as follows:

TNI=90.6 (° C.)

η=88.3 (mPa·s)

Δn=0.147

Δε=31.7

Vth=0.83 (V)

Composition Example 23

| | | |
|---|---|---|
| 3-HH—(E)CF2CF3 | (No. 6) | 6.0% |
| 4-HHH—(E)CF3 | (No. 232) | 2.0% |
| 5-H2ChH—(E)CF3 | (No. 245) | 2.0% |
| 3-DB—C | | 10.0% |
| 4-DB—C | | 10.0% |
| 2-BEB—C | | 12.0% |
| 3-BEB—C | | 4.0% |
| 3-PyB(F)—F | | 6.0% |
| 3-HEB—O4 | | 2.0% |
| 4-HEB—O2 | | 2.0% |
| 5-HEB—O1 | | 6.0% |
| 3-HEB—O2 | | 5.0% |
| 5-HEB—O2 | | 4.0% |
| 5-HEB-5 | | 5.0% |
| 4-HEB-5 | | 5.0% |
| 1O—BEB-2 | | 4.0% |
| 3-HHB-1 | | 6.0% |
| 3-HHEBB—C | | 3.0% |
| 3-HBEBB—C | | 3.0% |
| 5-HBEBB—C | | 3.0% |

Characteristic values of this composition were as follows:

TNI=68.6 (° C.)

η=40.3 (mPa·s)

Δn=0.119

Δε=12.3

Vth=1.26 (V)

Composition Example 24

| | | |
|---|---|---|
| 4-H(Ch)H—(E)CF3 | (No. 343) | 4.0% |
| 5-H2ChH—(E)CF3 | (No. 245) | 4.0% |
| 3-HB—C | | 18.0% |
| 7-HB—C | | 3.0% |
| 1O1—HB—C | | 10.0% |
| 3-HB(F)—C | | 10.0% |
| 2-PyB-2 | | 2.0% |
| 3-PyB-2 | | 2.0% |
| 4-PyB-2 | | 2.0% |
| 1O1—HH-3 | | 7.0% |
| 2-BTB—O1 | | 7.0% |
| 3-HHB-1 | | 7.0% |
| 3-HHB—F | | 4.0% |
| 3-HHB—O1 | | 4.0% |
| 3-H2BTB-2 | | 3.0% |
| 3-H2BTB-3 | | 3.0% |
| 2-PyBH-3 | | 4.0% |
| 3-PyBH-3 | | 3.0% |
| 3-PyBB-2 | | 3.0% |

Characteristic values of this composition were as follows:

TNI=75.1 (° C.)

η=19.3 (mPa·s)

Δn=0.135

Δε=8.8

Vth=1.66 (V)

Composition Example 25

| | | |
|---|---|---|
| 4-HHH—(E)CF3 | (No. 232) | 2.0% |
| 4-H(Ch)H—(E)CF3 | (No. 343) | 6.0% |
| 2O1—BEB(F)—C | | 5.0% |
| 3O1—BEB(F)—C | | 12.0% |
| 5O1—BEB(F)—C | | 4.0% |
| 1V2—BEB(F,F)—C | | 10.0% |
| 3-HH—EMe | | 10.0% |
| 3-HB—O2 | | 18.0% |
| 7-HEB—F | | 2.0% |
| 3-HHEB—F | | 2.0% |
| 5-HHEB—F | | 2.0% |
| 3-HBEB—F | | 4.0% |
| 2O1—HBEB(F)—C | | 2.0% |
| 3-HB(F)EB(F)—C | | 2.0% |
| 3-HBEB(F,F)—C | | 2.0% |
| 3-HHB—F | | 4.0% |
| 3-HHB—O1 | | 4.0% |
| 3-HHB-3 | | 5.0% |
| 3-HEBEB—F | | 2.0% |
| 3-HEBEB-1 | | 2.0% |

Characteristic values of this composition were as follows:

TNI=72.6 (° C.)

η=36.8 (mPa·s)

Δn=0.110

Δε=24.4

Vth=0.96 (V)

Composition Example 26

| | | |
|---|---|---|
| 4-GHH—(E)CF3 | (No. 241) | 4.0% |
| 4-H(Ch)H—(E)CF3 | (No. 343) | 4.0% |
| 2-HB—C | | 5.0% |
| 3-HB—C | | 12.0% |
| 3-HB—O2 | | 15.0% |
| 2-BTB-1 | | 3.0% |
| 3-HHB-1 | | 8.0% |
| 3-HHB—F | | 4.0% |
| 3-HHB—O1 | | 5.0% |
| 3-HHB-3 | | 6.0% |
| 3-HHEB—F | | 4.0% |
| 5-HHEB—F | | 4.0% |
| 2-HHB(F)—F | | 7.0% |
| 3-HHB(F)—F | | 7.0% |
| 5-HHB(F)—F | | 7.0% |

-continued

| 3-HHB(F,F)—F | 5.0% |
|---|---|

Characteristic values of this composition were as follows:

TNI=96.7 (° C.)

η=19.3 (mPa·s)

Δn=0.096

Δε=5.2

Vth=2.47 (V)

Composition Example 27

| 4-H(Ch)H—(E)CF3 | (No. 343) | 5.0% |
|---|---|---|
| 5-H2ChH—(E)CF3 | (No. 245) | 5.0% |
| 1V2—BEB(F,F)—C | | 6.0% |
| 3-HB—C | | 18.0% |
| 2-BTB-1 | | 10.0% |
| 5-HH—VFF | | 30.0% |
| 1-BHH—VFF | | 6.0% |
| 1-BHH—2VFF | | 3.0% |
| 3-H2BTB-2 | | 5.0% |
| 3-H2BTB-3 | | 4.0% |
| 3-H2BTB-4 | | 4.0% |
| 3-HHB-1 | | 4.0% |

Characteristic values of this composition were as follows:

TNI=77.4 (° C.)

η=13.5 (mPa·s)

Δn=0.124

Vth =1.96 (V)

Composition Example 28

| 2-HH—(E)CF3 | (No. 2) | 14.0% |
|---|---|---|
| 4-HH—(E)CF3 | (No. 1) | 19.0% |
| 4-HH(Ch)—(E)CF3 | (No. 341) | 5.0% |
| 5-H2ChH—(E)CF3 | (No. 245) | 5.0% |
| 2-HHB(F)—F | | 17.0% |
| 2-H2HB(F)—F | | 10.0% |
| 3-H2HB(F)—F | | 5.0% |
| 2-HBB(F)—F | | 6.0% |
| 3-HBB(F)—F | | 6.0% |
| 5-HBB(F)—F | | 13.0% |

Characteristic values of this composition were as follows:

TNI=71.7 (° C.)

η=23.6 (mPa·s)

Δn=0.075

Δε=5.9

Vth=2.08 (V)

Pitch of the liquid crystal composition prepared by adding 0.3 part by weight of the optically active compound expressed by the formula (Op-8) described above to 100 parts by weight of the composition 28 described above was 72.8 μm.

Composition Example 29

| 2-HH—(E)CF2H | (No. 5) | 7.0% |
|---|---|---|
| 3-H(Ch)—(E)CF3 | (No. 121) | 5.0% |
| 4-GHH—(E)CF3 | (No. 241) | 3.0% |
| 4-H(Ch)H—(E)CF3 | (No. 343) | 5.0% |
| 7-HB(F,F)—F | | 3.0% |
| 3-HB—O2 | | 7.0% |
| 3-HHB(F)—F | | 5.0% |
| 5-HHB(F)—F | | 5.0% |
| 2-HBB(F)—F | | 9.0% |
| 3-HBB(F)—F | | 9.0% |
| 5-HBB(F)—F | | 16.0% |
| 2-HBB—F | | 4.0% |
| 3-HBB—F | | 4.0% |
| 5-HBB—F | | 3.0% |
| 3-HBB(F,F)—F | | 5.0% |
| 5-HBB(F,F)—F | | 10.0% |

Characteristic values of this composition were as follows:

TNI=70.6 (° C.)

η=24.2 (mPa·s)

Δn=0.099

Δε=6.4

Vth=1.91 (V)

Composition Example 30

| 3-HH—(E)CF3 | (No. 3) | 4.0% |
|---|---|---|
| 3-HH—(E)CF2CF3 | (No. 6) | 10.0% |
| 3-HB—CL | | 10.0% |
| 5-HB—CL | | 4.0% |
| 7-HB—CL | | 4.0% |
| 1O1—HH-5 | | 5.0% |
| 2-HBB(F)—F | | 8.0% |
| 3-HBB(F)—F | | 8.0% |
| 4-HHB—CL | | 8.0% |
| 5-HHB—CL | | 8.0% |
| 3-H2HB(F)—CL | | 4.0% |
| 3-HBB(F,F)—F | | 10.0% |
| 5-H2BB(F,F)—F | | 9.0% |
| 3-HB(F)VB-2 | | 4.0% |
| 3-HB(F)VB-3 | | 4.0% |

Characteristic values of this composition were as follows:

TNI=77.8 (° C.)

η=19.8 (mPa·s)

Δn=0.114

Δε=5.3

Vth=2.21 (V)

Composition Example 31

| 4-HH—(E)CF3 | (No. 1) | 4.0% |
|---|---|---|
| 2-HH—(E)CF2H | (No. 5) | 4.0% |
| 4-HH(Ch)—(E)CF3 | (No. 341) | 4.0% |
| 3-HHB(F,F)—F | | 9.0% |
| 3-H2HB(F,F)—F | | 4.0% |
| 4-H2HB(F,F)—F | | 4.0% |
| 5-H2HB(F,F)—F | | 4.0% |
| 3-HBB(F,F)—F | | 21.0% |
| 5-HBB(F,F)—F | | 20.0% |
| 3-H2BB(F,F)—F | | 10.0% |
| 5-HHBB(F,F)—F | | 3.0% |
| 5-HHEBB—F | | 2.0% |

-continued

| | | |
|---|---|---|
| 3-HH2BB(F,F)—F | | 3.0% |
| 1O1—HBBH-4 | | 4.0% |
| 1O1—HBBH-5 | | 4.0% |

Characteristic values of this composition were as follows:
TNI=94.7 (° C.)
η=34.5 (mPa·s)
Δn=0.113
Δε=9.2
Vth=1.73 (V)

Pitch of the liquid crystal composition prepared by adding 0.25 part by weight of the optically active compound expressed by the formula (Op-5) described above to 100 parts by weight of the composition 31 described above was 62.3 μm.

Composition Example 32

| | | |
|---|---|---|
| 2-HH—(E)CF2H | (No. 5) | 3.0% |
| 4-H(Ch)H—(E)CF3 | (No. 343) | 6.0% |
| 5-HB—F | | 12.0% |
| 6-HB—F | | 9.0% |
| 7-HB—F | | 7.0% |
| 2-HHB—OCF3 | | 7.0% |
| 3-HHB—OCF3 | | 5.0% |
| 5-HHB—OCF3 | | 5.0% |
| 3-HH2B—OCF3 | | 4.0% |
| 5-HH2B—OCF3 | | 4.0% |
| 3-HHB(F,F)—OCF3 | | 5.0% |
| 3-HBB(F)—F | | 10.0% |
| 5-HBB(F)—F | | 10.0% |
| 3-HH2B(F)—F | | 3.0% |
| 3-HB(F)BH-3 | | 3.0% |
| 5-HBBH-3 | | 3.0% |
| 3-HHB(F,F)—OCF2H | | 4.0% |

Characteristic values of this composition were as follows:
TNI=78.7 (° C.)
η=15.3 (mPa·s)
Δn=0.088
Δε=5.0
Vth=2.31 (V)

Composition Example 33

| | | |
|---|---|---|
| 3-HH—(E)CF2CF3 | (No. 6) | 5.0% |
| 4-HHH—(E)CF3 | (No. 232) | 2.0% |
| 2-HHB(F)—F | | 2.0% |
| 3-HHB(F)—F | | 2.0% |
| 5-HHB(F)—F | | 2.0% |
| 2-HBB(F)—F | | 6.0% |
| 3-HBB(F)—F | | 6.0% |
| 5-HBB(F)—F | | 10.0% |
| 2-H2BB(F)—F | | 9.0% |
| 3-H2BB(F)—F | | 9.0% |
| 3-HBB(F,F)—F | | 25.0% |
| 5-HBB(F,F)—F | | 12.0% |
| 1O1—HBBH-4 | | 5.0% |
| 1O1—HBBH-5 | | 5.0% |

Characteristic values of this composition were as follows:
TNI=96.2 (° C.)
η=34.3 (mPa·s)
Δn=0.127
Δε=7.4
Vth=1.90 (V)

Composition Example 34

| | | |
|---|---|---|
| 4-H(Ch)H—(E)CF3 | (No. 343) | 8.0% |
| 4-GHH—(E)CF3 | (No. 241) | 2.0% |
| 7-HB(F)—F | | 5.0% |
| 5-H2B(F)—F | | 5.0% |
| 3-HB—O2 | | 10.0% |
| 3-HH-4 | | 5.0% |
| 2-HHB(F)—F | | 10.0% |
| 3-HHB(F)—F | | 10.0% |
| 5-HHB(F)—F | | 10.0% |
| 3-H2HB(F)—F | | 5.0% |
| 2-HBB(F)—F | | 3.0% |
| 3-HBB(F)—F | | 3.0% |
| 5-HBB(F)—F | | 6.0% |
| 2-H2BB(F)—F | | 5.0% |
| 3-H2BB(F)—F | | 6.0% |
| 3-HHB-1 | | 2.0% |
| 3-HHB—O1 | | 2.0% |
| 3-HHB-3 | | 3.0% |

Characteristic values of this composition were as follows:
TNI=82.9 (° C.)
η=19.3 (mPa·s)
Δn=0.088
Δε=3.9
Vth=2.41 (V)

Composition Example 35

| | | |
|---|---|---|
| 3-H(Ch)—(E)CF3 | (No. 121) | 5.0% |
| 7-HB(F,F)—F | | 3.0% |
| 3-H2HB(F,F)—F | | 12.0% |
| 4-H2HB(F,F)—F | | 10.0% |
| 5-H2HB(F,F)—F | | 10.0% |
| 3-HHB(F,F)—F | | 5.0% |
| 4-HHB(F,F)—F | | 5.0% |
| 3-HH2B(F,F)—F | | 15.0% |
| 5-HH2B(F,F)—F | | 10.0% |
| 3-HBB(F,F)—F | | 12.0% |
| 5-HBB(F,F)—F | | 7.0% |
| 3-HBCF2OB(F,F)—F | | 6.0% |

Characteristic values of this composition were as follows:
TNI=70.1 (° C.)
η=25.9 (mPa·s)
Δn=0.081
Δε=8.9
Vth=1.52 (V)

Composition Example 36

| | | |
|---|---|---|
| 2-HH—(E)CF2H | (No. 5) | 5.0% |
| 5-H4HB(F,F)—F | | 7.0% |
| 5-H4HB—OCF3 | | 15.0% |
| 3-H4HB(F,F)—CF3 | | 8.0% |
| 5-H4HB(F,F)—CF3 | | 10.0% |
| 3-HB—CL | | 3.0% |
| 5-HB—CL | | 2.0% |
| 2-H2BB(F)—F | | 5.0% |

-continued

| | |
|---|---|
| 3-H2BB(F)—F | 10.0% |
| 5-HVHB(F,F)—F | 5.0% |
| 3-HHB—OCF3 | 5.0% |
| 3-H2HB—OCF3 | 5.0% |
| V—HHB(F)—F | 5.0% |
| 3-HHB(F)—F | 5.0% |
| 5-HHEB—OCF3 | 2.0% |
| 3-HBEB(F,F)—F | 5.0% |
| 5-HH—V2F | 3.0% |

Characteristic values of this composition were as follows:
TNI=69.3 (° C.)
η=25.7 (mPa·s)
Δn=0.089
Δε=8.6
Vth=1.70 (V)

Composition Example 37

| | | |
|---|---|---|
| 4-HH—(E)CF3 | (No. 1) | 4.0% |
| 2-HH—(E)CF2H | (No. 5) | 4.0% |
| 5-HB—CL | | 7.0% |
| 3-HH-4 | | 4.0% |
| 3-HB—O2 | | 20.0% |
| 3-H2HB(F,F)—F | | 8.0% |
| 3-HHB(F,F)—F | | 8.0% |
| 3-HBB(F,F)—F | | 6.0% |
| 2-HHB(F)—F | | 5.0% |
| 3-HHB(F)—F | | 5.0% |
| 5-HHB(F)—F | | 5.0% |
| 2-H2HB(F)—F | | 2.0% |
| 3-H2HB(F)—F | | 1.0% |
| 5-H2HB(F)—F | | 2.0% |
| 3-HHBB(F,F)—F | | 4.0% |
| 3-HBCF2OB—OCF3 | | 4.0% |
| 5-HBCF2OB(F,F)—CF3 | | 4.0% |
| 3-HHB-1 | | 3.0% |
| 3-HHB—O1 | | 4.0% |

Characteristic values of this composition were as follows:
TNI=72.8 (° C.)
η=17.6 (mPa·s)
Δn=0.082
Δε=5.0
Vth=2.08 (V)

Composition Example 38

| | | |
|---|---|---|
| 4-HH—(E)CF3 | (No. 1) | 6.0% |
| 4-H(Ch)H—(E)CF3 | (No. 343) | 5.0% |
| 3-BEB(F)—C | | 8.0% |
| 3-HB—C | | 8.0% |
| V—HB—C | | 8.0% |
| 1V—HB—C | | 4.0% |
| 5-PyB—C | | 4.0% |
| 3-HB—O2 | | 3.0% |
| V2V—HH-3 | | 4.0% |
| 3-HH—2V | | 4.0% |
| 3-HH—2V1 | | 4.0% |
| 5-HH—VFF | | 3.0% |
| V2—HHB-1 | | 10.0% |
| 3-HHB-1 | | 5.0% |
| 3-HHEB—F | | 7.0% |
| 3-H2BTB-2 | | 6.0% |
| 3-H2BTB-3 | | 6.0% |
| 3-H2BTB-4 | | 5.0% |

Composition Example 39

| | | |
|---|---|---|
| 2-HH—(E)CF3 | (No. 2) | 6.0% |
| 4-H(Ch)H—(E)CF3 | (No. 343) | 5.0% |
| 5-BEB(F)—C | | 5.0% |
| V—HB—C | | 11.0% |
| 5-PyB—C | | 6.0% |
| 4-BB-3 | | 10.0% |
| 3-HH—2V | | 6.0% |
| V2V—HH-3 | | 4.0% |
| 5-HH—V | | 6.0% |
| V—HHB-1 | | 7.0% |
| V2—HHB-1 | | 10.0% |
| 3-HHB-1 | | 9.0% |
| 1V2—HBB-2 | | 10.0% |
| 3-HHEBH-3 | | 5.0% |

Composition Example 40

| | | |
|---|---|---|
| 2-HH—(E)CF2H | (No. 5) | 4.0% |
| 4-HHH—(E)CF3 | (No. 232) | 1.0% |
| 4-GHH—(E)CF3 | (No. 241) | 2.0% |
| 5-H2ChH—(E)CF3 | (No. 245) | 1.0% |
| V2—HB—TC | | 10.0% |
| 3-HB—TC | | 10.0% |
| 3-HB—C | | 10.0% |
| 5-HB—C | | 7.0% |
| 5-BB—C | | 3.0% |
| 2-BTB-1 | | 10.0% |
| 2-BTB—O1 | | 5.0% |
| 3-HH-4 | | 3.0% |
| 3-HHB-1 | | 10.0% |
| 3-HHB-3 | | 5.0% |
| 3-H2BTB-2 | | 3.0% |
| 3-H2BTB-3 | | 3.0% |
| 3-HB(F)TB-2 | | 3.0% |
| 5-BTB(F)TB-3 | | 10.0% |

Composition Example 41

| | | |
|---|---|---|
| 3-HH—(E)CF2CF3 | (No. 6) | 4.0% |
| 3-HGH—(E)CF3 | (No. 242) | 2.0% |
| 3-HHEH—(E)CF3 | (No. 238) | 2.0% |
| 3-HVHH—(E)CF3 | (No. 237) | 2.0% |
| 7-HB(F,F)—F | | 5.0% |
| 3-H2HB(F,F)—F | | 12.0% |
| 4-H2HB(F,F)—F | | 10.0% |
| 3-HHB(F,F)—F | | 5.0% |
| 4-HHB(F,F)—F | | 5.0% |
| 3-HBB(F,F)—F | | 10.0% |
| 3-HHEB(F,F)—F | | 5.0% |
| 4-HHEB(F,F)—F | | 3.0% |
| 5-HHEB(F,F)—F | | 3.0% |
| 2-HBEB(F,F)—F | | 3.0% |
| 3-HBEB(F,F)—F | | 5.0% |
| 5-HBEB(F,F)—F | | 3.0% |
| 3-HGB(F,F)—F | | 15.0% |
| 3-HHBB(F,F)—F | | 6.0% |

The compounds of the present invention expressed by the general formula (1) can readily be produced by the methods described in known literatures, for example, "Jikken Kagaku Kouza (Course of Chemical Experiment)" fourth edition (Maruzen) and *J. Org. Chem.*, 62, 726 (1997).

Among the compounds expressed by the general formula (1), compound (18) wherein both $Y_1$ and $Y_2$ are oxygen atoms can preferably be produced by reacting a compound having a hydroxyl group $R_1-(A_1-Za)_{n1}-(A_2-Zb)_{n2}-(A_3-Zc)_{n3}-A_4-Zd-A_5-Ze-OH$ (16) with acid anhydride (17) in the presence of a base such as pyridine. Compound (22) can be produced even by other methods, for instance, by synthesizing compound (21) from benzotriazole (19) and acid anhydride (20) by using the method described in *J. Org. Chem.*, 62, 726 (1997), and then reacting the compound (21) with compound (16), or by synthesizing compound (24) from 2-pyridinol (23) and acid anhydride (20) by using the method described in *Bull. Chem. Soc. Jpn.*, 63, 2252, and then reacting the compound (24) with compound (16).

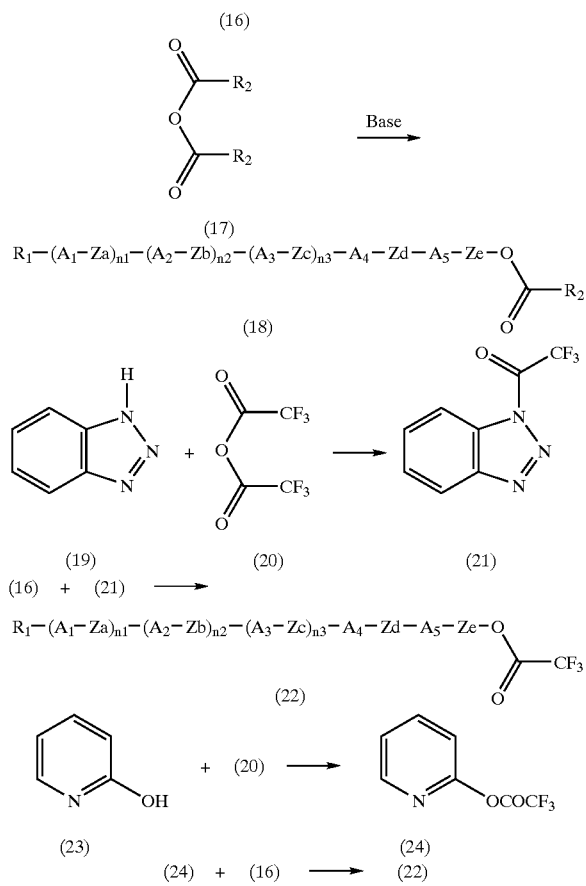

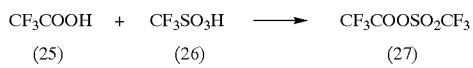

Compound (30) expressed by the general formula (1) wherein Ze is single bond and $A_5$ is 1-cyclohexene-1,4-diyl can be produced by synthesizing compound (27) from trifluoroacetic acid (25) and compound (26) by using the method described in *J. Org. Chem.*, 44, 313 (1979), and then reacting the compound (27) with a cyclohexanone (28) and compound (29).

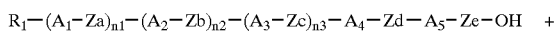

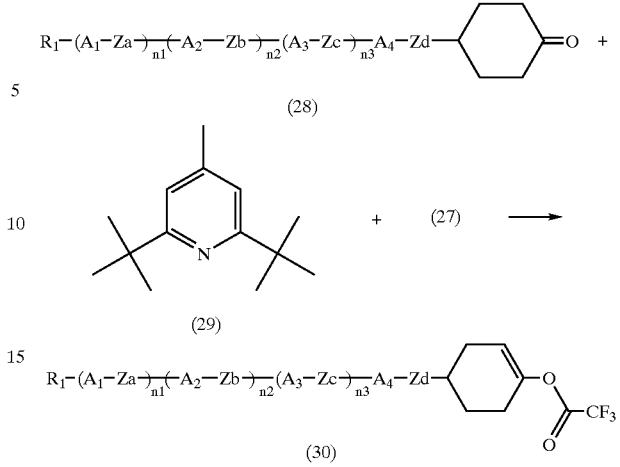

wherein $R_1$, $R_2$, $A_1$ to $A_5$, Za to Ze, n1 to n3, $Y_1$, and $Y_2$ have the same meaning as described above.

EXAMPLES

Now, the present invention will be described in more detail with reference to the examples. However, it should be understood that the scope of the present invention is by no means restricted by such specific examples.

In each of the examples, C indicates crystal, S: smectic phase, N: nematic phase, and I: isotropic liquid phase.

Example 1

Preparation of trifluoroacetic acid 4-(4-propyl-cyclohexyl)cyclohexyl ester (the compound expressed by the general formula (1) wherein n1, n2, and n3 are 0, $R_1$ is n-propyl group, $A_4$ and $A_5$ are 1,4-cyclohexylenes, Zd and Ze are single bonds, $Y_1$ and $Y_2$ are oxygen atoms, and $R_2$ is trifluoromethyl group; Compound No. 3)

First Step

Benzotriazole in an amount of 45.0 g (378 mmol) was dissolved in 400 ml of tetrahydrofuran (hereinafter abbreviated to THF), and 120 g (571 mmol) of trifluoroacetic acid anhydride was added dropwise thereto while being stirred at room temperature. After the solution was stirred at the same temperature for 30 minutes, THF and unreacted trifluoroacetic acid anhydride were distilled off under a reduced pressure to give 80 g (372 mmol) of trifluoroacetylbenzotriazole.

Second Step

Trifluoroacetylbenzotriazole thus obtained in an amount of 11.5 g (53.4 mmol) was dissolved in 100 ml of THF, 10.0 g (44.6 mmol) of 4-(4-propylcyclohexyl)cyclohexanol was added thereto, they were subjected to a reflux for 1 hour, and then the solvent was distilled off. After the residue was purified by column chromatography on silica gel (eluent: heptane/ethyl acetate=8/1), the solvent was distilled off, and the residue was subjected twice to recrystallization by using heptane to give 5.1 g (15.9 mmol) of trifluoroacetic acid 4-(4-propylcyclohexyl)cyclohexyl ester. Yield of this compound based on 4-(4-propylcyclohexyl)cyclohexanol was 35.7%.

$^1$H-NMR (CDCl$_3$) δ (ppm): 5.01~4.69 (m, 1H), 2.15~0.79 (m, 26H); $^{19}$F-NMR (CDCl$_3$) δ (ppm): −75.90 (s, 3F); C-SB 37.7° C., SB-I 56.7° C.

Example 2

Preparation of trifluoroacetic acid 4-(4-propyl-cyclohexyl)cyclohexylmethyl ester (compound expressed by the general formula (1) wherein n1, n2, and n3 are 0, $R_1$ is n-propyl group, $A_4$ and $A_5$ are 1,4-cyclohexylenes, Zd is single bond, Ze is —$CH_2$—, $Y_1$ and $Y_2$ are oxygen atoms, and $R_2$ is trifluoromethyl group; Compound No. 31)

First Step

Trifluoroacetylbenzotriazole obtained in the first step of Example 1 in an amount of 6.0 g (27.9 mmol) was dissolved in 50 ml of THF, 3.0 g (12.6 mmol) of 4-(4-propylcyclohexyl)cyclohexyl-methanol was added thereto, they were subjected to a reflux for 1 hour and 15 minutes, and then the solvent was distilled off. After the residue was purified by column chromatography on silica gel (eluent: heptane/ethyl acetate=8/1), the solvent was distilled off, and the residue was subjected twice to recrystallization by using heptane to give 2.0 g (5.98 mmol) of trifluoroacetic acid 4-(4-propylcyclohexyl)cyclohexyl-methyl ester. Yield of this compound based on 4-(4-propyl-cyclohexyl)cyclohexylmethanol was 47.5%.

$^1$H-NMR (CDCl$_3$) δ (ppm): 4.18~4.12 (d, 2H), 1.84~0.88 (m, 27H); $^{19}$F-NMR (CDCl$_3$) δ (ppm): −75.55 (s, 3F); SX-I 35.9° C.

Example 3

Preparation of trifluoroacetic acid 4-(4-ethyl-cyclohexyl)cyclohexyl ester (compound expressed by the general formula (1) wherein n1, n2, and n3 are 0, $R_1$ is ethyl group, $A_4$ and $A_5$ are 1,4-cyclohexylenes, Zd and Ze are single bonds, $Y_1$ and $Y_2$ are oxygen atoms, and $R_2$ is trifluoromethyl group; Compound No. 2)

First Step

Trifluoroacetylbenzotriazole in an amount of 4.0 g (18.6 mmol) was dissolved in 50 ml of THF, 2.3 g (10.9 mmol) of 4-(4-ethylcyclohexyl)cyclohexanol was added thereto, they were subjected to a reflux for 1 hour, and then the solvent was distilled off. After the residue was purified by column chromatography on silica gel (eluent: heptane/ethyl acetate=8/1), the solvent was distilled off, and the residue was subjected twice to recrystallization by using heptane to give 1.8 g (5.9 mmol) of trifluoroacetic acid 4-(4-ethylcyclohexyl)cyclohexyl ester. Yield of this compound based on 4-(4-ethylcyclohexyl)cyclohexanol was 54%.

$^1$H-NMR (CDCl$_3$) δ (ppm): 4.95~4.72 (d, 1H), 2.16~0.79 (m, 24H); $^{19}$F-NMR (CDCl$_3$) δ (ppm): −75.78 (s, 3F); SX-I 28.4° C.

Example 4

Preparation of trifluoroacetic acid 4-(4-(4-propylphenyl)cyclohexyl)cyclohexyl ester (compound expressed by the general formula (1) wherein n1 and n2 are 0, n3 is 1, $R_1$ is n-propyl group, $A_3$ is 1,4-phenylene, $A_4$ and $A_5$ are 1,4-cyclohexylenes, Zc, Zd, and Ze are single bonds, $Y_1$ and $Y_2$ are oxygen atoms, and $R_2$ is trifluoromethyl group; Compound No. 251)

First Step

Grignard reagent was prepared from 2.43 g (0.10 mol) of dried magnesium and 24.6 g (0.10 mol) of 4-propyliodobenzene in THF, and 100 ml of solution of 21.4 g (0.09 mol) of bicyclohexanedione monoethylene ketal in THF was added dropwise thereto and stirred at room temperature for 3 hours. The reaction solution was added in 300 ml of 3N hydrochloric acid, and the product thus formed was extracted with diethyl ether. After the extract was washed with saturated aqueous sodium bicarbonate solution and water in this turn, the solvent was distilled off under a reduced pressure. To the residue were added 30 ml of toluene and 80 ml of formic acid, and the mixture was refluxed for 3 hours. To the reaction solution was added 100 ml of water and the product thus formed was extracted with toluene. After the extract was washed with saturated aqueous sodium bicarbonate solution and water in this turn, the solvent was distilled off under a reduced pressure. After the residue was purified by column chromatography on silica gel (eluent: heptane/ethyl acetate=4/1), the solvent was distilled off to give 9.5 g (32 mmol) of 1-(4-propylphenyl)-4-(4-oxocyclohexyl)-1-cyclohexene. Yield of this compound was 36%.

Second Step

The 1-(4-propylphenyl)-4-(4-oxocyclohexyl)-1-cyclohexene described above in an amount of 9.5 g (32 mmol) was dissolved in mixed solvent of 200 ml of THF and 50 ml of ethanol, and cooled down to 0° C. Sodium borohydride in an amount of 1.2 g (32 mmol) was gradually added thereto and the mixture was stirred at the same temperature for 1 hour. The reaction solution was added in 150 ml of 1N hydrochloric acid and extracted with diethyl ether. After the extract was washed with saturated aqueous sodium bicarbonate solution and water in this turn, the solvent was distilled off under a reduced pressure. The residue was dissolved in 80 ml of mixed solvent of ethanol/ethyl acetate (1/1), the solution was subjected to a hydrogenation by using Raney Nickel catalyst, and then the catalyst was filtered off. The solvent was distilled off and then the residue was recrystallized by using toluene to give 2.5 g (8.3 mmol) of 4-(4-(4-hydroxycyclohexyl)cyclohexyl)-1-propylbenzene. Yield of this compound was 26%.

Third Step

Trifluoroacetylbenzotriazole described above in an amount of 4.0 g (18.6 mmol) was dissolved in 50 ml of THF, 2.5 g (8.3 mmol) of 4-(4-(4-hydroxycyclohexyl)cyclohexyl)-1-propylbenzene was added thereto, they were refluxed for 1 hour, and then the solvent was distilled off. After the residue was purified by column chromatography on silica gel (eluent: heptane/ethyl acetate=3/1), the solvent was distilled off. The residue was subjected twice to recrystallization by using mixed solvent of heptane/ethyl acetate (1/5) to give 1.2 g (3.0 mmol) of trifluoroacetic acid 4-(4-(4-propylphenyl)cyclohexyl)cyclohexyl ester. Yield of this compound was 36%.

$^1$H-NMR (CDCl$_3$) δ (ppm): 7.09 (s, 4H), 4.97~4.74 (m, 1H), 2.64~0.85 (m, 26H); $^{19}$F-NMR (CDCl$_3$) δ (ppm): −75.74 (s, 3F); C-SX 18.6° C., SX-SB 72.9° C., SB-N 122.7° C., N-I 146.5° C.

Example 5

Preparation of trifluoroacetic acid 4-(4-butylcyclohexyl)cyclohexyl ester (compound expressed by the general formula (1) wherein n1, n2, and n3 are 0, $R_1$ is n-butyl group, $A_4$ and $A_5$ are 1,4-cyclohexylenes, Zd and Ze are single bonds, $Y_1$ and $Y_2$ are oxygen atoms, and $R_2$ is trifluoromethyl group; Compound No. 1)

First Step

Trifluoroacetylbenzotriazole in an amount of 7.5 g (35 mmol) was dissolved in 75 ml of THF, 4.6 g (19 mmol) of 4-(4-butyl-cyclohexyl)cyclohexanol was added thereto, they were refluxed for 1 hour, and then the solvent was distilled off. After the residue was purified by column chromatography on silica gel (eluent: heptane/ethyl acetate=5/1), the solvent was distilled off, the residue was subjected twice to recrystallization by using heptane to give 1.5 g (4.5 mmol) of trifluoroacetic acid 4-(4-butylcyclohexyl)cyclohexyl ester. Yield of this compound based on 4-(4-butylcyclohexyl)cyclohexanol was 24%.

SB-N 37.4° C., N-I 40.1° C.

Example 6

Preparation of trifluoroacetic acid 2-(4-(4-propylcyclohexyl)cyclohexyl)ethyl ester (compound expressed by the general formula (1) wherein n1, n2, and n3 are 0, $R_1$ is n-propyl group, $A_4$ and $A_5$ are 1,4-cyclohexylenes, Zd is single bond, Ze is —$CH_2CH_2$—, $Y_1$ and $Y_2$ are oxygen atoms, and $R_2$ is trifluoromethyl group; Compound No. 34)
First Step Trifluoroacetylbenzotriazole in an amount of 7.0 g (33 mmol) was dissolved in 70 ml of THF, 5.0 g (20 mmol) of 2-(4-(4-propylcyclohexyl)cyclohexyl)ethanol was added thereto, they were refluxed for 1 hour, and then the solvent was distilled off. After the residue was purified by column chromatography on silica gel (eluent: heptane/ethyl acetate= 5/1), the solvent was distilled off, and the residue was subjected twice to recrystallization by using heptane to give 2.9 g (8.3 mmol) of trifluoroacetic acid 2-(4-(4-propylcyclohexyl)cyclohexyl)-ethyl ester. Yield of this compound based on 2-(4-(4-propylcyclohexyl)cyclohexyl)ethanol was 42%.

C-I 39.5° C.

Example 7

Preparation of difluoroacetic acid 4-(4-ethylcyclohexyl)-cyclohexyl ester (compound expressed by the general formula (1) wherein n1, n2, and n3 are 0, $R_1$ is ethyl group, $A_4$ and $A_5$ are 1,4-cyclohexylenes, Zd and Ze are single bonds, $Y_1$ and $Y_2$ are oxygen atoms, and $R_2$ is difluoromethyl group; Compound No. 5)
First Step In 30 ml of dichloromethane were dissolved 2.2 g (11 mmol) of 4-(4-ethylcyclohexyl)cyclohexanol, 1.9 g (20 mmol) of difluoroacetic acid, and 0.8 g (8 mmol) of triethylamine, and this solution was cooled down to 0° C. To this solution was added dropwise 15 ml of solution of 2.4 g (12 mmol) of dicyclohexylcarbodiimide (DCC) in dichloromethane, and the mixture was stirred at the same temperature for 1 hour and then at room temperature for 17 hours. After the crystals in the suspension thus obtained were filtered off, the solvent was distilled off under a reduced pressure. After the residue was purified by column chromatography on silica gel (eluent: heptane/toluene=1/1), the solvent was distilled off, and the residue was subjected twice to recrystallization to give 1.4 g (4.9 mmol) of difluoroacetic acid 4-(4-ethylcyclohexyl)-cyclohexyl ester. Yield of this compound based on 4-(4-ethylcyclohexyl)cyclohexanol was 45%.

$^1$H-NMR (CDCl$_3$) δ (ppm): 5.85 (t, 1H), 4.93~4.63 (m, 1H), 2.12~0.79 (m, 24H); C-I 30.1° C.

Example 8

Preparation of difluoroacetic acid 4-(4-propylcyclohexyl)-cyclohexyl ester (compound expressed by the general formula (1) wherein n1, n2, and n3 are 0, $R_1$ is propyl group, $A_4$ and $A_5$ are 1,4-cyclohexylenes, Zd and Ze are single bonds, $Y_1$ and $Y_2$ are oxygen atoms, and $R_2$ is difluoromethyl group; Compound No. 4)
First Step In 40 ml of dichloromethane were dissolved 3.0 g (13 mmol) of 4-(4-propylcyclohexyl)cyclohexanol, 2.3 g (24 mmol) of difluoroacetic acid, and 0.9 g (9 mmol) of triethylamine, and this solution was cooled down to 0° C. To this solution was added dropwise 20 ml of solution of 3.1 g (15 mmol) of DCC in dichloromethane, and the mixture was stirred at the same temperature for 1 hour and at room temperature for 17 hours. After the crystals in the suspension thus obtained were filtered off, the solvent was distilled off under a reduced pressure. After the residue was purified by column chromatography on silica gel (eluent: heptane/toluene=1/1), the solvent was distilled off, and the residue was subjected twice to recrystallization by using heptane to give 2.0 g (6.6 mmol) of difluoroacetic acid 4-(4-propylcyclohexyl)cyclohexyl ester. Yield of this compound based on 4-(4-propylcyclohexyl)-cyclohexanol was 51%.

$^1$H-NMR (CDCl$_3$) δ (ppm): 5.85 (t, 1H), 4.96~4.63 (m, 1H), 2.13~0.79 (m, 26H); C-I 68.9° C.

Example 9

Preparation of trifluoroacetic acid 4-(4-propylcyclohexyl)-1-cyclohexenyl ester (compound expressed by the general formula (1) wherein n1, n2, and n3 are 0, $R^1$ is propyl group, $A_4$ is 1,4-cyclohexylene, $A_5$ is 1-cyclohexene-1,4-diyl, Zd and Ze are single bonds, $Y_1$ and $Y_2$ are oxygen atoms, and $R_2$ is trifluoromethyl group; Compound No. 121)
First Step To 50 ml of carbon tetrachloride were added 3.9 g (18 mmol) of 4-(4-propylcyclohexyl)cyclohexanone and 3.8 g (19 mmol) of 2,6-di-t-butyl-4-methylpyridine, and the mixture was stirred at room temperature. To this mixture was added dropwise 2 ml of solution of 4.5 g (18 mmol) of trifluoroacetyltriflate in carbon tetrachloride. Subsequently, 25 ml of carbon tetrachloride was added thereto and the mixture was stirred at room temperature for 1 hour. The reaction solution was filtered off and then the filtrate was concentrated under a reduced pressure. After the residue was purified by column chromatography on silica gel (eluent: heptane/toluene=3/1), the solvent was distilled off, and the residue was subjected twice to recrystallization by using heptane to give 1.3 g (4.1 mmol) of trifluoroacetic acid 4-(4-propylcyclohexyl)-1-cyclohexenyl ester. Yield of this compound based on 4-(4-propylcyclohexyl)cyclohexanone was 23%.

$^1$H-NMR (CDCl$_3$) δ (ppm): 5.59~5.51 (m, 1H), 2.27~0.79 (m, 24H); C-I 40.5° C.

Example 10

Preparation of trifluoroacetic acid 4-(4-(4-butylcyclohexyl)cyclohexyl)-1-cyclohexenyl ester (compound expressed by the general formula (1) wherein n1 and n2 are 0, n3 is 1, $R_1$ is n-butyl group, $A_3$ and $A_4$ are 1,4-cyclohexylenes, $A_5$ is 1-cyclohexene-1,4-diyl, Zc, Zd, and Ze are single bonds, $Y_1$ and $Y_2$ are oxygen atoms, and $R_2$ is trifluoromethyl group; Compound No. 341)
First Step To 200 ml of carbon tetrachloride were added 5.4 g (17 mmol) of 4-(4-(4-n-butylcyclohexyl)cyclohexyl) cyclohexanone and 3.8 g (19 mmol) of 2,6-di-t-butyl-4-methylpyridine, and the mixture was stirred at room temperature. To this mixture was added dropwise 5 ml of solution of 4.5 g (18 mmol) of trifluoro-acetyltriflate in carbon tetrachloride, and the mixture was stirred for 30 minutes. The reaction solution was filtered and the filtrate was concentrated under a reduced pressure. After the residue was purified by column chromatography on silica gel (eluent: heptane/toluene=1/1), the solvent was distilled off, and the residue was subjected twice to recrystallization by using heptane to give 1.6 g (3.9 mmol) of trifluoroacetic acid 4-(4-(4-propylcyclohexyl)cyclohexyl)-1-cyclohexenyl ester. Yield of this compound based on 4-(4-(4-n-butylcyclohexyl)-cyclohexyl)cyclohexanone was 23%.

¹H-NMR (CDCl₃) δ (ppm): 5.60~5.52 (m, 1H), 2.19~0.88 (m, 36H); C-SX1 10.5° C., SX1–SX2 58.7° C., SX2-SB 108.2° C., SB-N 154.6° C., N-I 186.8° C.

Example 11

Preparation of trifluoroacetic acid 4-(4-(4-butyl-cyclohexyl)cyclohexyl)cyclohexyl ester (compound expressed by the general formula (1) wherein n1 and n2 are 0, n3 is 1, $R_1$ is n-butyl group, $A_3$, $A_4$, and $A_5$ are 1,4-cyclohexylenes, Zc, Zd, and Ze are single bonds, $Y_1$ and $Y_2$ are oxygen atoms, and $R_2$ is trifluoromethyl group; Compound No. 232)

First Step

To 100 ml of THF was added 3.0 g (9.4 mmol) of 4-(4-(4-butylcyclohexyl)cyclohexyl)cyclohexanol, and then 5.0 g (24 mmol) of trifluoroacetic acid anhydride was added dropwise thereto at room temperature. After the mixture was stirred for 1 hour, the solvent was distilled off. After the residue was purified by column chromatography on silica gel (eluent: heptane/ethyl acetate=5/1), the solvent was distilled off, and the residue was subjected twice to recrystallization by using heptane to give 1.3 g (3.1 mmol) of trifluoroacetic acid 4-(4-(4-butylcyclohexyl)cyclohexyl)cyclohexyl ester. Yield of this compound based on 4-(4-(4-butylcyclohexyl)cyclohexyl)-cyclohexanol was 33%.

C-SX 37.8° C., SX-SB 163.9° C., SB-N 172.8° C., N-I 225.9° C.

Example 12

Preparation of trifluoroacetic acid 4-(4-(5-butyl-1,3-dioxane-2-yl)cyclohexyl)cyclohexyl ester (compound expressed by the general formula (1) wherein n1 and n2 are 0, n3 is 1, $R_1$ is n-butyl group, $A_3$ is 1,3-dioxane-2,5-diyl, $A_4$ and $A_5$ are 1,4-cyclohexylenes, Zc, Zd, and Ze are single bonds, $Y_1$ and $Y_2$ are oxygen atoms, and $R_2$ is trifluoromethyl group; Compound No. 241)

First Step

Dried methoxymethyltriphenylphosphonium chloride in an amount of 210 g (613 mmol) was added in 1.5 l of THF and the solution was cooled down to −20° C., and 68.5 g (610 mmol) of potassium-t-butoxide was gradually added thereto at the same temperature. After it was warmed up to room temperature and stirred for 2 hours, 700 ml of 119 g (500 mmol) of bicyclohexanedione monoethylene ketal in THF was added dropwise thereto at the same temperature and the mixture was stirred for 5 hours. After 1 l of water was added to the reaction mixture, the product thus formed was extracted with ether, the extract was washed with water, and then the solvent was distilled off. After the residue was purified by column chromatography on silica gel (eluent: heptane/ethyl acetate =3/1), the solvent was distilled off. After the solution was refluxed in 200 ml of formic acid for 3 hours, 300 ml of water was added to the reaction solution, the product thus formed was extracted with toluene, the extract was washed with water, saturated aqueous sodium bicarbonate solution, and water in this turn, and then dried over magnesium sulfate. After the solvent was distilled off and the residue was purified by column chromatography (eluent: toluene/ethyl acetate=1/1), the solvent was distilled off to give 43.0 g (207 mmol) of 4-(4-oxocyclohexyl)-cyclohexanecarbaldehyde. Yield of this compound based on bicyclohexanedione monoethylene ketal was 41.4%.

Second Step

To 300 ml of toluene were added 20.2 g (97.0 mmol) of the 4-(4-oxocyclohexyl)cyclohexanecarbaldehyde described above, 12.8 g (96.8 mmol) of 2-n-butyl-1,3-propanediol, and 1 g of p-toluenesulfonic acid, and the mixture was refluxed by using a Dean-Stark for 2 hours. Water in an amount of 200 ml was added to the reaction solution, the product thus formed was extracted with toluene, the extract was washed with saturated aqueous bicarbonate solution and water in this turn, and then the solvent was distilled off. After the residue was purified by column chromatography on silica gel (eluent: heptane/ethyl acetate=5/1), the solvent was distilled off. The residue was Silo recrystallized from ethanol to give 3.2 g (9.9 mmol) of 2-(4-(4-oxocyclohexyl)-cyclohexyl)-5-n-butyl-1,3-dioxane. Yield of this compound based on 4-(4-oxocyclohexyl)cyclohexanecarbaldehyde was 10%.

Third Step

In 50 ml of ethanol was dissolved 3.2 g (9.9 mmol) of the 2-(4-(4-oxocyclohexyl)cyclohexyl)-5-n-butyl-1,3-dioxane, and the solution was cooled down to 0° C. To this solution was added gradually 0.19 g (5.0 mmol) of sodium borohydride such that the liquid temperature did not exceed 15° C., and the mixture was stirred for 1 hour. Water in an amount of 50 ml was added to the reaction mixture, the product thus formed was extracted with ether, the extract was washed with 1N-hydrochloric acid and water in this turn, and the solvent was distilled off. After the residue was purified by column chromatography on silica gel (eluent: heptane/ethyl acetate=2/1), the solvent was distilled off. The residue was recrystallized from ethanol to give 1.2 g (3.7 mmol) of 2-(4-(4-hydroxy-cyclohexyl)cyclohexyl)-5-n-butyl-1,3-dioxane. Yield of this compound based on 2-(4-(4-oxocyclohexyl)cyclohexyl-5-n-butyl-1,3-dioxane was 37%.

Fourth Step

To 30 ml of THF was added 1.2 g (3.7 mmol) of the 2-(4-(4-hydroxycyclohexyl)cyclohexyl)-5-n-butyl-1,3-dioxane described above, and then 1.0 g (4.8 mmol) of trifluoroacetic acid anhydride was added thereto at room temperature. After the mixture was stirred for 1 hour, the solvent was distilled off. After the residue was purified by column chromatography on silica gel (eluent: heptane/ethyl acetate=3/1), the solvent was distilled off, and the residue was subjected twice to recrystallization by using heptane to give 0.70 g (1.7 mmol) of trifluoroacetic acid 4-(4-(5-butyl-1,3-dioxane-2-yl)cyclohexyl)-cyclohexyl ester. Yield of this compound based on 2-(4-(4-hydroxycyclohexyl)-cyclohexyl)-5-n-butyl-1,3-dioxane was 46%.

¹H-NMR (CDCl₃) δ (ppm): 5.00~4.68 (m, 1H), 4.17~3.98 (m, 3H), 3.39~3.14 (m, 2H), 2.15~0.81 (m, 29H).

Example 13

Preparation of trifluoroacetic acid 4-(4-(4-butyl-cyclohexyl)-1-cyclohexenyl)cyclohexyl ester (compound expressed by the general formula (1) wherein n1 and n2 are 0, n3 is 1, $R_1$ is n-butyl group, $A_3$ and $A_5$ are 1,4-cyclohexylenes, $A_4$ is 1-cyclohexene-1,4-diyl, Zc, Zd, and Ze are single bonds, $Y_1$ and $Y_2$ are oxygen atoms, and $R_2$ is trifluoromethyl group; Compound No. 343)

First Step

To the Grignard reagent which was prepared from 2.31 g (95.1 mmol) of dried magnesium and 25.0 g (95.0 mmol) of 4-benzyloxy-bromobenzene in 300 ml of THF, was added dropwise 100 ml of solution of 21.0 g (88.8 mmol) of 4-(4-n-butylcyclohexyl)-cyclohexanone in THF at room temperature, and the mixture was stirred at the same temperature for 12 hours. The reaction solution was added to 500 ml of 0.5N hydrochloric acid, the product thus formed was extracted with ether, the extract was washed with saturated aqueous sodium bicarbonate solution and water in this turn, and then the solvent was distilled off. After the residue was purified by column chromatography on silica gel (eluent: toluene), the solvent was distilled off, and the residue was recrystallized from toluene to give 11.8 g (28.1 mmol) of 4-(4-(4-n-butyl-cyclohexyl(-1-hydroxycyclohexyl)-1-benzyloxybenzene. Yield of this compound based on 4-(4-n-butylcyclohexyl)cyclohexanone was 31.6%.

Second Step

To 350 ml of cyclohexane were added 11.8 g (28.1 mmol) of the 4-(4-(4-n-butylcyclohexyl)-1-hydroxycyclohexyl)-1-benzyloxybenzene described above and 1.0 g of Pd—Na/C catalyst, and subjected to a hydrogenation in an autoclave at 110° C. for 2 hours. Then, the catalyst was filtered off, and the solvent was distilled off to give 7.7 g of the residue. This residue and 1.0 g of para-toluenesulfonic acid were added to 100 ml of toluene, and the mixture was refluxed by using a Dean-Stark. The reaction solution was cooled down to room temperature, 100 ml of water was added thereto, the product thus formed was extracted with toluene, the extract was washed with saturated aqueous sodium bicarbonate solution and water in this turn, and then the solvent was distilled off. After the residue was purified by column chromatography on silica gel (eluent: toluene), the solvent was distilled off to give 4.0 g (13 mmol) of 4-(4-(4-n-butylcyclohexyl)-1-cyclohexenyl)cyclohexanone. Yield of this compound based on 4-(4-(4-n-butylcyclohexyl)-1-hydroxycyclohexyl)-1-benzyloxybenzene was 46%.

Third Step

In 50 ml of ethanol was dissolved 4.0 g (13 mmol) of the 4-(4-(4-n-butylcyclohexyl)-1-cyclohexenyl)cyclohexanone described above, and the solution was cooled down to 0° C. Sodium borohydride in an amount of 0.25 g (6.6 mmol) was gradually added thereto such that the liquid temperature did not exceed 15° C., and the mixture was stirred for 1 hour. Water in an amount of 50 ml was added to the reaction solution, the product thus formed was extracted with ether, the extract was washed with 1N hydrochloric acid and water in this turn, and then the solvent was distilled off. After the residue was purified by column chromatography on silica gel (eluent: heptane/ethyl acetate=3/1), the solvent was distilled off. The residue was recrystallized from ethanol to give 1.6 g (5.0 mmol) of 4-(4-(4-n-butylcyclohexyl)-1-cyclohexenyl)cyclohexanol. Yield of this compound based on 4-(4-(4-n-butylcyclohexyl)-1-cyclohexenyl)-cyclohexanone was 38%.

Fourth Step

To 30 ml of THF was added 1.6 g (5.0 mmol) of the 4-(4-(4-n-butylcyclohexyl)-1-cyclohexeneyl)cyclohexanol described above, and then 1.6 g (7.6 mmol) of trifluoroacetic acid anhydride was added dropwise thereto at room temperature. After the mixture was stirred for 1 hour, the solvent was distilled off. After the residue was purified by column chromatography on silica gel (eluent: heptane/toluene=1/1), the solvent was distilled off, and the residue was subjected twice to recrystallization by using heptane to give 1.2 g (2.9 mmol) of trifluoroacetic acid 4-(4-(4-butylcyclohexyl)-1-cyclohexenyl)cyclohexyl ester. Yield of this compound based on 4-(4-(4-n-butylcyclohexyl)-1-cyclohexenyl) cyclohexanol was 58%.

$^1$H-NMR (CDCl$_3$) δ (ppm): 5.41 (m, 1H), 5.00~4.68 (m, 1H), 2.17~0.88 (m, 34H); SX-SB 87.9° C., SB-N 129.4° C., N-I 171.5° C.

Example 14

Preparation of trifluoroacetic acid 4-(4-(2-(4-pentyl-cyclohexyl)ethyl)-3-cyclohexenyl)cyclohexyl ester (compound expressed by the general formula (1) wherein n1 and n2 are 0, n3 is 1, R$_1$ is n-pentyl group, A$_3$ and A$_5$ are 1,4-cyclohexylenes, A$_4$ is 3-cyclohexene-1,4-diyl, Zc is —CH$_2$CH$_2$—, Zd and Ze are single bonds, Y$_1$ and Y$_2$ are oxygen atoms, and R$_2$ is trifluoromethyl group; Compound No. 245)

First Step

To the Grignard reagent which was prepared from 4.80 g (198 mmol) of dried magnesium and 50.0 g (191 mmol) of 2-(4-n-pentylcyclohexyl)bromoethane in 500 ml of THF, was added dropwise 200 ml of solution of 40.0 g (168 mmol) of bicyclohexanedione monoethylene ketal in THF at room temperature, and the mixture was stirred at the same temperature for 12 hours. The reaction solution was added to 500 ml of 0.5N hydrochloric acid, the product thus formed was extracted with ether, the extract was washed with saturated aqueous sodium bicarbonate solution and water in this turn, and then the solvent was distilled off. After the residue was purified by column chromatography on silica gel (eluent: heptane/ethyl acetate=3/1), the solvent was distilled off, the residue was refluxed in 200 ml of formic acid for 3 hours, 200 ml of water was added to the reaction solution, the product thus formed was extracted with toluene, the extract was washed with water, saturated aqueous sodium bicarbonate solution, and water in this turn, and then dried over magnesium sulfate. After the solvent was distilled off and the residue was purified by column chromatography (eluent: heptane/ethyl acetate=1/1), the solvent was distilled off, and the residue was recrystallized from ethanol to give 15.0 g of 4-(4-(2-(4-n-pentylcyclohexyl)-ethyl)-3-cyclohexenyl)-cyclohexanone. Yield of this compound based on bicyclohexanedione monoethylene ketal was 24.9%.

Second Step

To 1 l of mixed solvent of ethanol/THF (4/1) was dissolved 15.0 g (41.8 mmol) of the 4-(4-(2-(4-n-pentylcyclohexyl)ethyl)-3-cyclohexenyl)cyclohexanone described above, and the solution was cooled down to 0° C. To this mixture was gradually added 0.80 g (21.1 mmol) of sodium borohydride such that the liquid temperature did not exceed 15° C., and the mixture was stirred for 1 hour. Water in an amount of 350 ml was added to the reaction solution, the product thus formed was extracted with ether, the extract was washed with 1N-hydrochloric acid and water in this turn, and then the solvent was distilled off. After the residue was purified by column chromatography on silica gel (eluent: heptane/ethyl acetate=3/1), the solvent was distilled off. The residue was recrystallized from ethanol to give 6.0 g (17 mmol) of 4-(4-(2-(4-n-pentyl-cyclohexyl)ethyl)-3-cyclohexenyl)cyclohexanol. Yield of this compound based on 4-(4-(2-(4-n-pentylcyclohexyl)ethyl)-3-cyclohexenyl) cyclohexanone was 41%.

Third Step

To 60 ml of THF was added 3.0 g (8.3 mmol) of the 4-(4-(2-(4-n-pentylcyclohexyl)ethyl)-3-cyclohexenyl) cyclohexanol described above, and 6.0 g (29 mmol) of trifluoroacetic acid anhydride was added dropwise thereto at room temperature. After the mixture was stirred for 1 hour, the solvent was distilled off. After the residue was purified by column chromatography on silica gel (eluent: heptane/ ethyl acetate=5/1), the solvent was distilled off, and the residue was subjected twice to recrystallization by using heptane to give 2.0 g (4.4 mmol) of trifluoroacetic acid 4-(4-(2-(4-pentyl-cyclohexyl)ethyl)-3-cyclohexenyl) cyclohexyl ester. Yield of this compound based on 4-(4-(4-n-butylcyclohexyl)-1-cyclohexenyl)-cyclohexanol was 53%.

$^1$H-NMR (CDCl$_3$) δ (ppm): 5.36 (m, 1H), 4.98~4.71 (m, 1H), 2.20~0.81 (m, 41H); C-SB 74.5° C., SB-N 108.9° C., N-I 133.2° C.

Example 15

Preparation of pentafluoropropionic acid 4-(4-propyl-cyclohexyl)cyclohexyl ester (compound expressed by the general formula (1) wherein n1, n2, and n3 are 0, $R_1$ is n-propyl group, $A_4$ and $A_5$ are 1,4-cyclohexylenes, Zd and Ze are single bonds, $Y_1$ and $Y_2$ are oxygen atoms, and $R_2$ is pentafluoroethyl group; Compound No. 6)

First Step

To 50 ml of THF was added 3.0 g (13 mmol) of 4-(4-propylcyclohexyl)cyclohexanol, and 5.0 g (16 mmol) of pentafluoropropionic acid anhydride was added dropwise thereto at room temperature. After the mixture was stirred for 1 hour, the solvent was distilled off. After the residue was purified by column chromatography on silica gel (eluent: heptane/toluene =1/1), the solvent was distilled off, and the residue was subjected twice to recrystallization by using heptane to give 1.8 g (4.9 mmol) of pentafluoropropionic acid 4-(4-propyl-cyclohexyl)cyclohexyl ester. Yield of this compound based on 4-(4-propylcyclohexyl)cyclohexanol was 38%.

C-SX 25.0° C., SX-I 43.2° C.

Based on the descriptions in the examples 1 through 15 and the section of BEST MODE FOR CARRYING OUT THE INVENTION, following compounds (Compound No. 1 through No. 350) can be produced. In the following, compounds obtained in the examples 1 through 15 are also mentioned again.

No.1
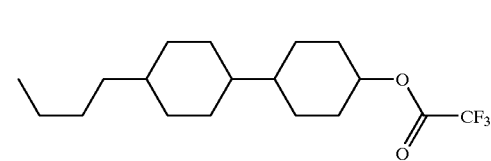

No.2
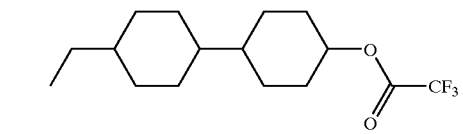

No.3
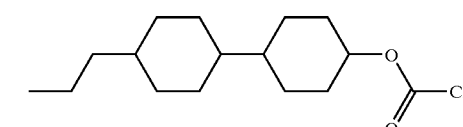

No.4
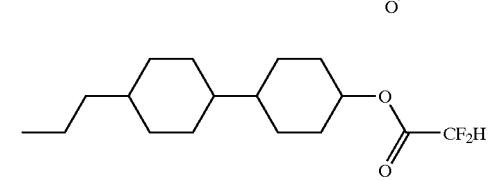

No.5
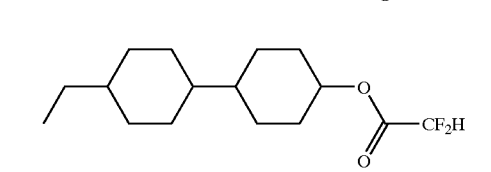

No.6
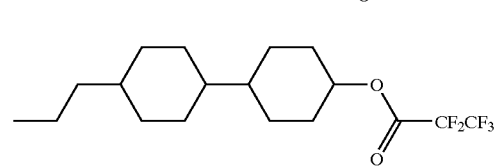

-continued

No.7
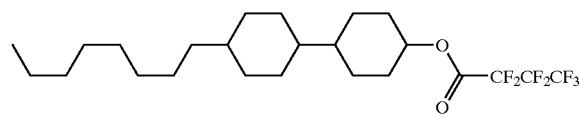

No.8
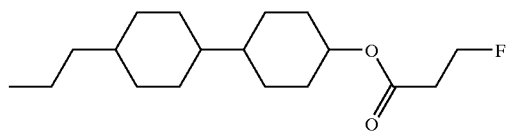

No.9
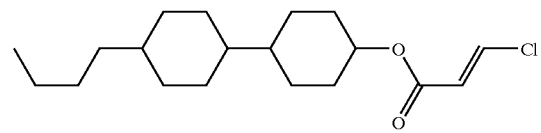

No.10
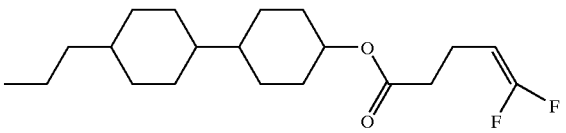

No.11
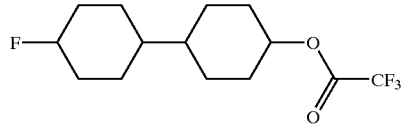

No.12
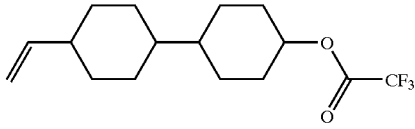

No.13
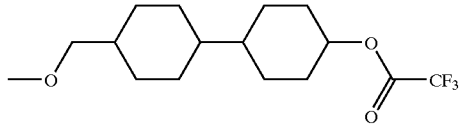

No.14
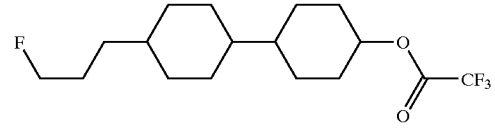

No.15
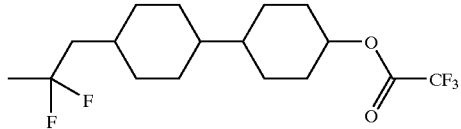

No.16
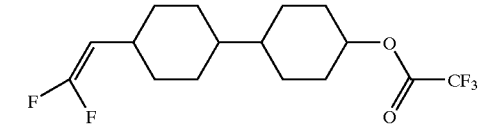

No.17
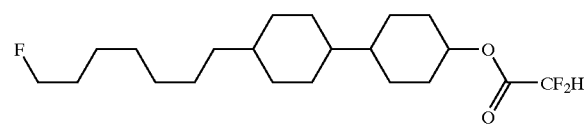

No.18
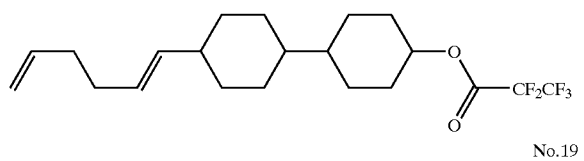
No.19
No.20
No.21
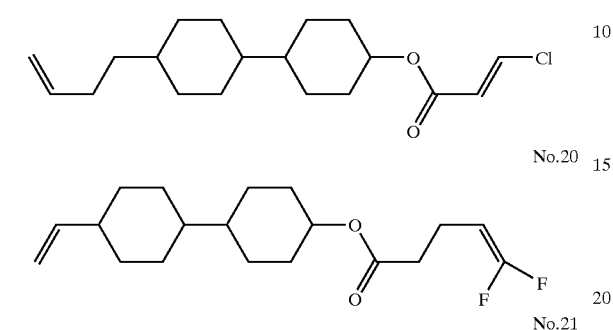
No.22
No.23
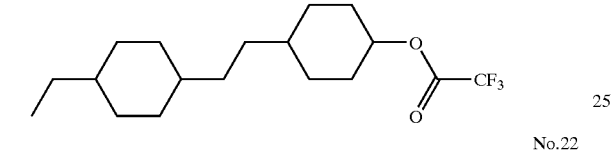
No.24
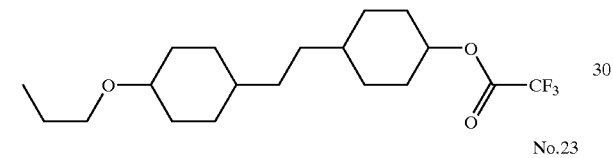
No.25
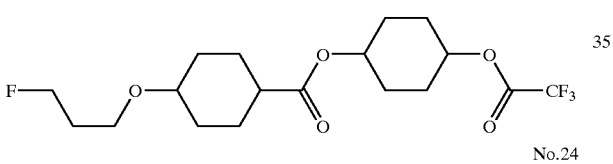
No.26
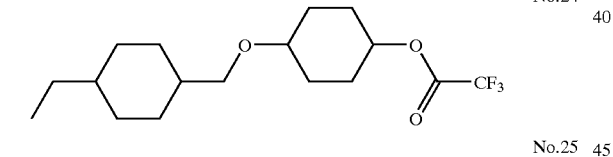
No.27
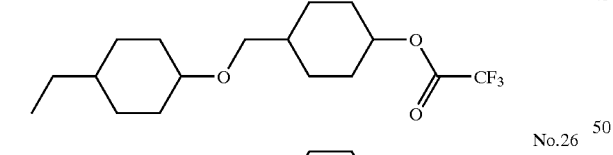
No.28
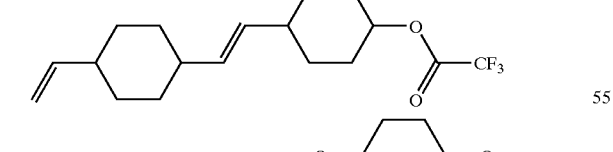
No.29
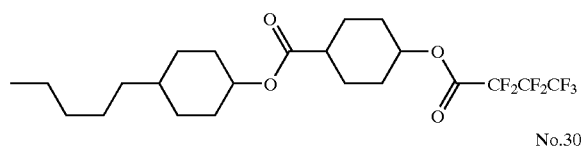
No.30
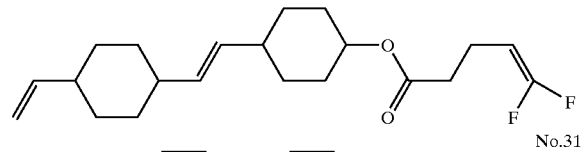
No.31
No.32
No.33
No.34
No.35
No.36
No.37
No.38
No.39

No.40
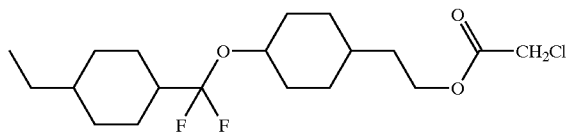
No.41
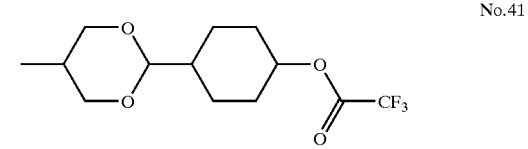
No.42
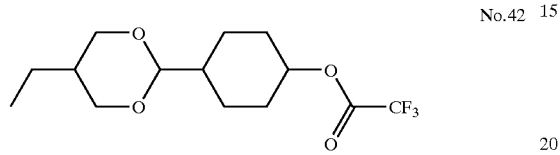
No.43
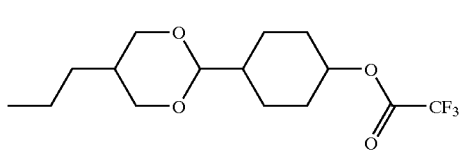
No.44
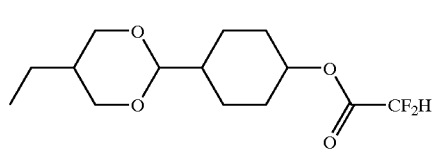
No.45
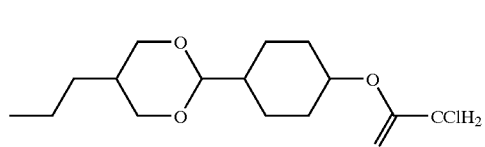
No.46
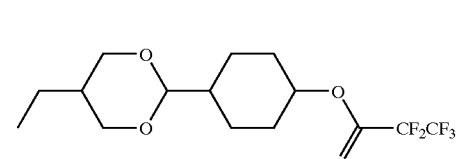
No.47
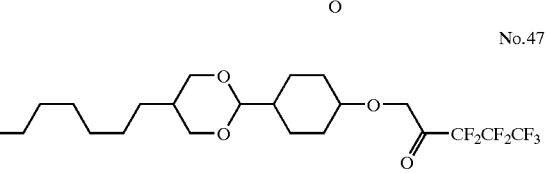
No.48
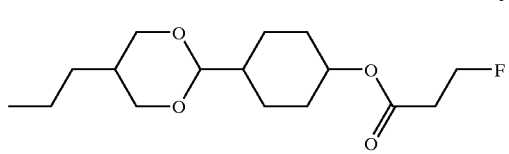
No.49
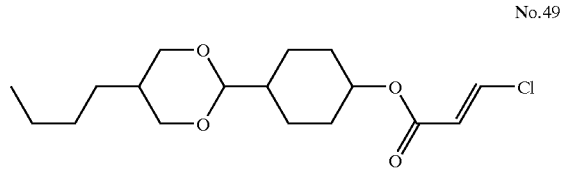
No.50
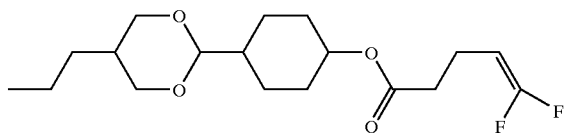
No.51
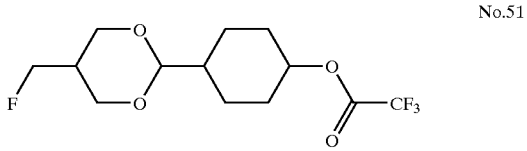
No.52
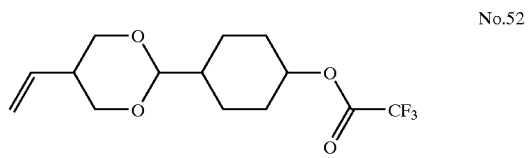
No.53
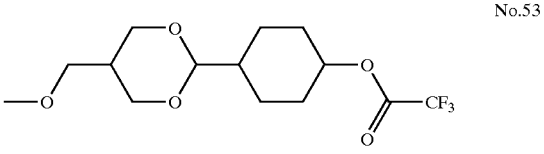
No.54
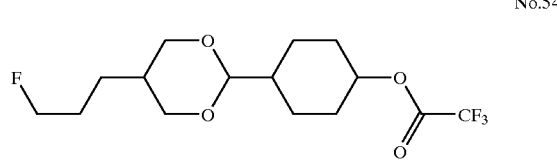
No.55
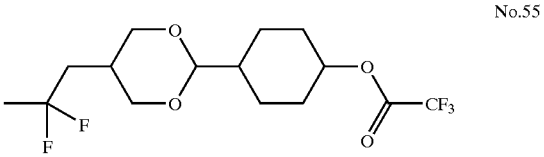
No.56
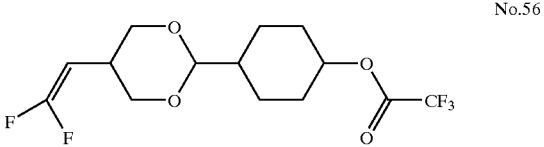
No.57
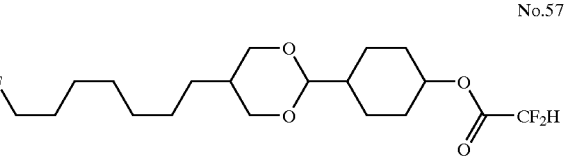
No.58
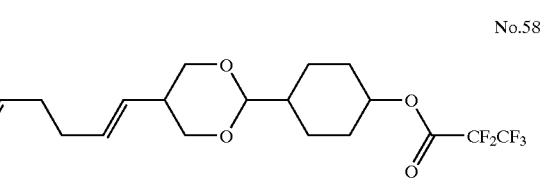
No.59
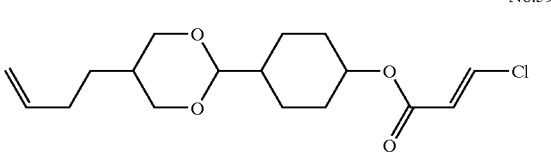

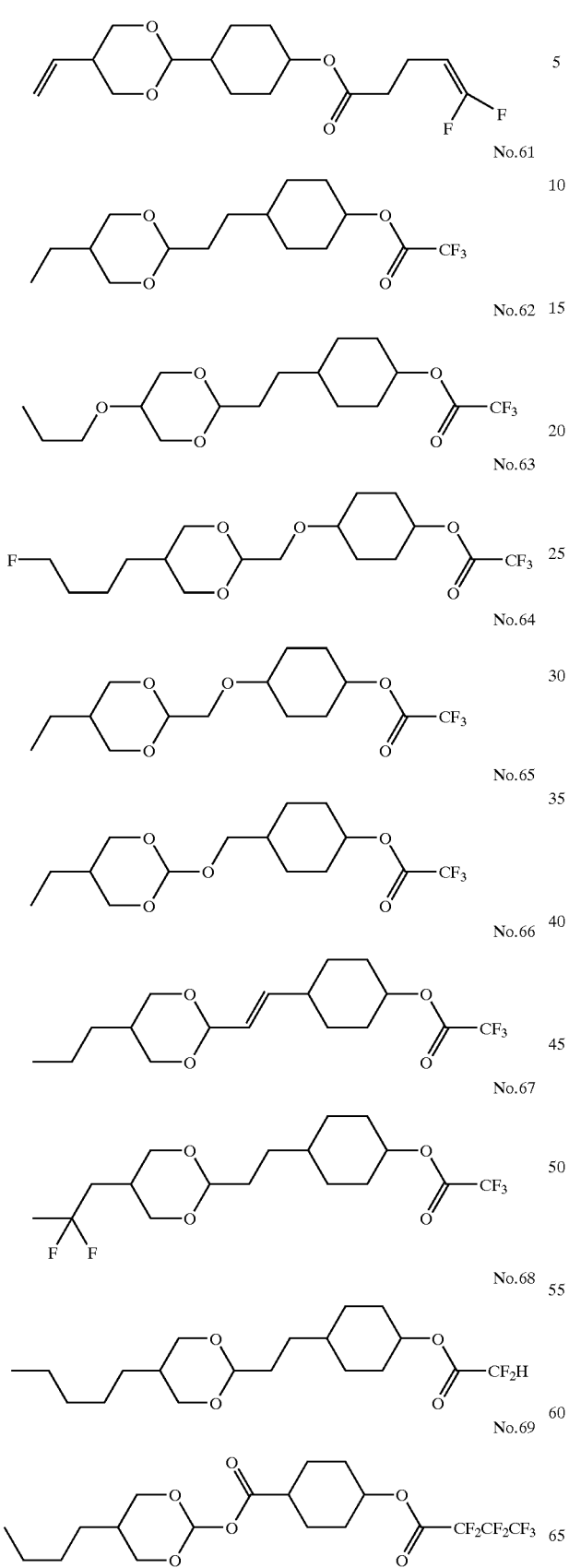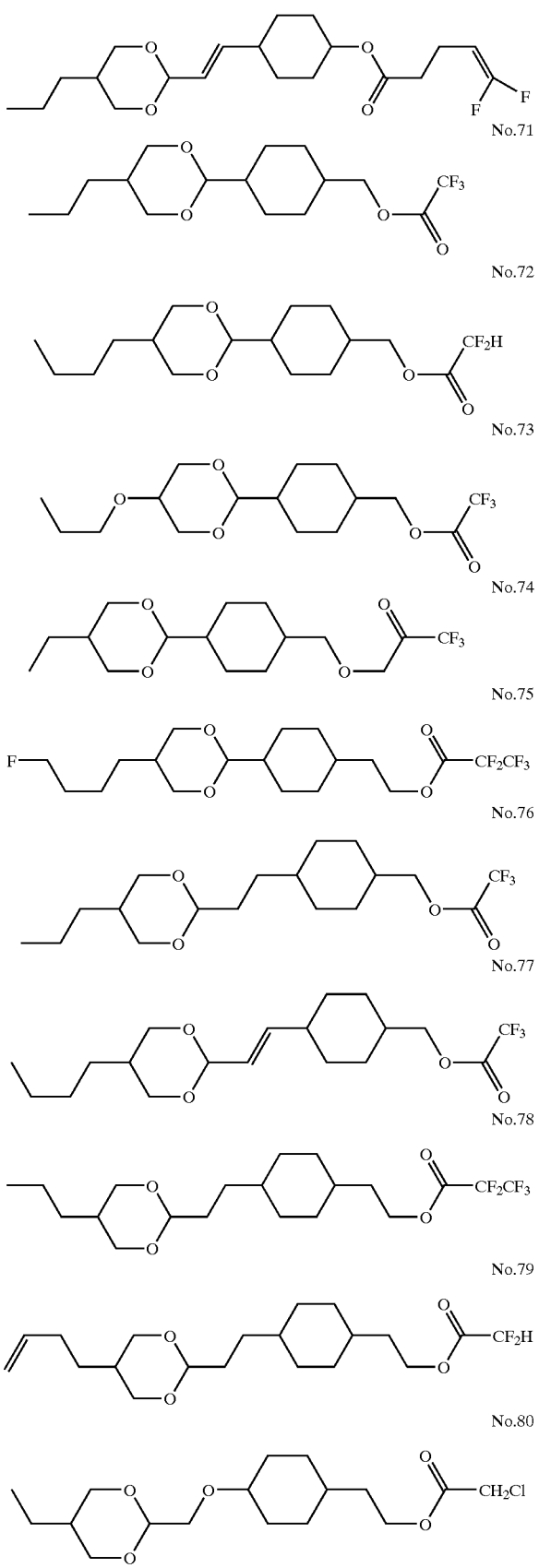

-continued
No.81
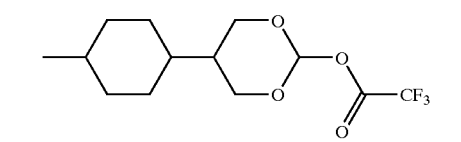
No.82
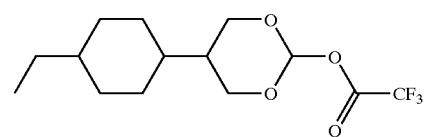
No.83
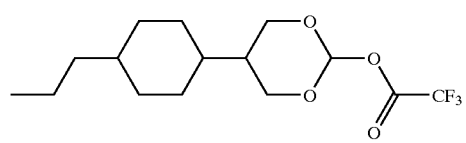
No.84
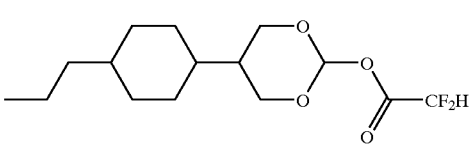
No.85
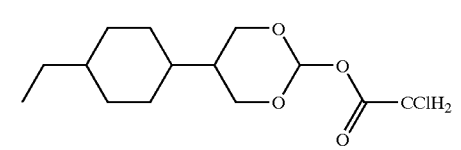
No.86
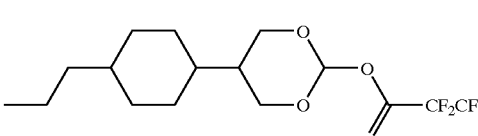
No.87
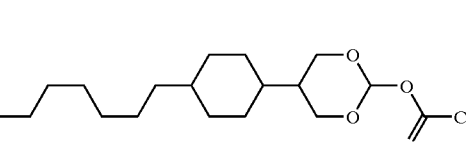
No.88
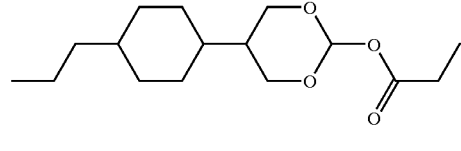
No.89
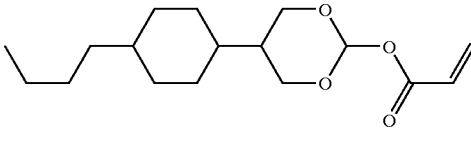
No.90
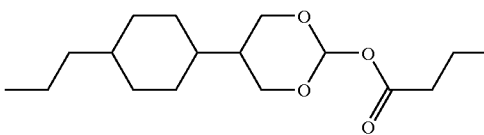
-continued
No.91
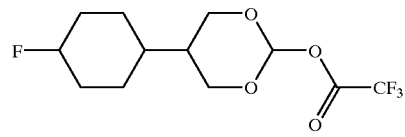
No.92
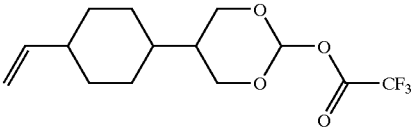
No.93
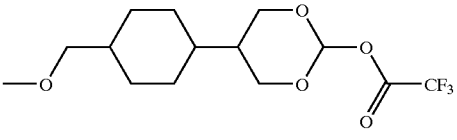
No.94
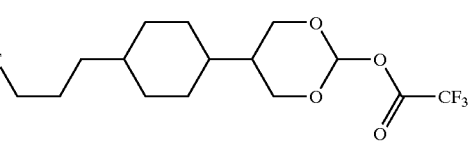
No.95
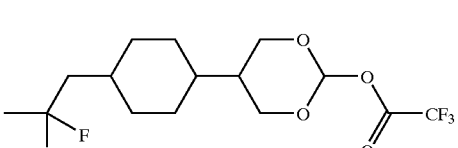
No.96
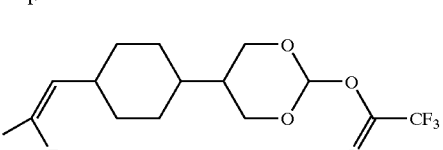
No.97
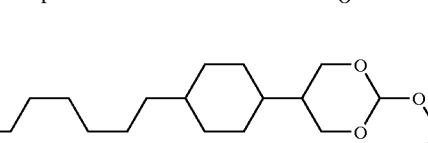
No.98
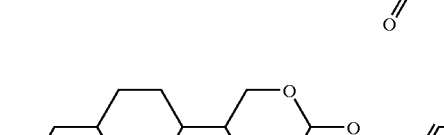
No.99
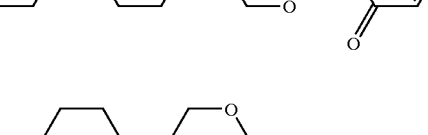
No.100
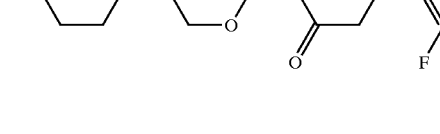

No.101
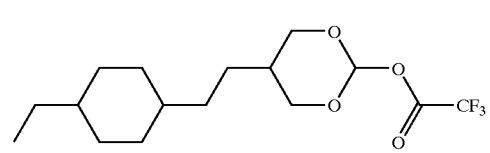
No.102
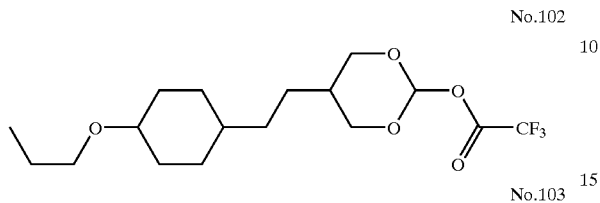
No.103
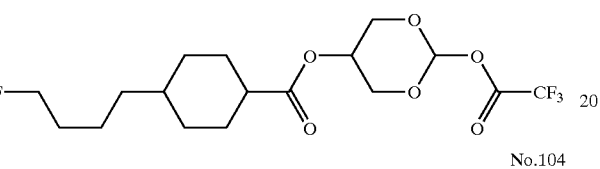
No.104
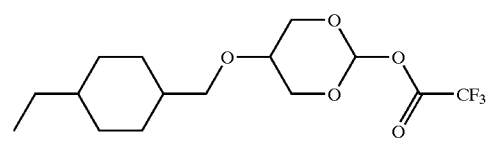
No.105
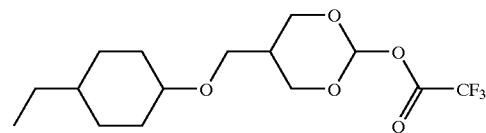
No.106
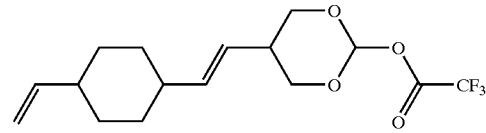
No.107
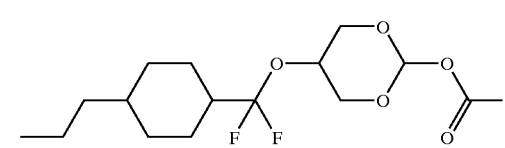
No.108
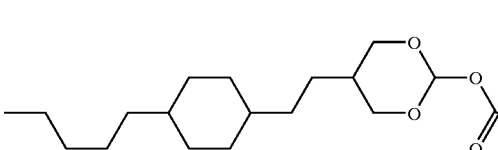
No.109
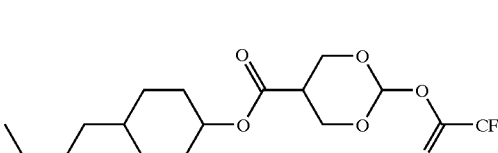
No.110
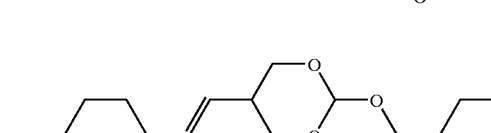
No.111
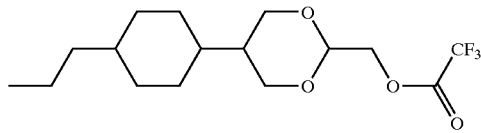
No.112
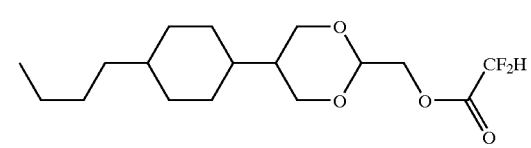
No.113
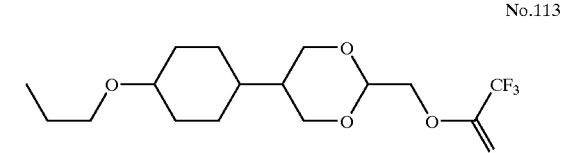
No.114
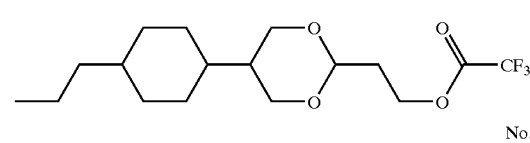
No.115
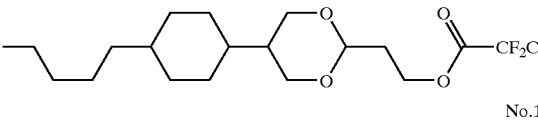
No.116
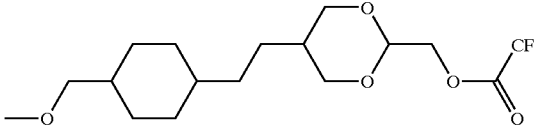
No.117
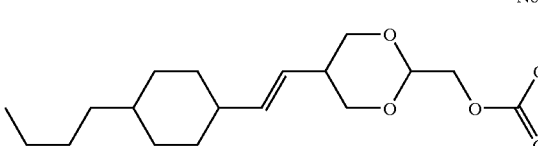
No.118
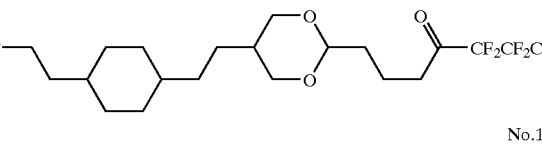
No.119
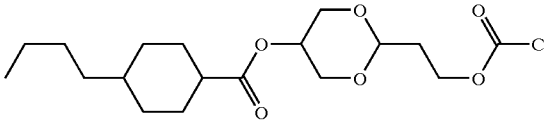
No.120
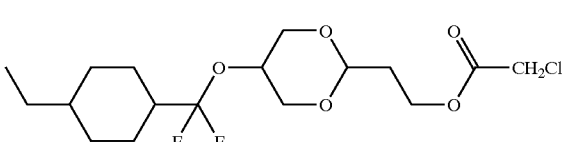

-continued
No.121
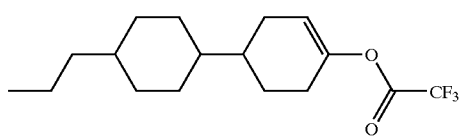
No.122
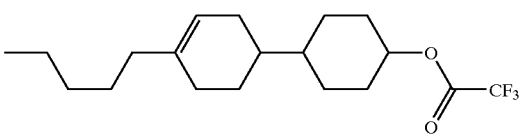
No.123
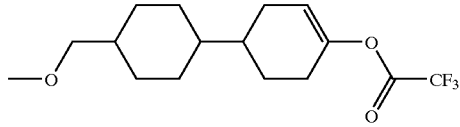
No.124
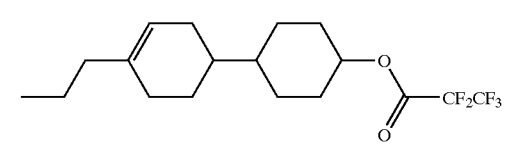
No.125
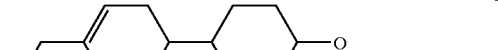
No.126
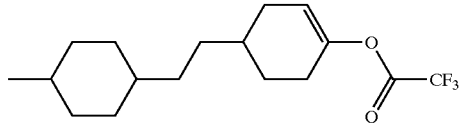
No.127
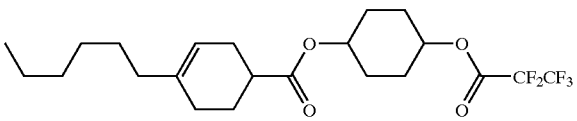
No.128
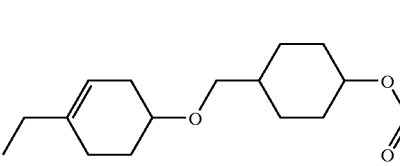
No.129
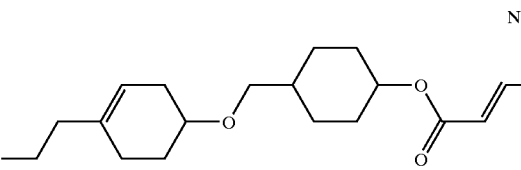
No.130
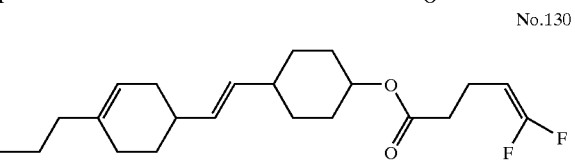
No.131
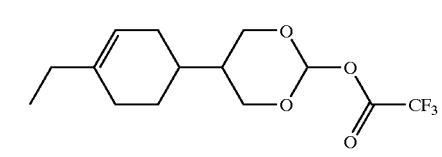
-continued
No.132
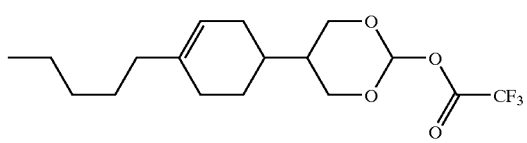
No.133
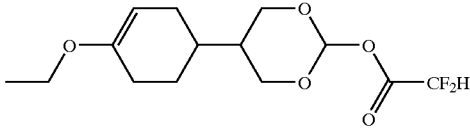
No.134
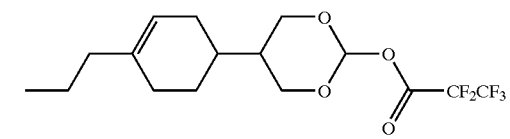
No.135
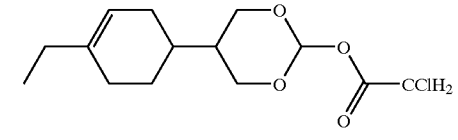
No.136
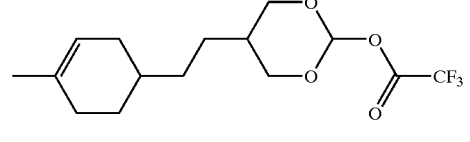
No.137
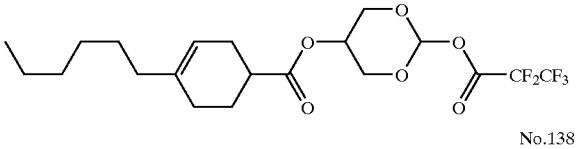
No.138
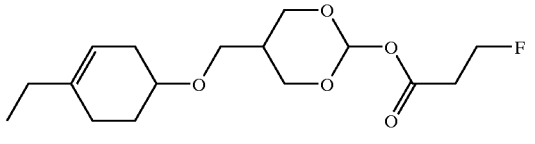
No.139
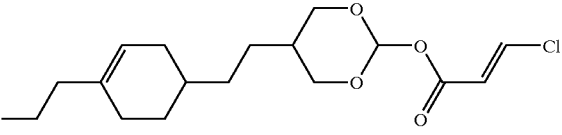
No.140
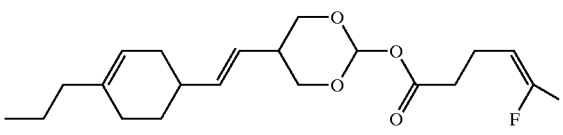
No.141
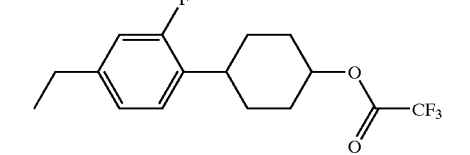

No.142
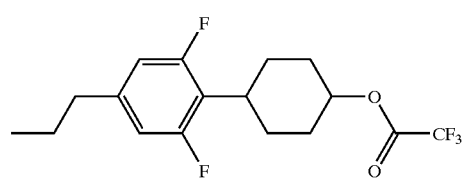
No.143
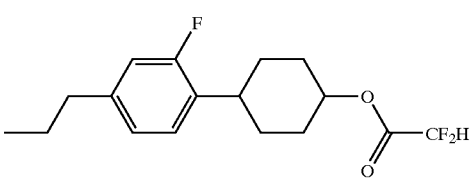
No.144
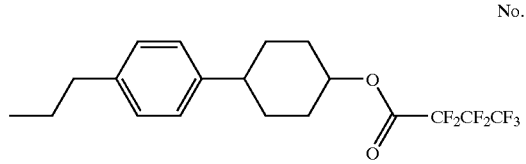
No.145
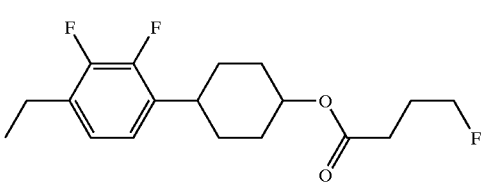
No.146
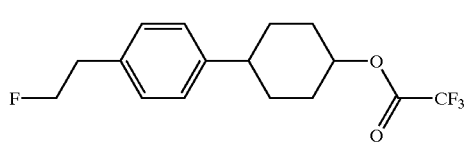
No.147
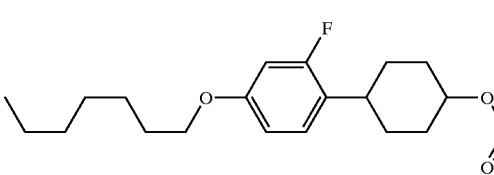
No.148
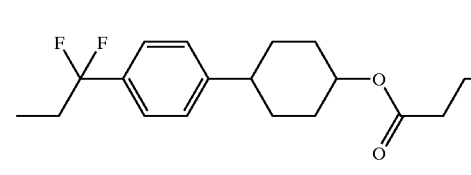
No.149
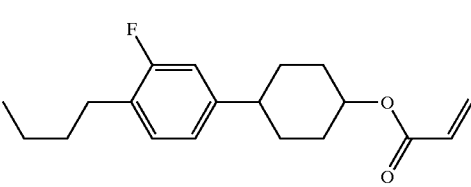
No.150
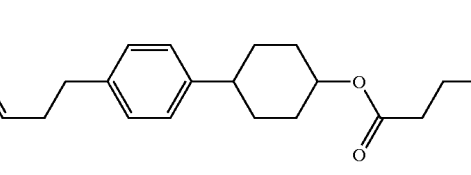
No.151
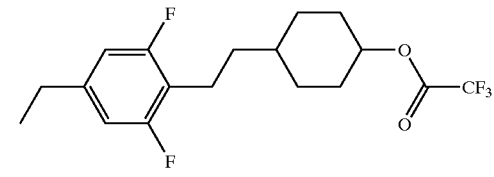
No.152
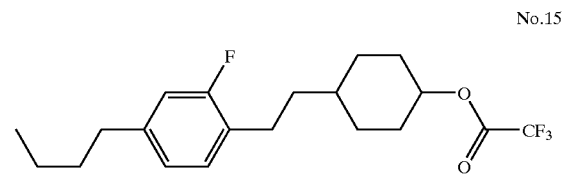
No.153
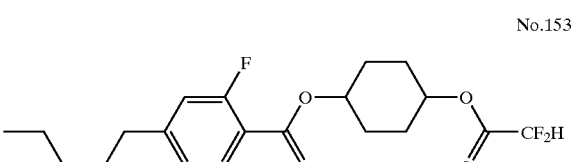
No.154
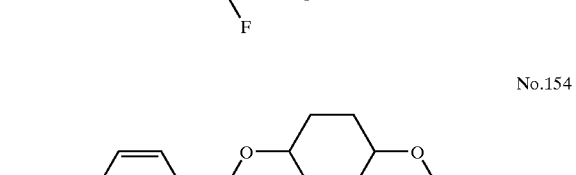
No.155
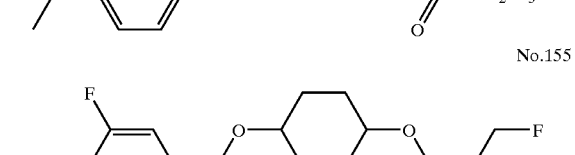
No.156
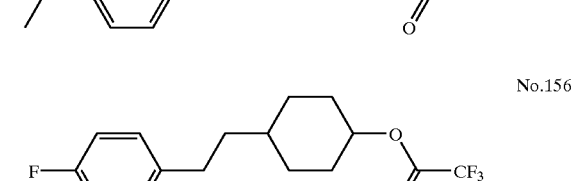
No.157
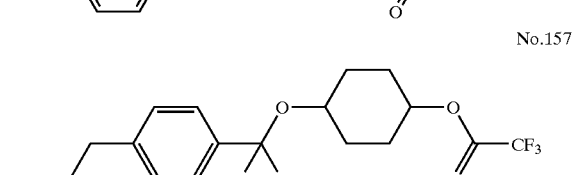
No.158
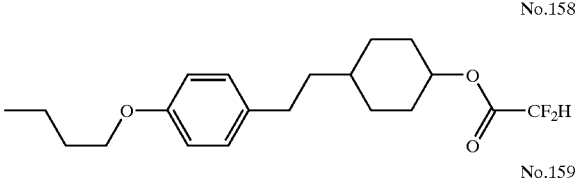
No.159
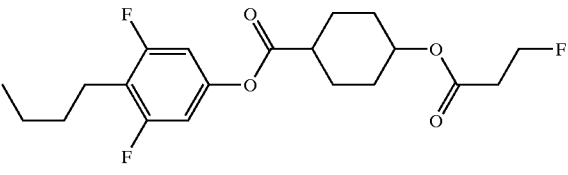

-continued
No.160
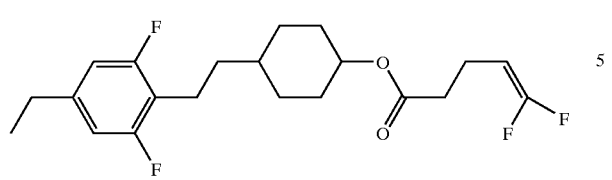
No.161
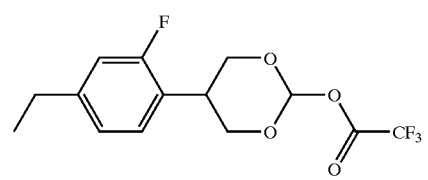
No.162
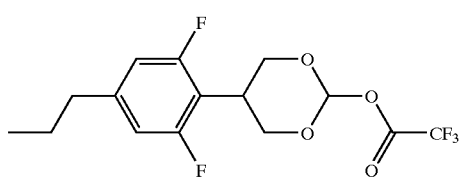
No.163
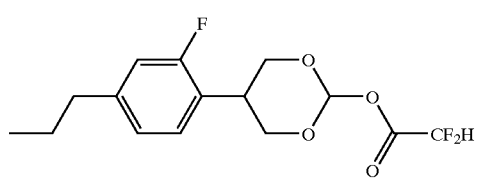
No.164
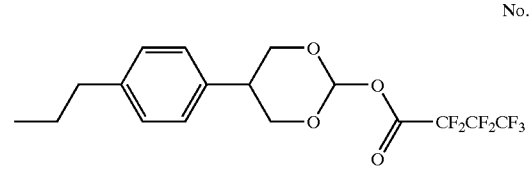
No.165
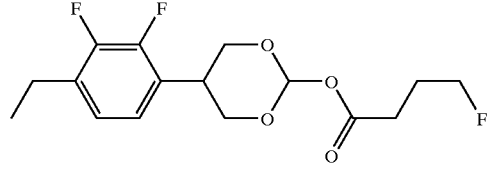
No.166
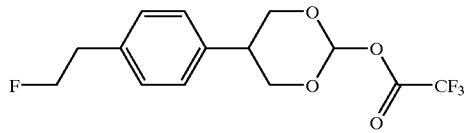
No.167
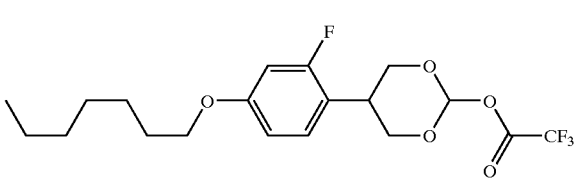
No.168
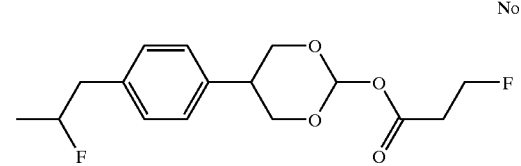
-continued
No.169
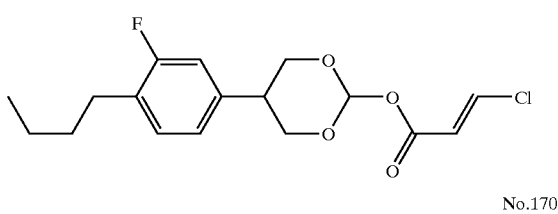
No.170
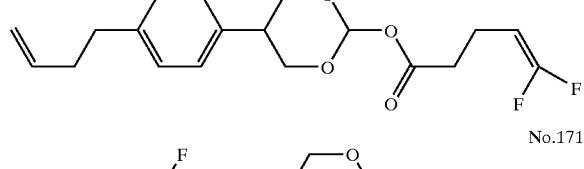
No.171
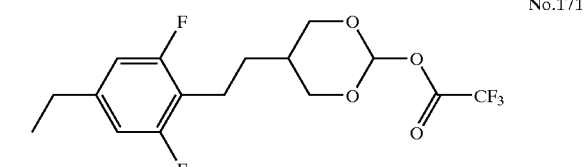
No.172
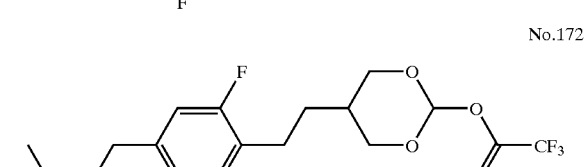
No.173
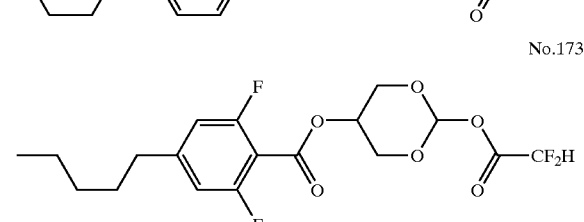
No.174
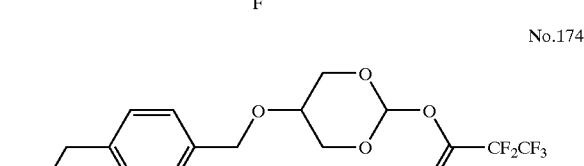
No.175
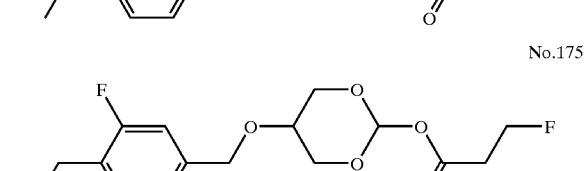
No.176
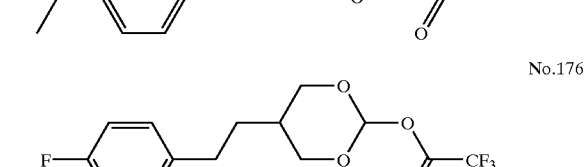
No.177
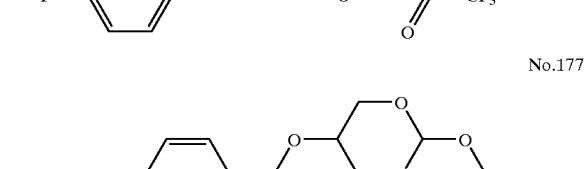
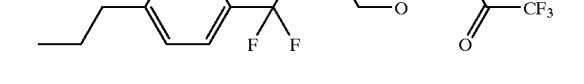

-continued

No.178
No.179
No.180
No.181
No.182
No.183
No.184
No.185

-continued

No.186
No.187
No.188
No.189
No.190
No.191
No.192
No.193

-continued

No.211 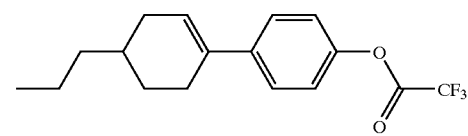
No.212 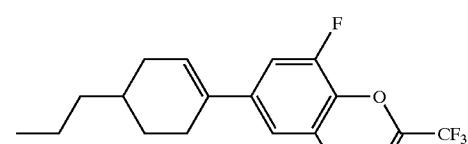
No.213 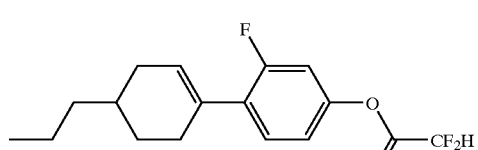
No.214 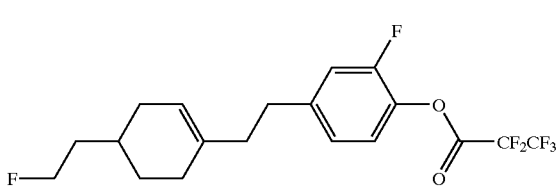
No.215 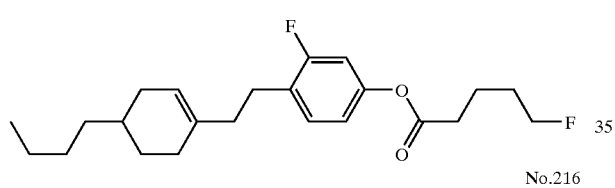
No.216 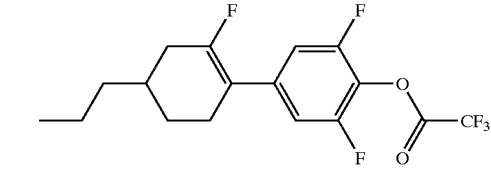
No.217 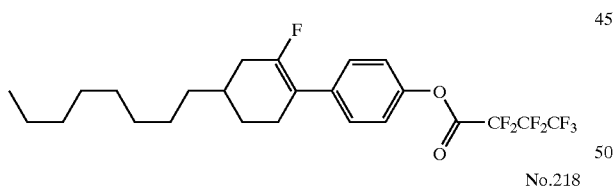
No.218 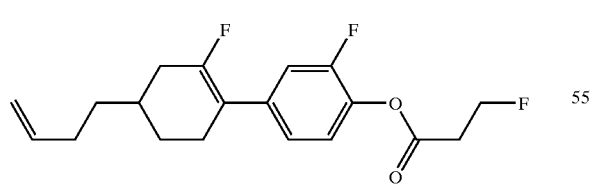
No.219 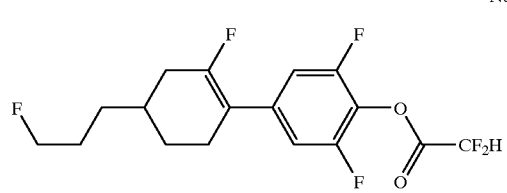
No.220 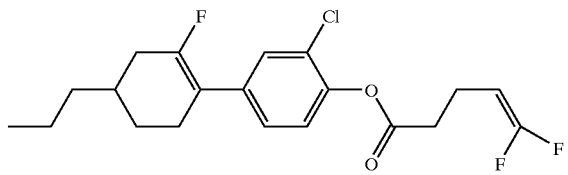
No.221 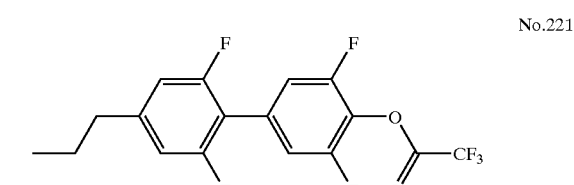
No.222 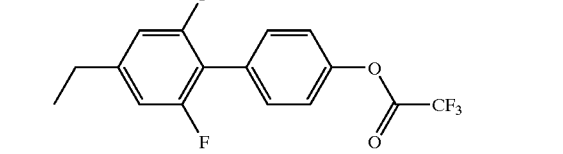
No.223 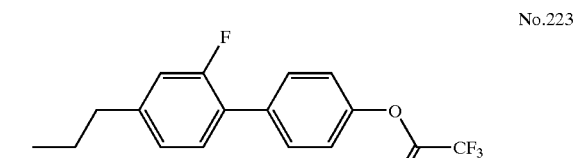
No.224 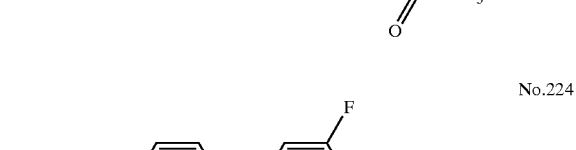
No.225 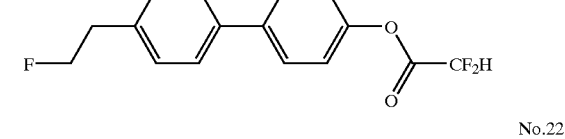
No.226 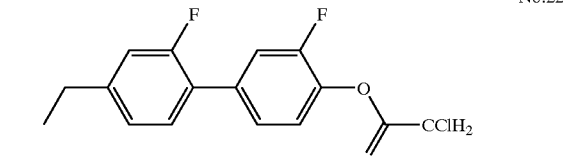
No.227 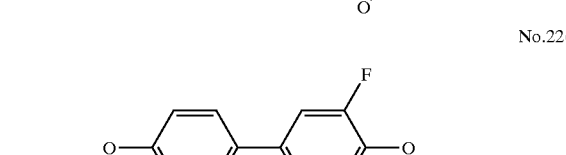

No.228
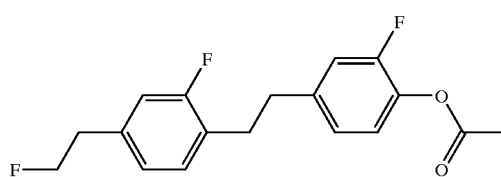
No.229
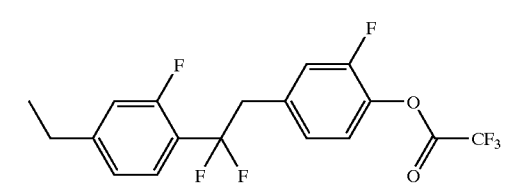
No.230
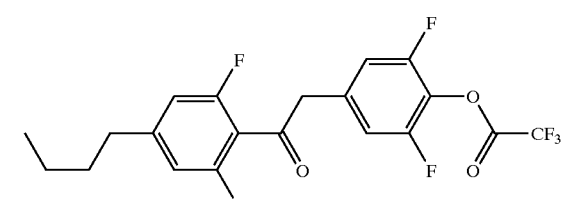
No.231
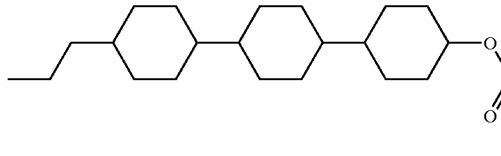
No.232
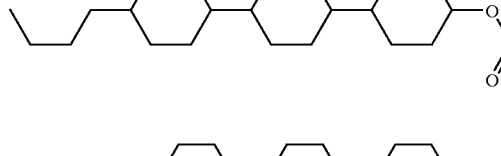
No.233
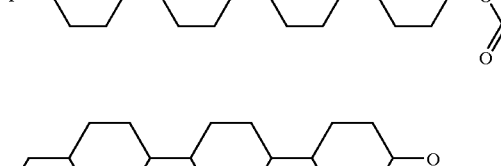
No.234
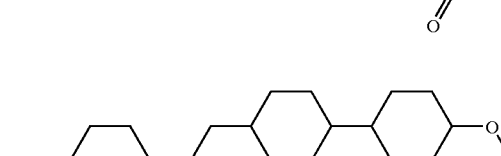
No.235
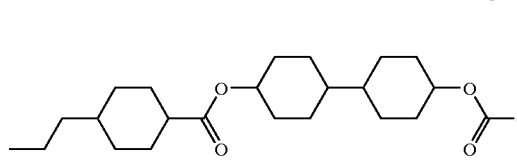
No.236
No.237
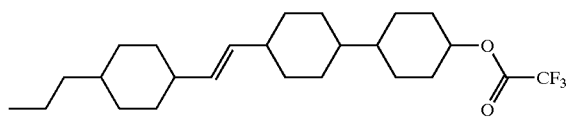
No.238
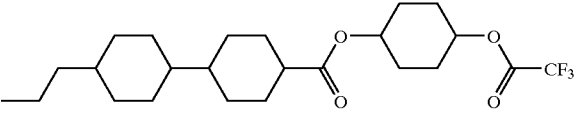
No.239
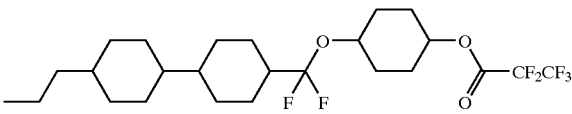
No.240
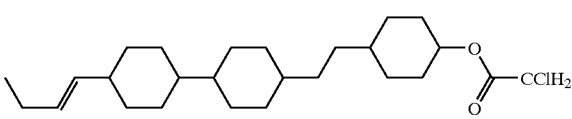
No.241
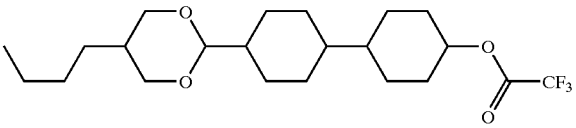
No.242
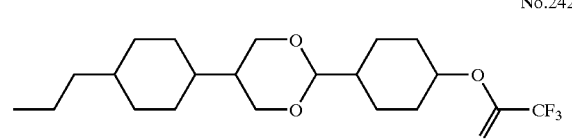
No.243
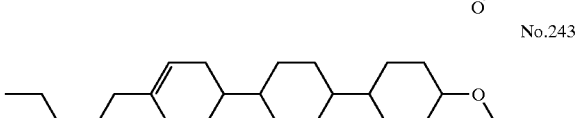
No.244
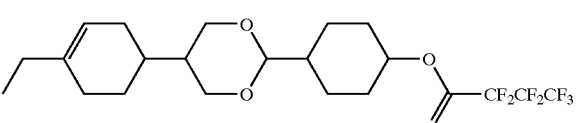
No.245
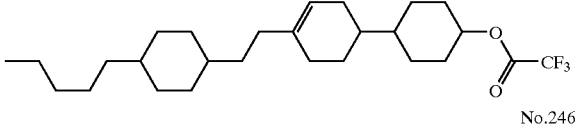
No.246
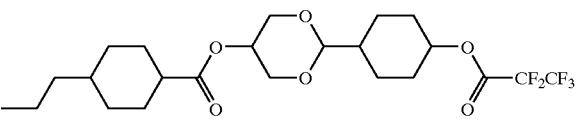
No.247
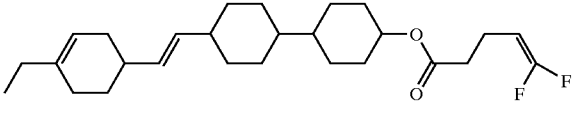

-continued
No.248
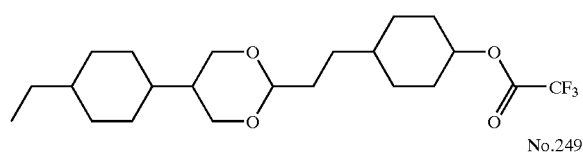
No.249
No.250
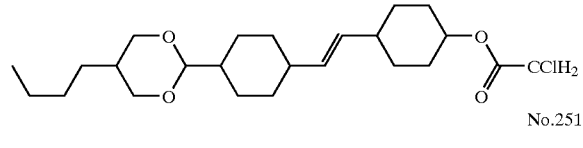
No.251
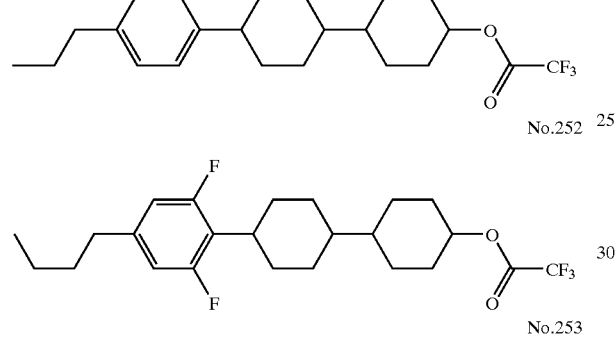
No.252
No.253
No.254
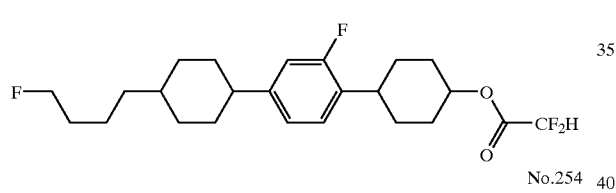
No.255
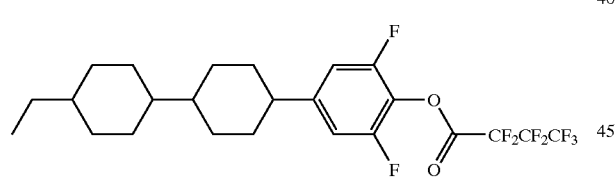
No.256
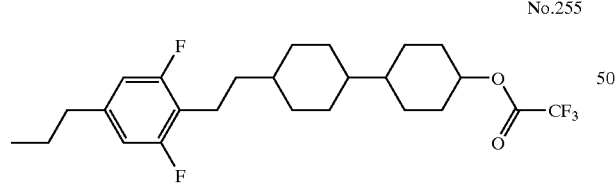
No.257
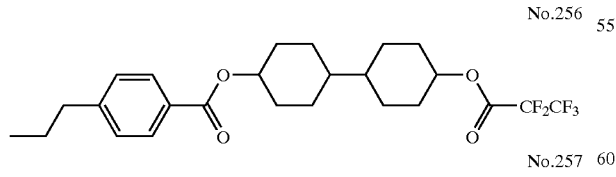
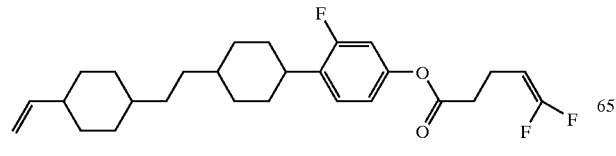
-continued
No.258
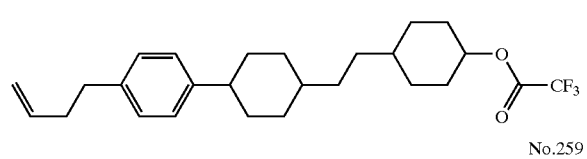
No.259
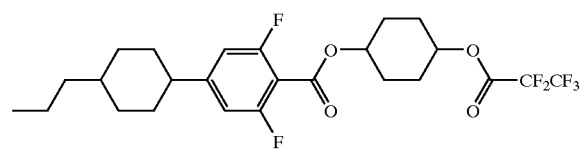
No.260
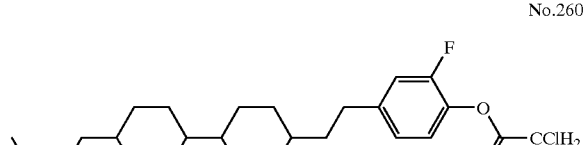
No.261
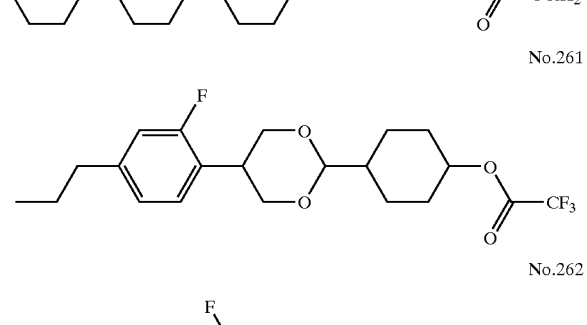
No.262
No.263
No.264
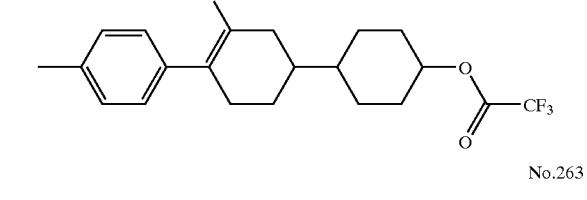
No.265
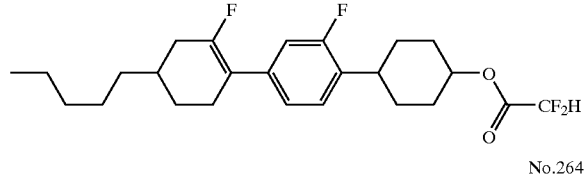
No.266
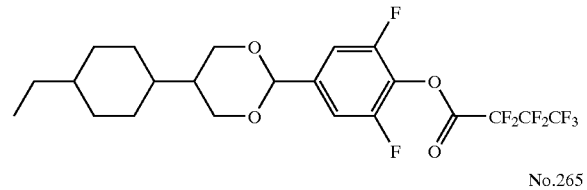
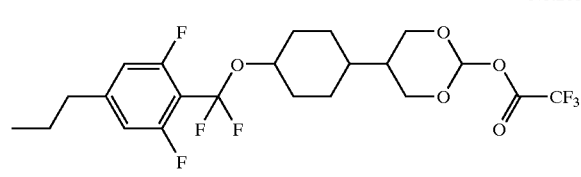
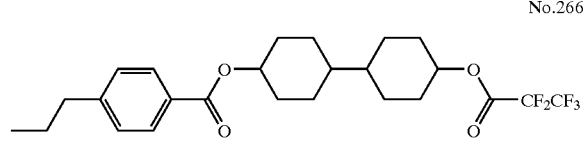

No.267
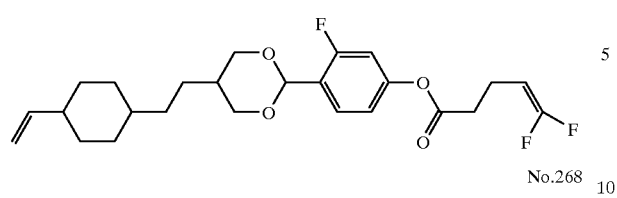
No.276
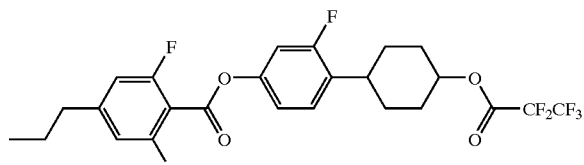
No.268 / No.277 / No.269 / No.278 / No.270 / No.279
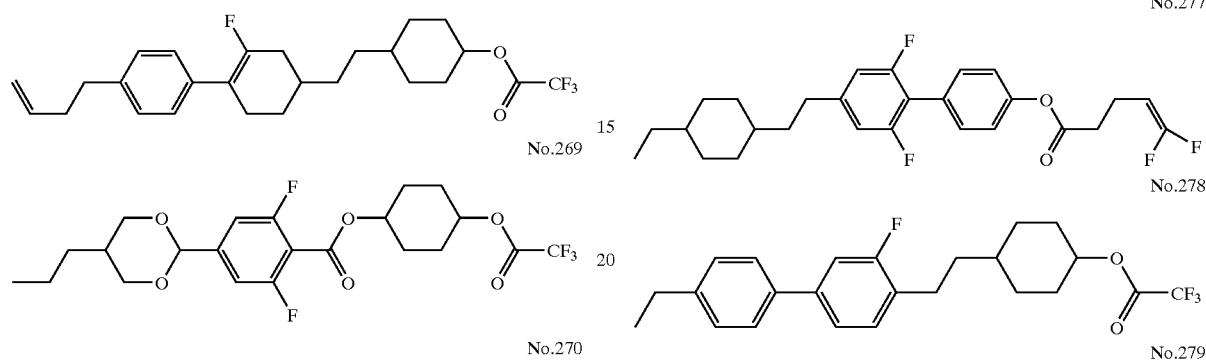
No.271 / No.280
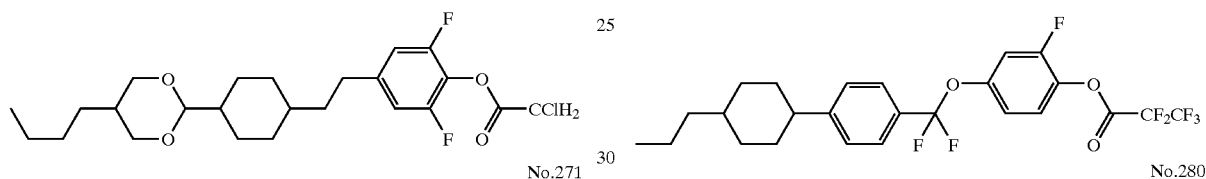
No.272 / No.281
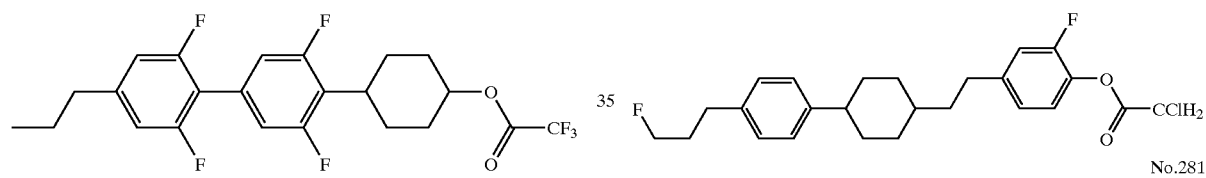
No.273 / No.282
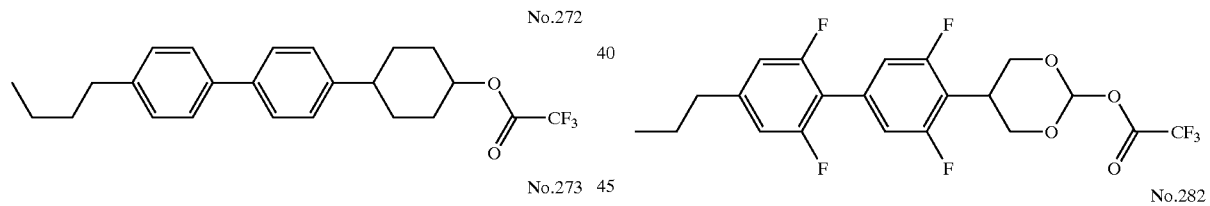
No.274 / No.283
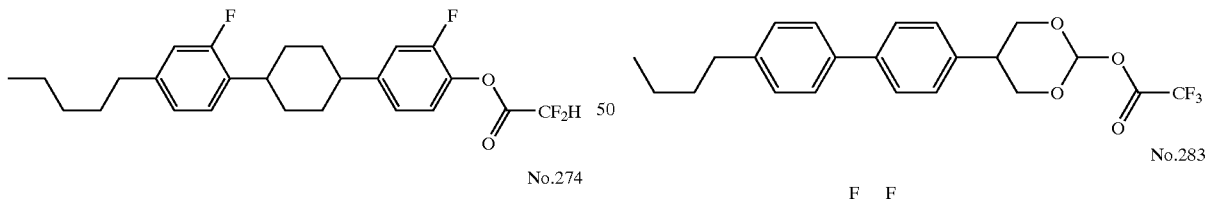
No.275 / No.284
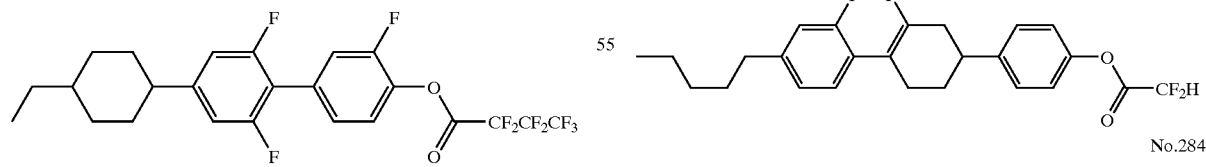
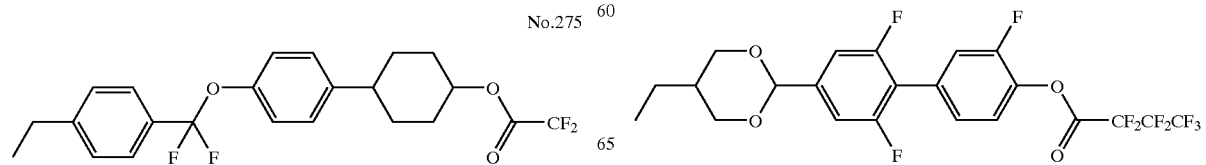

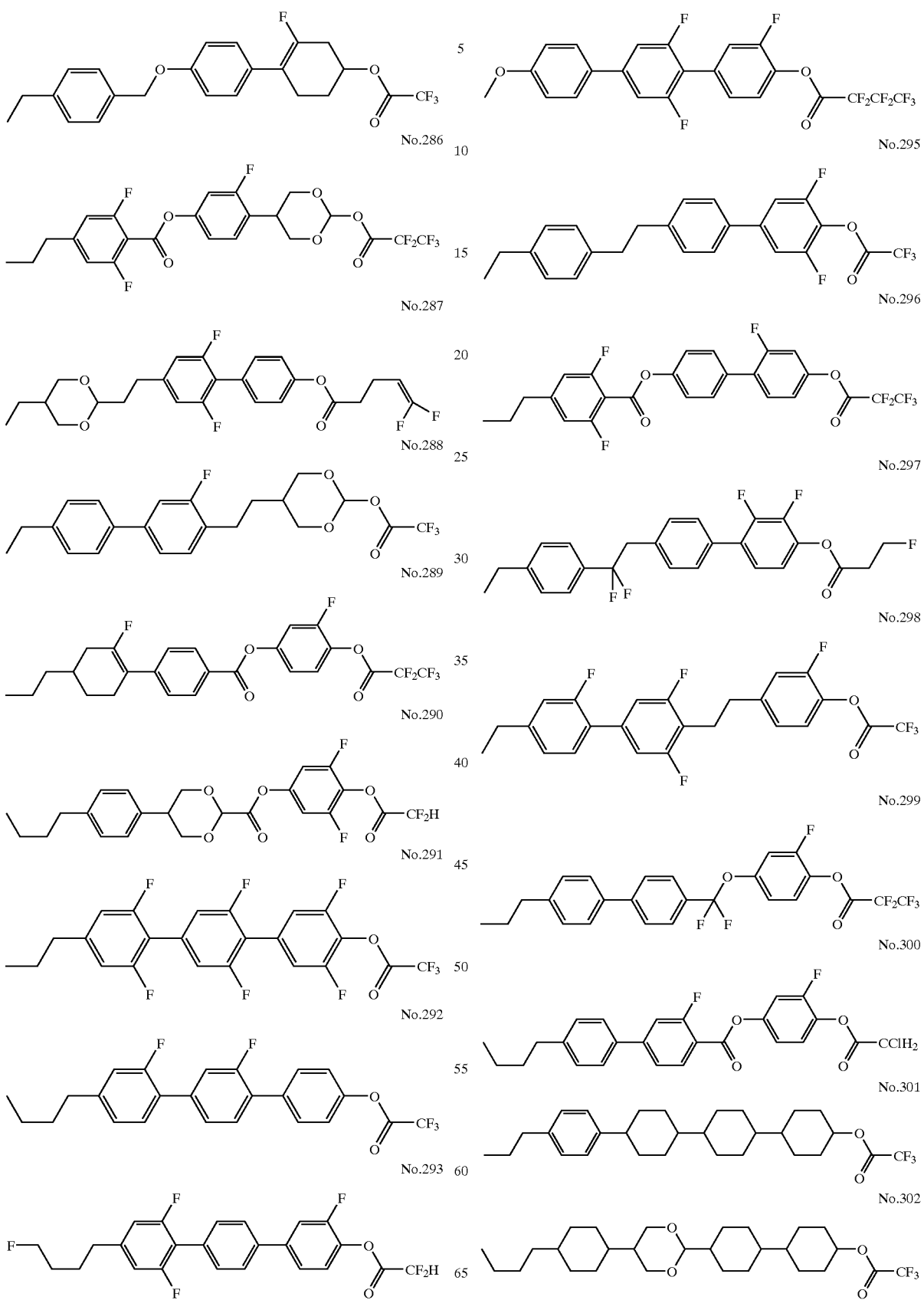

-continued
No.303
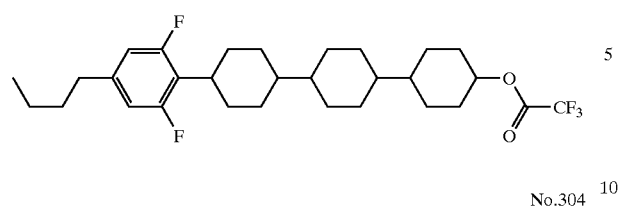
No.304
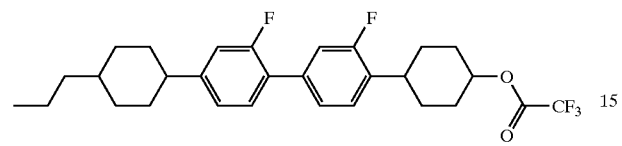
No.305
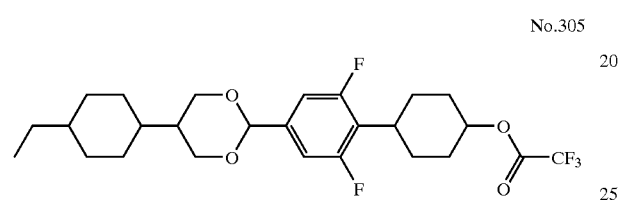
No.306
No.307
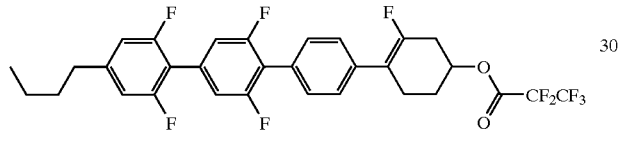
No.308
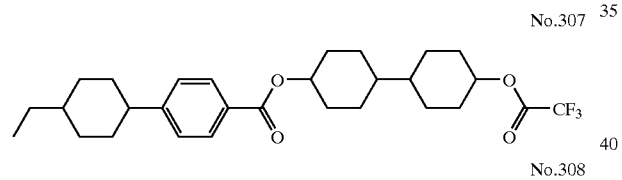
No.309
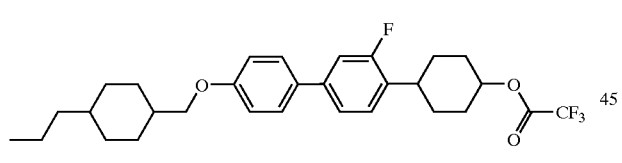
No.310
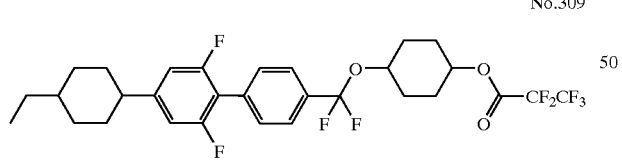
No.311
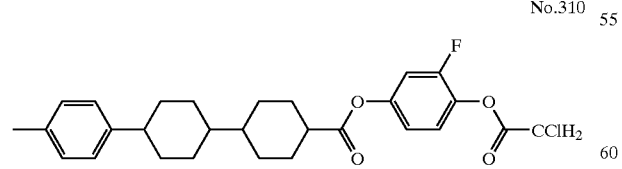
-continued
No.312
No.313
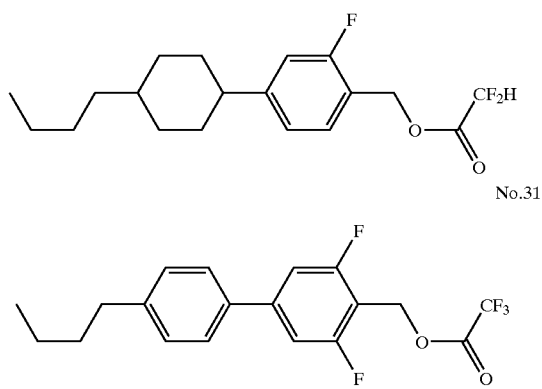
No.314
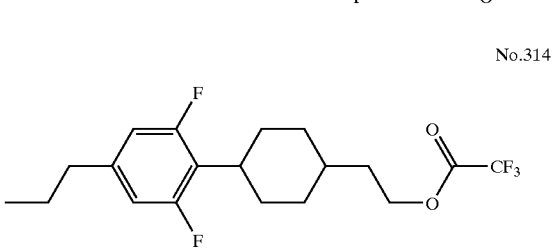
No.315
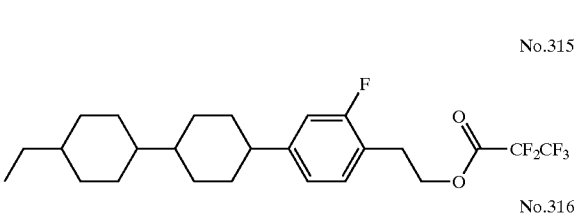
No.316
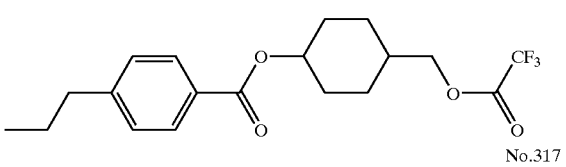
No.317
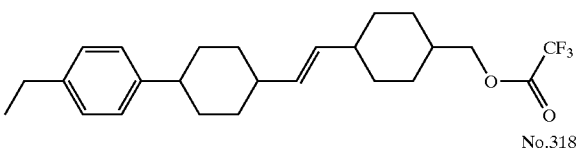
No.318
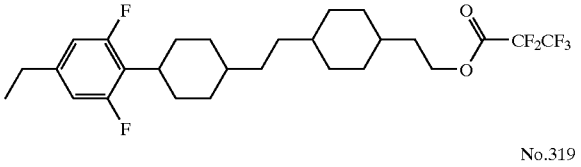
No.319
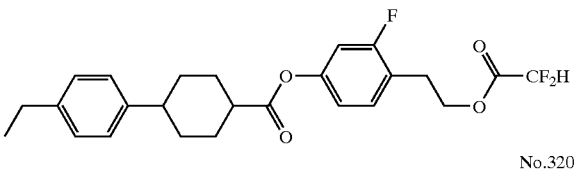
No.320
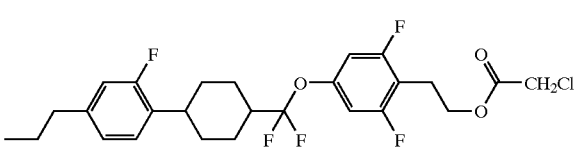

No.321 – No.339 (chemical structures)

No.340
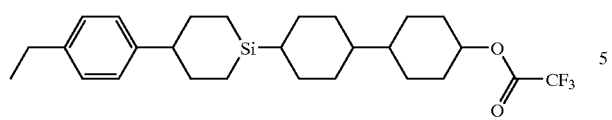

No.341
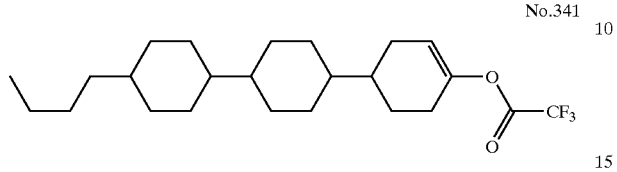

No.342
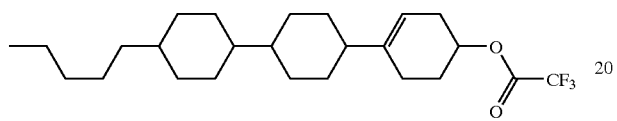

No.343
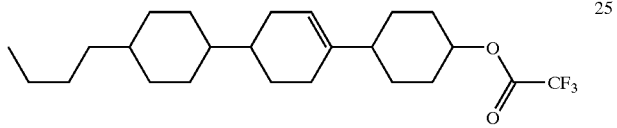

No.344
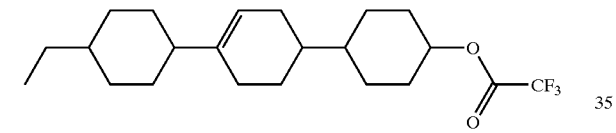

No.345
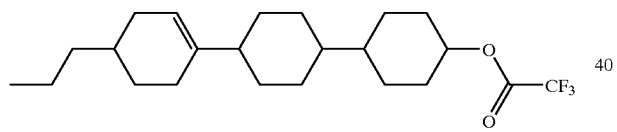

No.346
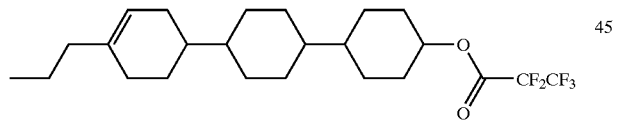

No.347
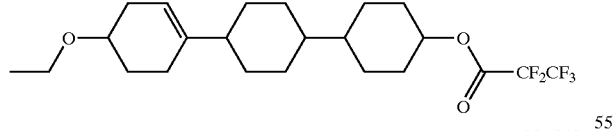

No.348
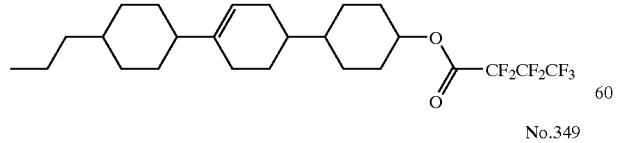

No.349
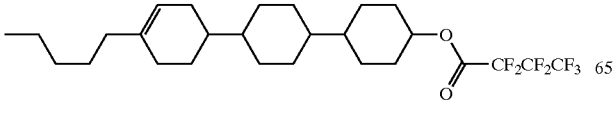

No.350
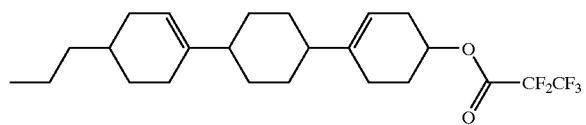

Example 16 (Use Example 1)

Nematic liquid crystal composition (hereinafter sometimes referred to as liquid crystal composition A1) comprising the following cyanophenylcyclohexane type liquid crystal compounds each in the amount shown below

| | |
|---|---|
| 4-(4-propylcyclohexyl)benzonitrile | 24% |
| 4-(4-pentylcyclohexyl)benzonitrile | 36% |
| 4-(4-heptylcyclohexyl)benzonitrile | 25% |
| 4-(4-(4-pentylcyclohexyl)phenylbenzonitrile | 15% | had the following characteristics:

Clearing point (TNI): 71.7° C., threshold voltage (Vth) at a cell thickness of 8.8 μm: 1.78 V, Δε: 11.0, Δn: 0.137, and viscosity (η) at 20° C.: 26.3 mPa·s.

Liquid crystal composition B1 comprising 85% by weight of the liquid crystal composition A1 and 15% by weight of trifluoroacetic acid 4-(4-propylcyclohexyl)cyclohexyl ester (Compound No. 3) was prepared. Characteristics of liquid crystal composition B1 were as follows:

Clearing point (TNI): 62.2° C., threshold voltage (Vth) at a cell thickness of 8.8 μm: 1.73 V, Δε: 10.4, Δn: 0.123, and viscosity (η) at 20° C.: 24.5 mPa·s.

Even after left at −20° C. for 30 days, this liquid crystal composition exhibited nematic phase.

Besides, physical propertyvalues of the compound of Compound No. 3 described above which values were calculated by extrapolation method from the physical property values of each of the liquid crystal compositions and the mixing ratio of the compound were as follows:

Clearing point (TNI): 8.4° C., Δε: 7.0, Δn: 0.044, and viscosity (η) at 20° C.: 10.3 mPa·s.

Example 17 (Use Example 2)

Liquid crystal composition B2 was prepared by the same manner as in Example 16 with the exception that trifluoroacetic acid 4-(4-propylcyclohexyl)cyclohexylmethyl ester (Compound No. 31) obtained in Example 2 was used in place of the compound of Compound No. 3. Characteristics of the liquid crystal composition B2 were as follows:

Clearing point (TNI): 57.3° C., threshold voltage (Vth) at a cell thickness of 8.8 μm: 1.57 V, Δε: 9.6, Δn: 0.118, and viscosity (η) at 20° C.: 26.2 mPa·s.

Even after left at −20° C. for 30 days, this liquid crystal composition exhibited nematic phase.

Besides, physical property values of the compound of Compound No. 31 described above which values were calculated by extrapolation method from the physical property values of each of the liquid crystal compositions and the mixing ratio of the compound were as follows:

Clearing point (TNI): −24.3° C., Δε: 1.7, Δn: 0.010, and viscosity (η) at 20° C.: 21.7 mPa·s.

Example 18 (Use Example 3)

Liquid crystal composition B3 was prepared by the same manner as in Example 16 with the exception that trifluoroacetic acid 4-(4-ethylcyclohexyl)cyclohexyl ester (Compound No. 2) obtained in Example 3 was used in place of the compound of Compound No. 3. Characteristics of the liquid crystal composition B3 were as follows:

Clearing point (TNI): 58.0° C., threshold voltage (Vth) at a cell thickness of 8.8 μm: 1.62 V, Δε: 10.3, Δn: 0.120, and viscosity (η) at 20° C.: 24.9 mPa·s.

Even after left at −20° C. for 30 days, this liquid crystal composition exhibited nematic phase.

Besides, physical property values of the compound of Compound No. 2 described above which values were calculated by extrapolation method from the physical property values of each of the liquid crystal compositions and the mixing ratio of the compound were as follows:

Clearing point (TNI): −19.6° C., Δε: 6.33, Δn: 0.024, and viscosity (η) at 20° C.: 13.0 mPa·s.

Example 19 (Use Example 4)

Liquid crystal composition B4 was prepared by the same manner as in Example 16 with the exception that trifluoroacetic acid 4-(4-(4-propylphenyl)cyclohexyl)cyclohexyl ester (Compound No. 251) obtained in Example 4 was used in place of the compound of Compound No. 3. Characteristics of the liquid crystal composition B4 were as follows:

Clearing point (TNI): 77.4° C., threshold voltage (Vth) at a cell thickness of 8.7 μm: 1.85 V, Δε: 10.7, Δn: 0.131, and viscosity (η) at 20° C.: 28.9 mPa·s.

Even after left at −20° C. for 30 days, this liquid crystal composition exhibited nematic phase.

Besides, physical property values of the compound of Compound No. 251 described above which values were calculated by extrapolation method from the physical property values of each of the liquid crystal compositions and the mixing ratio of the compound were as follows:

Clearing point (TNI): 109.7° C., Δε: 9.0, Δn: 0.097, and viscosity (η) at 20° C.: 39.7 mPa·s.

Example 20 (Use Example 5)

Liquid crystal composition B5 was prepared by the same manner as in Example 16 with the exception that trifluoroacetic acid 4-(4-butylcyclohexyl)cyclohexyl ester (Compound No. 1) obtained in Example 5 was used in place of the compound of Compound No. 3. Characteristics of the liquid crystal composition B5 were as follows:

Clearing point (TNI): 62.3° C., threshold voltage (Vth) at a cell thickness of 8.9 μm: 1.69 V, Δε: 10.4, Δn: 0.122, and viscosity (η) at 20° C.: 24.8 mPa·s.

Even after left at −20° C. for 30 days, this liquid crystal composition exhibited nematic phase.

Besides, physical property values of the compound of Compound No. 1 described above which values were calculated by extrapolation method from the physical property values of each of the liquid crystal compositions and the mixing ratio of the compound were as follows:

Clearing point (TNI): 9.0° C., Δε: 7.0, Δn: 0.037, and viscosity (η) at 20° C.: 16.3 mPa·s.

Example 21 (Use Example 6)

Liquid crystal composition B6 was prepared by the same manner as in Example 16 with the exception that trifluoroacetic acid 2-(4-(4-propylcyclohexyl)cyclohexyl) cyclohexylethyl ester (Compound No. 34) obtained in Example 6 was used in place of the compound of Compound No. 3. Characteristics of the liquid crystal composition B6 were as follows:

Clearing point (TNI): 60.2° C., threshold voltage (Vth) at a cell thickness of 8.7 μm: 1.63 V, Δε: 9.6, Δn: 0.120, and viscosity (η) at 20° C.: 25.0 mPa·s.

Even after left at −20° C. for 30 days, this liquid crystal composition exhibited nematic phase.

Besides, physical property values of the compound of Compound No. 34 described above which values were calculated by extrapolation method from the physical property values of each of the liquid crystal compositions and the mixing ratio of the compound were as follows:

Clearing point (TNI): −5.0° C., Δε: 1.7, Δn: 0.024, and viscosity (η) at 20° C.: 17.6 mPa·s.

Example 22 (Use Example 7)

Liquid crystal composition B7 was prepared by the same manner as in Example 16 with the exception that difluoroacetic acid 4-(4-ethylcyclohexyl)cyclohexyl ester (Compound No. 5) obtained in Example 7 was used in place of the compound of Compound No. 3. Characteristics of the liquid crystal composition B7 were as follows:

Clearing point (TNI): 59.1° C., threshold voltage (Vth) at a cell thickness of 8.9 μm: 1.62 V, Δε: 10.0, Δn: 0.118, and viscosity (η) at 20° C.: 25.7 mPa·s.

Even after left at −20° C. for 30 days, this liquid crystal composition exhibited nematic phase.

Besides, physical property values of the compound of Compound No. 5 described above which values were calculated by extrapolation method from the physical property values of each of the liquid crystal compositions and the mixing ratio of the compound were as follows:

Clearing point (TNI): −12.3° C., Δε: 4.3, Δn: 0.010, and viscosity (η) at 20° C.: 22.3 mPa·s.

Example 23 (Use Example 8)

Liquid crystal composition B8 was prepared by the same manner as in Example 16 with the exception that difluoroacetic acid 4-(4-propylcyclohexyl)cyclohexyl ester (Compound No. 4) obtained in Example 8 was used in place of the compound of Compound No. 3. Characteristics of the liquid crystal composition B8 were as follows:

Clearing point (TNI): 64.0° C., threshold voltage (Vth) at a cell thickness of 8.8 μm: 1.75 V, Δε: 10.3, Δn: 0.122, and viscosity (η) at 20° C.: 24.7 mPa·s.

Even after left at −20° C. for 30 days, this liquid crystal composition exhibited nematic phase.

Besides, physical property values of the compound of Compound No. 4 described above which values were calculated by extrapolation method from the physical property values of each of the liquid crystal compositions and the mixing ratio of the compound were as follows:

Clearing point (TNI): 20.4° C., Δε: 6.3, Δn: 0.037, and viscosity (η) at 20° C.: 15.6 mPa·s.

Example 24 (Use Example 9)

Liquid crystal composition B9 was prepared by the same manner as in Example 16 with the exception that trifluoroacetic acid 4-(4-propylcyclohexyl)-1-cyclohexenyl ester (Compound No. 121) obtained in Example 9 was used in place of the compound of Compound No. 3. Characteristics of the liquid crystal composition B9 were as follows:

Clearing point (TNI): 59.8° C., threshold voltage (Vth) at a cell thickness of 8.9 μm: 1.66 V, Δε: 10.7, Δn: 0.122, and viscosity (η) at 20° C.: 23.4 mPa·s.

Even after left at −20° C. for 30 days, this liquid crystal composition exhibited nematic phase.

Besides, physical property values of the compound of Compound No. 121 described above which values were calculated by extrapolation method from the physical property values of each of the liquid crystal compositions and the mixing ratio of the compound were as follows:

Clearing point (TNI): −7.6° C., Δε: 9.0, Δn: 0.037, and viscosity (η) at 20° C.: 7.0 mPa·s.

Example 25 (Use Example 10)

Liquid crystal composition B10 was prepared by the same manner as in Example 16 with the exception that trifluoroacetic acid 4-(4-(4-propylcyclohexyl)cyclohexyl)-1-cyclohexenyl ester (Compound No. 341) obtained in Example 10 was used in place of the compound of Compound No. 3. Characteristics of the liquid crystal composition B10 were as follows:

Clearing point (TNI): 81.5° C., threshold voltage (Vth) at a cell thickness of 8.8 μm: 1.75 V, Δε: 10.7, Δn: 0.129, and viscosity (η) at 20° C.: 28.4 mPa·s.

Besides, physical property values of the compound of Compound No. 341 described above which values were calculated by extrapolation method from the physical property values of each of the liquid crystal compositions and the mixing ratio of the compound were as follows:

Clearing point (TNI): 137.0° C., Δε: 9.0, Δn: 0.084, and viscosity (η) at 20° C.: 40.3 mPa·s.

Example 26 (Use Example 11)

Liquid crystal composition B11 comprising 90% by weight of liquid crystal composition A1 described above and 10% by weight of trifluoroacetic acid 4-(4-(4-butylcyclohexyl)cyclohexyl)-cyclohexyl ester (Compound No. 232) obtained in Example 11 was prepared. Characteristics of the liquid crystal composition B11 were as follows:

Clearing point (TNI): 79.1° C., threshold voltage (Vth) at a cell thickness of 8.8 μm: 1.86 V, Δε: 11.0, Δn: 0.132, and viscosity (η) at 20° C.: 27.5 mPa·s.

Besides, physical property values of the compound of Compound No. 232 described above which values were calculated by extrapolation method from the physical property values of each of the liquid crystal compositions and the mixing ratio of the compound were as follows:

Clearing point (TNI): 145.7° C., Δε: 11.0, Δn: 0.087, and viscosity (η) at 20° C.: 34.3 mPa·s.

Example 27 (Use Example 12)

Liquid crystal composition B12 was prepared by the same manner as in Example 16 with the exception that trifluoroacetic acid 4-(4-(5-butyl-1,3-dioxane-2-yl)cyclohexyl) cyclohexyl ester (Compound No. 241) obtained in Example 12 was used in place of the compound of Compound No. 3. Characteristics of the liquid crystal composition B12 were as follows:

Clearing point (TNI): 78.3° C., threshold voltage (Vth) at a cell thickness of 8.9 μm: 1.60 V, Δε: 12.1, Δn: 0.127, and viscosity (η) at 20° C.: 40.8 mPa·s.

Besides, physical property values of the compound of Compound No. 241 described above which values were calculated by extrapolation method from the physical property values of each of the liquid crystal compositions and the mixing ratio of the compound were as follows:

Clearing point (TNI): 115.7° C., Δε: 18.3, Δn: 0.070, and viscosity (η) at 20° C.: 123.0 mPa·s.

Example 28 (Use Example 13)

Liquid crystal composition B13 was prepared by the same manner as in Example 16 with the exception that trifluoroacetic acid 4-(4-(4-butylcyclohexyl)-1-cyclohexenyl) cyclohexyl ester (Compound No. 343) obtained in Example 13 was used in place of the compound of Compound No. 3. Characteristics of the liquid crystal composition B13 were as follows:

Clearing point (TNI): 79.1° C., threshold voltage (Vth) at a cell thickness of 8.8 μm: 1.87 V, Δε: 10.8, Δn: 0.127, and viscosity (η) at 20° C.: 29.9 mPa·s.

Besides, physical property values of the compound of Compound No. 343 described above which values were calculated by extrapolation method from the physical property values of each of the liquid crystal compositions and the mixing ratio of the compound were as follows:

Clearing point (TNI): 121.0° C., Δε: 9.7, Δn: 0.070, and viscosity (η) at 20° C.: 50.3 mPa·s.

Example 29 (Use Example 14)

Liquid crystal composition B14 was prepared by the same manner as in Example 16 with the exception that trifluoroacetic acid 4-(4-(2-(4-pentylcyclohexyl)ethyl)-3-cyclohexenyl)-cyclohexyl ester (Compound No. 245) obtained in Example 14 was used in place of the compound of Compound No. 3. Characteristics of the liquid crystal composition B14 were as follows:

Clearing point (TNI): 76.0° C., threshold voltage (Vth) at a cell thickness of 8.9 μm: 1.92 V, Δε: 10.9, Δn: 0.127, and viscosity (η) at 20° C.: 28.9 mPa·s.

Besides, physical property values of the compound of Compound No. 245 described above which values were calculated by extrapolation method from the physical property values of each of the liquid crystal compositions and the mixing ratio of the compound were as follows:

Clearing point (TNI): 100.4° C., Δε: 10.3, Δn: 0.070, and viscosity (η) at 20° C.: 43.6 mPa·s.

Example 30 (Use Example 15)

Liquid crystal composition B15 was prepared by the same manner as in Example 16 with the exception that pentafluoropropionic acid 4-(4-(4-propylcyclohexyl)cyclohexyl)-cyclohexyl ester (Compound No. 6) obtained in Example 15 was used in place of the compound of Compound No. 3. Characteristics of the liquid crystal composition B15 were as follows:

Clearing point (TNI): 62.4° C., threshold voltage (Vth) at a cell thickness of 8.8 μm: 1.66 V, Δε: 10.7, Δn: 0.121, and viscosity (η) at 20° C.: 24.4 mPa·s.

Besides, physical property values of the compound of Compound No. 6 described above which values were calculated by extrapolation method from the physical property values of each of the liquid crystal compositions and the mixing ratio of the compound were as follows:

Clearing point (TNI): 9.7° C., Δε: 9.0, Δn: 0.030, and viscosity (η) at 20° C.: 13.6 mPa·s.

Example 31 (Comparative Example 1)

Liquid crystal composition C1 was prepared by the same manner as in Example 16 with the exception that 4-(4-n-pentyl-cyclohexyl)-1-cyanocyclohexane (Compound (10) described above) was used in place of the compound of Compound No. 3. Characteristics of the liquid crystal composition C1 were as follows:

Clearing point (TNI): 73.5° C., Δε: 9.9, Δn: 0.127, and viscosity (η) at 20° C.: 31.2 mPa·s.

Besides, physical property values of the compound of Compound No. 10 described above which values were calculated by extrapolation method from the physical property values of each of the liquid crystal compositions and the mixing ratio of the compound were as follows:

Clearing point (TNI): 79.7° C., Δε: 3.7, Δn: 0.068, and viscosity (η) at 20° C.: 55.0 mPa·s.

When this result is compared with those in Examples 16, 18, 20, 22, 23, 24, and 30, it can be understood that compounds of the present invention having no benzene ring at the core part have larger Δε value and lower viscosity than conventional compounds.

Example 32 (Comparative Example 2)

Liquid crystal composition C2 was prepared by the same manner as in Example 5 with the exception that 4-(4-n-propyl-cyclohexyl)cyclohexylcarboxylic acid 3,4,5-trifluorophenyl ester (Compound (14) described above) was used in place of the compound of Compound No. 3. Characteristics of the liquid crystal composition C2 were as follows:

Clearing point (TNI): 75.3° C., Δε: 11.0, Δn: 0.128, and viscosity (η) at 20° C.: 29.9 mPa·s.

Besides, physical property values of the compound of Compound No. 14 described above which values were calculated by extrapolation method from the physical property values of each of the liquid crystal compositions and the mixing ratio of the compound were as follows:

Clearing point (TNI): 95.7° C., Δε: 11.0, Δn: 0.077, and viscosity (η) at 20° C.: 46.3 mPa·s.

When this result is compared with that in Example 19, it can be understood that compounds of the present invention having benzene ring at the core part have high clearing point and low viscosity.

As described above, liquid crystalline compounds of the present invention having low Δn value have large Δε value and low viscosity, or the compounds having medium extent or large Δn value have high clearing point and low viscosity.

INDUSTRIAL APPLICABILITY

When used as component of liquid crystal compositions, liquid crystalline compounds of the present invention can achieve driving at a low voltage, driving at a wide temperature range, and high speed response of liquid crystal display devices, particularly liquid crystal display devices for TN, a STN, or TFT mode.

What is claimed is:

1. An ester compound expressed by the general formula (1)

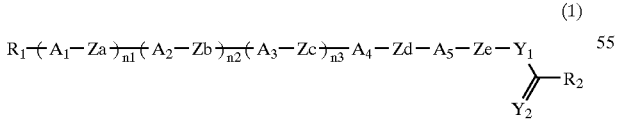

(1)

wherein $R_1$ represents hydrogen atom, cyano group, nitro group, amino group, a halogen atom, a straight chain or branched alkyl group having 1 to 20 carbon atoms, or a straight chain or branched alkenyl group having 2 to 20 carbon atoms; one or more hydrogen atoms in these alkyl group and alkenyl group may be replaced by halogen atoms; one or more —$CH_2$— in these alkyl group and alkenyl group may be replaced by oxygen atoms or sulfur atoms, but there is no case where oxygen atoms are adjacent; and one or more carbon atoms in these alkyl group and alkenyl group may be replaced by silicon atoms;

$A_1$ to $A_5$ each independently represent 1,4-cyclohexylene, 1,4-phenylene, 1-cyclohexene-1,4-diyl, 3-cyclohexene-1,4-diyl, 1-sila-1,4-cyclohexylene, or 4-sila-1,4-cyclohexylene; one or more —$CH_2$— in the 1,4-cyclohexylene, 1-cyclohexene-1,4-diyl, and 3-cyclohexene-1,4-diyl may each independently be replaced by oxygen atoms, sulfur atoms, —CO—, —CS—, $SiH_2$—, —NH—, —$CF_2$—, or —CFH—, but there is no case where oxygen atoms are adjacent; hydrogen atoms which bond to carbon atoms at position 2 and position 3, respectively, in the 1-cyclohexene-1,4-diyl or 3-cyclohexene-1,4-diyl may each independently be replaced by fluorine atoms; one or more hydrogen atoms in the 1,4-phenylene may each independently be replaced by halogen atoms, halogenated alkyl groups having 1 to 3 carbon atoms, methyl groups, cyano groups, or nitro groups; and one or more —CH= in the 1,4-phenylene may each independently be replaced by nitrogen atoms;

bonding groups Za to Zd each independently represent single bond, —$CH_2$—, —O—, —C≡C—, —COO—, —OCO—, or an alkylene group or alkenylene group having 2 to 4 carbon atoms; one or more hydrogen atoms in these groups may be replaced by halogen atoms; and —$CH_2$— in these groups may each independently be replaced by oxygen atom, sulfur atom, —CS—, —NH—, —$CF_2$—, or —CFH—, but there is no case where oxygen atoms are adjacent;

bonding group Ze represents single bond, an alkylene group or alkenylene group having 1 to 10 carbon atoms; and —$CH_2$— in these groups may each independently be replaced by, oxygen atom, sulfur atom, —$CF_2$—, —CFH—, —CH=CH—, —CF=CF—, —CF=CH—, or —C≡C—, but there is no case where oxygen atoms are adjacent;

n1 to n3 are each independently 0 or 1, but $n1 \leq n2 \leq n3$;

$Y_1$ and $Y_2$ each independently represent oxygen atom or sulfur atom;

$R_2$ represents a halogen atom, a straight chain alkyl group having 1 to 20 carbon atoms, or straight chain alkenyl group having 2 to 20 carbon atoms, one or more hydrogen atoms in these alkyl group and alkenyl group are replaced by halogen atoms; one or more —$CH_2$— in these groups may be replaced by oxygen atoms or sulfur atoms, but there is no case where oxygen atoms are adjacent; and one or more carbon atoms in these groups may be replaced by silicon atoms;

provided that when $A_5$ represents unsubstituted 1,4-phenylene in this compound, then Zd is single bond, Ze is single bond or an alkylene group having 1 to 10 carbon atoms in which alkylene group —$CH_2$— may independently be replaced by oxygen atom, sulfur atom, —$CF_2$—, —CFH—, —CH=CH—, —CF=CF—, —CF=CH—, or —C≡C—, but there is no case where oxygen atoms are adjacent, and $A_4$ is not 1,4-phenylene; and each atom which constitutes this compound may be replaced by its isotope.

2. The ester compound according to claim 1 wherein ring $A_5$ is 1,4-cyclohexylene, 1-cyclohexene-1,4-diyl, or 3-cyclohexene-1,4-diyl; one or more —$CH_2$— in these groups may each independently be replaced by oxygen atoms, sulfur atoms, —CO—, —CS—, —$SiH_2$—, —NH—, —CF$_2$—, or —CFH—, but there is no case where oxygen atoms are adjacent; hydrogen atoms which bond to carbon atoms at position 2 and position 3, respectively, in the 1-cyclohexene-1,4-diyl or 3-cyclohexene-1,4-diyl may be replaced by fluorine atoms; and both Y$_1$ and Y$_2$ are oxygen atoms in the general formula (1).

3. The ester compound according to claim 2 wherein Ze is single bond in the general formula (1).

4. The ester compound according to claim 3 wherein R$_2$ is a straight chain alkyl group having 1 to 5 carbon atoms in which group two or more hydrogen atoms are replaced by fluorine atoms in the general formula (1).

5. The ester compound according to claim 4 wherein both n1 and n2 are 0, n3 is 1, both rings A$_4$ and A$_5$ are 1,4-cyclohexylene in which one or more —CH$_2$— may each independently be replaced by oxygen atoms, but there is no case where oxygen atoms are adjacent; and Zd is single bond in the general formula (1).

6. The ester compound according to claim 1 wherein both n1 and n2 are 0, n3 is 1, and at least one of rings A$_3$, A$_4$, and A$_5$ is 1-cyclohexene-1,4-diyl or 3-cyclohexene-1,4-diyl in the general formula (1).

7. The ester compound according to claim 1 wherein ring A$_5$ is 1,4-phenylene in which one or more hydrogen atoms may each independently be replaced by halogen atoms, halogenated alkyl groups having 1 to 3 carbon atoms, methyl groups, cyano groups, or nitro groups, and one or more —CH= may each independently be replaced by nitrogen atoms in the general formula (1).

8. The ester compound according to claim 7 wherein ring A$_5$ is 1,4-phenylene in which one or more hydrogen atoms are replaced by fluorine atoms in the general formula (1).

9. The ester compound according to claim 1 wherein R$_1$ is a straight chain alkyl group having 1 to 20 carbon atoms or a straight chain alkenyl group having 2 to 20 carbon atoms; one or more hydrogen atoms in which groups may be replaced by halogen atoms; one or more —CH$_2$— in the group may be replaced by oxygen atoms or sulfur atoms, but there is no case where oxygen atoms are adjacent; and one or more carbon atoms in the groups may be replaced by silicon atoms in the general formula (1).

10. A liquid crystal composition comprising at least two components, at least one of which is an ester compound defined in any one of claims 1 to 9 and, as an optional component, at least one optically active compound.

11. A liquid crystal composition comprising, as a first component, at least one ester compound defined in any one of claims 1 to 9, as a second component, at least one compound selected from the group consisting of the compounds expressed by any one of the general formulas (2), (3), and (4)

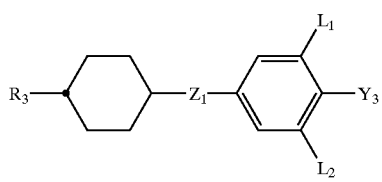
(2)

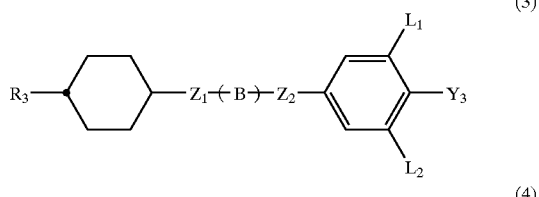
(3)

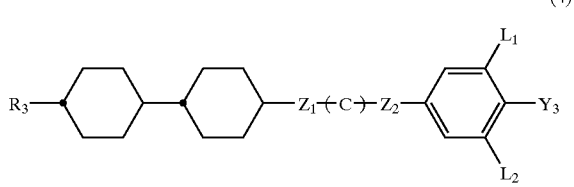
(4)

wherein R$_3$, Y$_3$, L$_1$, L$_2$, Z$_1$, and Z$_2$ may be the same or different among each of the formulas;

R$_3$ represents an alkyl group having 1 to 10 carbon atoms in which alkyl group one or not-adjacent two or more methylene groups may be replaced by oxygen atoms or —CH=CH—; and any hydrogen atom in the alkyl group may be replaced by fluorine atom;

Y$_3$ represents fluorine atom, chlorine atom, —OCF$_3$, —OCF$_2$H, —CF$_3$, —CF$_2$H, —CFH$_2$, —OCF$_2$CF$_2$H, or —OCF$_2$CFHCF$_3$;

L$_1$ and L$_2$ each independently represent hydrogen atom or fluorine atom;

Z$_1$ and Z$_2$ each independently represent —CH$_2$CH$_2$—, —CH$_2$CH$_2$CH$_2$CH$_2$—, —COO—, —CF$_2$O—, —OCF$_2$—, —CH=CH—, or single bond;

ring B represents trans-1,4-cyclohexylene or 1,3-dioxane-2,5-diyl, or 1,4-phenylene in which hydrogen atom may be replaced by fluorine atom;

ring C represents trans-1,4-cyclohexylene, or 1,4-phenylene in which hydrogen atom may be replaced by fluorine atom; and each atom which constitutes these compounds may be replaced by its isotope, and as an optional component, at least one optically active compound.

12. A liquid crystal composition comprising, as a first component, at least one compound defined in any one of claims 1 to 9, as a second component, at least one compound selected from the group consisting of the compounds expressed by the general formula (5) or (6)

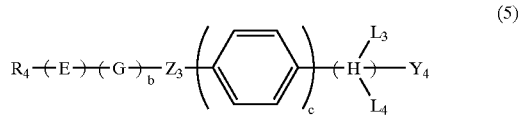
(5)

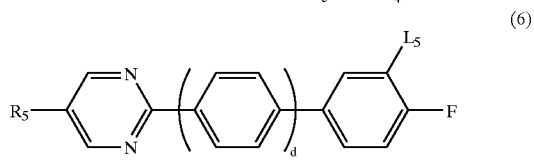
(6)

wherein R$_4$ and R$_5$ each independently represent an alkyl group having 1 to 10 carbon atoms in which alkyl group one or not-adjacent two or more methylene groups may be replaced by oxygen atoms or —CH=CH—; and hydrogen atom in the group may be replaced by fluorine atom;

Y$_4$ represents —CN or —C≡C—CN;

ring E represents trans-1,4-cyclohexylene, 1,4-phenylene, 1,3-dioxane-2,5-diyl, or pyrimidine-2,5-diyl;

ring G represents trans-1,4-cyclohexylene or pyrimidine-2,5-diyl, or 1,4-phenylene in which hydrogen atom may be replaced by fluorine atom;

ring H represents trans-1,4-cyclohexylene or 1,4-phenylene;

$Z_3$ represents —$CH_2CH_2$—, —COO—, or single bond;

$L_3$, $L_4$, and $L_5$ each independently represent hydrogen atom or fluorine atom;

b, c, and d are each independently 0 or 1; and each atom which constitutes these compounds may be replaced by its isotope, and as an optional component, at least one optically active compound.

13. A liquid crystal composition comprising, as a first component, at least one compound defined in any one of claims 1 to 9, as a second component, at least one compound selected from the group consisting of the compounds expressed by any one of the general formulas (2), (3), and (4), as a third component, at least one compound selected from the group consisting of the compounds expressed any one of the general formulas (7), (8), and (9)

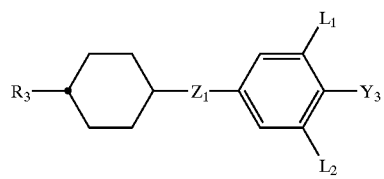
(2)

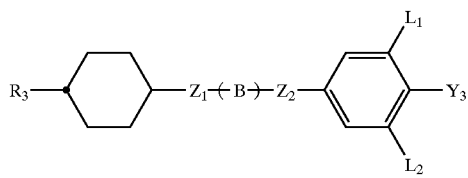
(3)

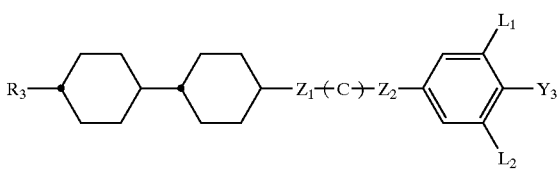
(4)

wherein $R_3$, $Y_3$, $L_1$, $L_2$, $Z_1$, and $Z_2$ may be the same or different among each of the formulas;

$R_3$ represents an alkyl group having 1 to 10 carbon atoms in which alkyl group one or not-adjacent two or more methylene groups may be replaced by oxygen atoms or —CH=CH—; and any hydrogen atom in the alkyl group may be replaced by fluorine atom;

$Y_3$ represents fluorine atom, chlorine atom, —$OCF_3$, —$OCF_2H$, —$CF_3$, —$CF_2H$, —$CFH_2$, —$OCF_2CF_2H$, or —$OCF_2CFHCF_3$;

$L_1$ and $L_2$ each independently represent hydrogen atom or fluorine atom;

$Z_1$ and $Z_2$ each independently represent —$CH_2CH_2$—, —$CH_2CH_2CH_2CH_2$—, —COO—, —$CF_2O$—, —$OCF_2$—, —CH=CH—, or single bond;

ring B represents trans-1,4-cyclohexylene or 1,3-dioxane-2,5-diyl, or 1,4-phenylene in which hydrogen atom may be replaced by fluorine atom;

ring C represents trans-1,4-cyclohexylene, or 1,4-phenylene in which hydrogen atom may be replaced by fluorine atom; and each atom which constitutes these compounds may be replaced by its isotope,

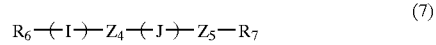
(7)

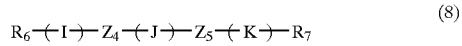
(8)

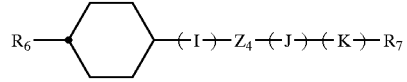
(9)

wherein $R_6$, $R_7$, I, J, and K may be the same or different among each of the formulas;

$R_6$ and $R_7$ each independently represent an alkyl group having 1 to 10 carbon atoms in which alkyl group one or not-adjacent two or more methylene groups may be replaced by oxygen atoms or —CH=CH—; and any hydrogen atom in the group may be replaced by fluorine atom;

ring I, ring J, and ring K each independently represent trans-1,4-cyclohexylene or pyrimidine-2,5-diyl, or 1,4-phenylene in which hydrogen atom may be replaced by fluorine atom;

$Z_4$ and $Z_5$ each independently represent —C≡C—, —COO—, —$CH_2CH_2$—, —CH=CH—, or single bond; and each atom which constitutes these compounds may be replaced by its isotope, and, as an optional component, at least one optically active compound.

14. A liquid crystal composition comprising, as a first component, at least one compound defined in any one of claims 1 to 9, as a second component, at least one compound selected from the group consisting of the compounds expressed by the general formula (5) or (6), as a third component, at least one compound selected from the group consisting of the compounds expressed by any one of the general formulas (7), (8), and (9)

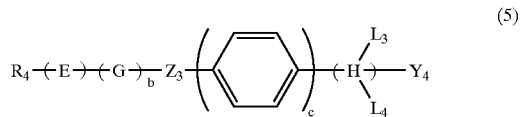
(5)

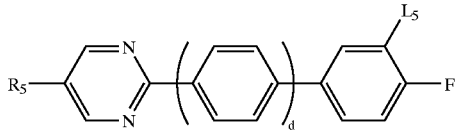
(6)

wherein $R_4$ and $R_5$ each independently represent an alkyl group having 1 to 10 carbon atoms in which alkyl group one or not-adjacent two or more methylene groups may be replaced by oxygen atoms or —CH=CH—; and hydrogen atom in the group may be replaced by fluorine atom;

$Y_4$ represents —CN or —C≡C—CN;

ring E represents trans-1,4-cyclohexylene, 1,4-phenylene, 1,3-dioxane-2,5-diyl, or pyrimidine-2,5-diyl;

ring G represents trans-1,4-cyclohexylene or pyrimidine-2,5-diyl, or 1,4-phenylene in which hydrogen atom may be replaced by fluorine atom;

ring H represents trans-1,4-oyclohexylene or 1,4-phenylene;

$Z_3$ represents —$CH_2CH_2$—, —COO—, or single bond;

$L_3$, $L_4$, and $L_5$ each independently represent hydrogen atom or fluorine atom;

b, c, and d are each independently 0 or 1; and each atom which constitutes these compounds may be replaced by its isotope, (7)

$R_6$—(I)—$Z_4$—(J)—$Z_5$—$R_7$ (8)

$R_6$—(I)—$Z_4$—(J)—$Z_5$—(K)—$R_7$ (9)

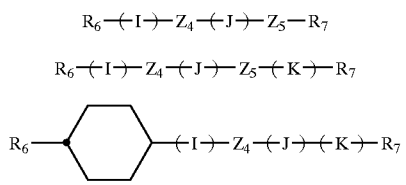

wherein $R_6$, $R_7$, I, J, and K may be the same or different among each of the formulas;

$R_6$ and $R_7$ each independently represent an alkyl group having 1 to 10 carbon atoms in which alkyl group one or not-adjacent two or more methylene groups may be replaced by oxygen atoms or —CH=CH—; and any hydrogen atom in the group may be replaced by fluorine atom;

ring I, ring J, and ring K each independently represent trans-1,4-cyclohexyleie or pyrimidine-2,5-diyl, or 1,4-phenylene in which hydrogen atom may be replaced by fluorine atom;

$Z_4$ and $Z_5$ each independently represent —C≡C—, —COO—, —$CH_2CH_2$—, —CH=CH—, or single bond; and each atom which constitutes these compounds may be replaced by its isotope, and, as an optional component, at least one optically active compound.

15. A liquid crystal composition comprising, as a first component, at least one compound defined in any one of claims 1 to 9, as a part of a second component, at least one compound selected from the group consisting of the compounds expressed by any one of the general formulas (2), (3), and (4), as another part of the second component, at least one compound selected from the group consisting of the compounds expressed by the general formula (5) or (6), as a third component, at least one compound selected from the group consisting of the compounds expressed by any one of the general formulas (7), (8), and (9)

(2)

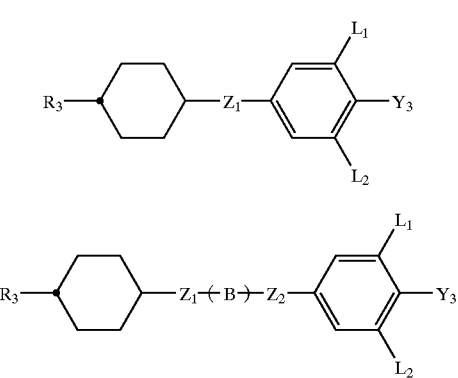

(3)

(4)

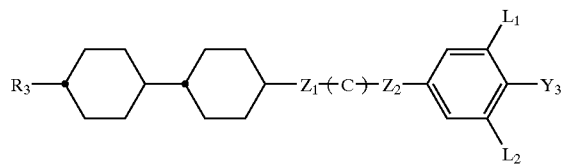

wherein $R_3$, $Y_3$, $L_1$, $L_2$, $Z_1$, and $Z_2$ may be the same or different among each of the formulas;

$R_3$ represents an alkyl group having 1 to 10 carbon atoms in which alkyl group one or not-adjacent two or more methylene groups may be replaced by oxygen atoms or —CH=CH—; and any hydrogen atom in the alkyl group may be replaced by fluorine atom;

$Y_3$ represents fluorine atom, chlorine atom, —$OCF_3$, —$OCF_2H$, —$CF_3$, —$CF_2H$, —$CFH_2$, —$OCF_2CF_2H$, or —$OCF_2CFHCF_3$;

$L_1$ and $L_2$ each independently represent hydrogen atom or fluorine atom;

$Z_1$ and $Z_2$ each independently represent —$CH_2CH_2$—, —$CH_2CH_2CH_2CH_2$—, —COO—, —$CF_2O$—, —$OCF_2$—, —CH=CH—, or single bond;

ring B represents trans-1,4-cyclohexylene or 1,3-dioxane-2,5-diyl, or 1,4-phenylene in which hydrogen atom may be replaced by fluorine atom;

ring C represents trans-1,4-cyclohexylene, or 1,4-phenylene in which hydrogen atom may, be replaced by fluorine atom; and each atom which constitutes these compounds may be replaced by its isotope, (5)

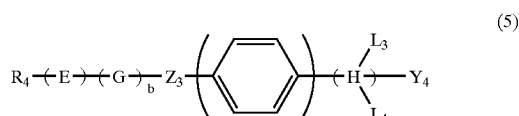

(6)

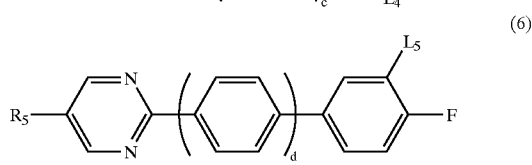

wherein $R_4$ and $R_5$ each independently represent an alkyl group having 1 to 10 carbon atoms in which alkyl group one or not-adjacent two or more methylene groups may be replaced by oxygen atoms or —CH=CH—; and hydrogen atom in the group may be replaced by fluorine atom;

$Y_4$ represents —CN or —C≡C—CN;

ring E represents trans-1,4-cyclohexylene, 1,4-phenylene, 1,3-dioxane-2,5-diyl, or pyrimidine-2,5-diyl;

ring G represents trans-1,4-cyclohexylene or pyrimidine-2,5-diyl, or 1,4-phenylene in which hydrogen atom may be replaced by fluorine atom;

ring H represents trans-1,4-cyclohexylene or 1,4-phenylene;

$Z_3$ represents —$CH_2CH_2$—, —COO—, or single bond;

$L_3$, $L_4$, and $L_5$ each independently represent hydrogen atom or fluorine atom;

b, c, and d are each independently 0 or 1; and each atom which constitutes these compounds may be replaced by its isotope,

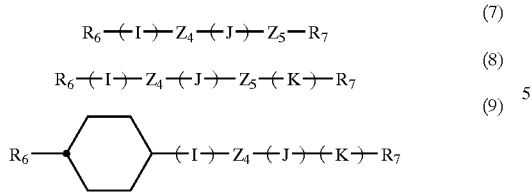

wherein $R_6$, $R_7$, I, J, and K may be the same or different among each of the formulas;

$R_6$ and $R_7$ each independently represent an alkyl group having 1 to 10 carbon atoms in which alkyl group one or not-adjacent two or more methylene groups may be replaced by oxygen atoms or —CH=CH—; and any hydrogen atom in the group may be replaced by fluorine atom;

ring I, ring J, and ring K each independently represent trans-1,4-cyclohexyletie or pyrimidine-2,5-diyl, or 1,4-phenylene in which hydrogen atom may be replaced by fluorine atom;

$Z_4$ and $Z_5$ each independently represent —C≡C—, —COO—, —$CH_2CH_2$—, —CH=CH—, or single bond; and each atom which constitutes these compounds may be replaced by its isotope, and, as an optional component, at least one optically active compound.

16. A liquid crystal display device comprising a liquid crystal composition defined in claim 10.

\* \* \* \* \*